United States Patent
He et al.

(10) Patent No.: US 11,667,667 B2
(45) Date of Patent: *Jun. 6, 2023

(54) STEROID DERIVATIVE FXR AGONIST

(71) Applicant: Chia Tai Tianqing Pharmaceutical Group Co., Ltd., Lianyungang (CN)

(72) Inventors: Haiying He, Pudong New Area Shanghai (CN); Hualing Xiao, Pudong New Area Shanghai (CN); Peng Li, Pudong New Area Shanghai (CN); Chunyan Du, Pudong New Area Shanghai (CN); Zhi Luo, Pudong New Area Shanghai (CN); Shuhui Chen, Pudong New Area Shanghai (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 334 days.

This patent is subject to a terminal disclaimer.

(21) Appl. No.: 17/069,691

(22) Filed: Oct. 13, 2020

(65) Prior Publication Data

US 2021/0040140 A1 Feb. 11, 2021

Related U.S. Application Data

(63) Continuation of application No. 16/072,839, filed as application No. PCT/CN2017/072567 on Jan. 25, 2017, now Pat. No. 10,875,888.

(30) Foreign Application Priority Data

Jan. 28, 2016 (CN) .......................... 201610061293.3
May 18, 2016 (CN) .......................... 201610331759.7

(51) Int. Cl.
  *C07J 43/00* (2006.01)
  *C07J 9/00* (2006.01)
  *C07J 33/00* (2006.01)

(52) U.S. Cl.
  CPC ............... *C07J 43/003* (2013.01); *C07J 9/00* (2013.01); *C07J 33/002* (2013.01)

(58) Field of Classification Search
  None
  See application file for complete search history.

(56) References Cited

U.S. PATENT DOCUMENTS 10,875,888 B2 * 12/2020 He .......................... A61P 31/14
2016/0145296 A1 5/2016 Or
2018/0148470 A1 5/2018 Li

FOREIGN PATENT DOCUMENTS

| CN | 106083978 A | 11/2016 |
| EP | 3290429 A1 | 3/2018 |
| WO | WO 02/072598 A1 | 9/2002 |
| WO | WO 2005/082925 A2 | 9/2005 |
| WO | WO 2016/086218 A1 | 6/2016 |
| WO | WO 2016/161003 A1 | 10/2016 |
| WO | WO 2016/173397 A1 | 11/2016 |
| WO | WO 2016/173493 A1 | 11/2016 |
| WO | WO 2017/147137 A1 | 8/2017 |

OTHER PUBLICATIONS

Pellicciari, R. et al., "Bile Acid Derivatives as Ligands of the Farnesoid X Receptor, Synthesis, Evaluation, and Structure-Activity Relationship of a Series of Body and Side Chain Modified Analogues of Chenodeoxycholic Acid," Journal of Medicinal Chemistry, American Chemistry Society, US, vol. 47, pp. 4559-4569; Jul. 23, 2004; XP002370634; ISSN: 0022-2623 (6 pages).

Pellicciari, R. et al., "Back Door Modulation of the Farnesoid X Receptor: Design, Synthesis and Biological Evaluation of a Series of Side Chain Modified Chenodeoxycholic Acid Derivatives," Journal of Medicinal Chemistry, American Chemistry Society, US; vol. 49, pp. 4208-4215; Jun. 15, 2006; XP008092111; ISSN: 0022-2623 (4 pages).

Yusuke, I. et al., "Effects of Chemical Modification of Ursodeoxycholic Acid on TGR5 Activation," Biological and Pharmaceutical Bulletin (of Japan), vol. 34, No. 1, pp. 1-7; Jan. 1, 2011; XP55594216; ISSN: 0918-6158 (7 pages).

Gioiello, A. et al., "Extending SAR of bile acids as FXR ligands: Discovery of 23-N(carbocinnamyloxy)3α, 7α-dihidroxy-6α-ethyl-24-nor-5β-cholan-23-amine." Bioorganic & Medicinal Chemistry 19, pp. 1650-1658; Mar. 10, 2011 (9 pages).

International Search Report in International Patent Application No. PCT/CN2017/072567, dated May 4, 2017 (6 pages, w/English translation).

Extended European Search Report for European Patent Application No. EP 17743740.7, dated Sep. 11, 2019 (12 pages).

\* cited by examiner

*Primary Examiner* — Zinna Northington Davis
(74) *Attorney, Agent, or Firm* — Nixon Peabody LLP

(57) ABSTRACT

The present invention relates to a compound represented by formula (I), a tautomer thereof or a pharmaceutically acceptable salt thereof, and relates to applications thereof in the preparation of drugs for treating FXR related diseases.

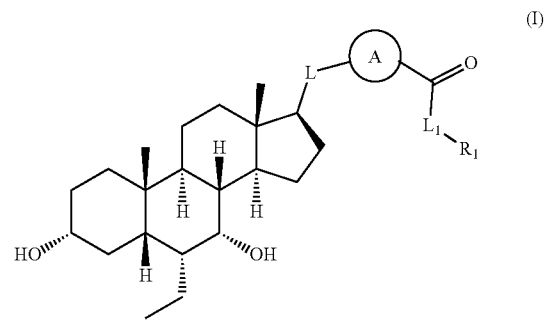

20 Claims, No Drawings

STEROID DERIVATIVE FXR AGONIST

REFERENCE TO RELATED APPLICATIONS

The present application is a continuation of U.S. patent application Ser. No. 16/072,839 filed on Jul. 25, 2018, which has been allowed; U.S. patent application Ser. No. 16/072, 839 is a U.S. national stage of PCT/CN2017/072567 filed on Jan. 25, 2017, which claims the benefit of Chinese Patent Application No. 201610061293.3 filed on Jan. 28, 2016 and Chinese Patent Application No. 201610331759.7 filed on May 18, 2016 in the State Intellectual Property Office of the P. R. China, which are all incorporated by reference in their entireties.

FIELD OF THE INVENTION

The present invention relates to a compound represented by formula (I), a tautomer thereof or a pharmaceutically acceptable salt thereof, and relates to use thereof in the preparation of drugs for treating FXR-related diseases.

BACKGROUND OF THE INVENTION

Farnesoid X Receptor (FXR) is an orphan nuclear receptor originally identified from a liver cDNA library of rat (BM. Forman, et al., Cell, 81: 687-693(1995)), which is most closely related to insect ecdysone receptor. FXR is a member of the ligand-activated transcription factor nuclear receptor family including receptors for steroid, retinoids, and thyroid hormones (DJ. Mangelsdorf, et al., Cell, 83: 841-850(1995)). Northern and in situ analyses show that FXR is greatly expressed in the liver, intestine, kidney, and adrenal gland (BM. Forman et al., Cell, 81: 687-693(1995) and W. Seol et al., Mol. Endocrinnol. 9: 72-85(1995)). FXR binds to DNA after being formed a heterodimer with 9-cis retinoic acid receptor (RXR). FXR/RXR heterodimer preferentially binds to elements composed of two nuclear receptor half sites of the consensus AG(G/T)TCA, which is organized as an inverted repeat and separated by a single nucleotide (IR-1 motif) (BM. Forman, et al., Cell, 81: 687-693(1995)). However, these compounds fail to activate mouse and human FXR, resulting in the nature of the endogenous FXR ligand being uncertain. Several naturally-occurring bile acids bind to and activate FXR at physiological concentrations (PCT WO 00/37077, published on Jun. 29, 2000)). As discussed therein, the bile acids that serve as FXR ligands comprise chenodeoxycholic acid (CDCA), deoxycholic acid (DCA), lithocholic acid (LCA), and taurine and glycine conjugates of these bile acids.

WO-2005082925 discloses the use of INT747 in the preparation of drugs for treating FXR-related diseases.

INT-747

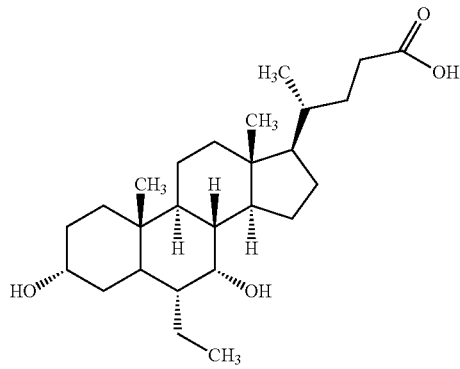

SUMMARY OF THE INVENTION

The object of the present invention is to provide a compound represented by formula (I),

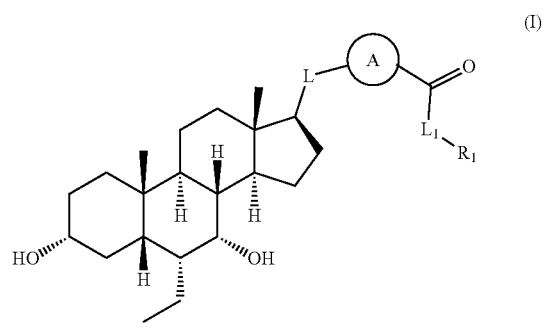

(I)

wherein, ring A is selected from 5- to 12-membered aryl, 5- to 12-membered heteroaryl containing 1 to 2 heteroatoms, 5- to 6-membered non-aromatic heterocyclyl containing 1 to 2 heteroatoms or 5- to 6-membered cycloalkyl, and said ring A is optionally substituted with 1, 2 or 3 $R_a$, or with 1, 2 or 3 oxo groups, and said heteroatom is selected from N, O or S;

L is selected from $C_{1-8}$ alkyl, $C_{1-8}$ heteroalkyl or $C_{2-8}$ alkenyl, and said L is optionally substituted with 1, 2 or 3 Rh, or with 1, 2 or 3 oxo groups;

$L_1$ is selected from O, $N(R_d)$, $N(R_d)S(=O)_2$ or $N(R_d)S(=O)$;

$R_1$ is selected from H, $C_{1-6}$ alkyl, $C_{1-6}$ heteroalkyl, 5- to 6-membered aryl, 4- to 6-membered heteroaryl, $C_{3-6}$ cycloalkyl, or 3- to 6-membered heterocycloalkyl, and said $C_{1-6}$ alkyl, $C_{1-6}$ heteroalkyl, 5- to 6-membered aryl, 4- to 6-membered heteroaryl, $C_{3-6}$ cycloalkyl, or 3- to 6-membered heterocycloalkyl is optionally substituted with 1, 2 or 3 $R_c$, or with 1, 2 or 3 oxo groups;

$R_a$, and $R_d$ are each independently selected from H, F, Cl, Br, I, OH, CN, $NO_2$, $NH_2$, COOH, $S(=O)_2OH$, $C_{1-3}$ alkylamino, N,N-di($C_{1-3}$ alkyl)amino, $C_{1-3}$ alkyl, $C_{1-3}$ alkyloxy or $C_{1-3}$ alkylthio, and said $C_{1-3}$ alkylamino, N,N-di($C_{1-3}$ alkyl)amino, $C_{1-3}$ alkyl, $C_{1-3}$ alkyloxy or $C_{1-3}$ alkylthio is optionally substituted with 1, 2 or 3 R';

R' is selected from F, Cl, Br, I, OH, NH$_2$, NO$_2$, CN, COOH, Me, Et, CH$_2$F, CHF$_2$, CF$_3$, CH$_3$O, CH$_3$S, NH(CH$_3$) or N(CH$_3$)$_2$;

or a pharmaceutically acceptable salt thereof.

In some embodiments of the present invention, in the compound represented by formula (I) or the pharmaceutically acceptable salt thereof, the above R$_a$, R$_b$, R$_c$ and R$_d$ are each independently selected from H, F, Cl, Br, I, COOH, S(=O)$_2$OH, Me, CF$_3$, CHF$_2$, CH$_2$F, Et, OMe, NH(CH$_3$) or N(CH$_3$)$_2$.

In some embodiments of the present invention, in the compound represented by formula (I) or the pharmaceutically acceptable salt thereof, the above ring A is selected from phenyl, pyridyl, pyridin-2(1H)-onyl, pyrimidyl, pyrazolyl, imidazolyl, oxazolyl, thiazolyl, thienyl, pyrrolidinyl, piperidinyl, morpholinyl, piperazinyl, isoxazolyl, isothiazolyl, bicyclo[1.1.1]pentyl, benzoxazolyl, benzo[d]isoxazolyl, indazolyl, indolyl, quinolinyl, isoquinolinyl, quinazolinyl, 1H-pyrrolo[2,3-B]pyridyl, indolizinyl, benzothiazolyl or benzothienyl, and said ring A is optionally substituted with 1, 2 or 3 R$_a$.

In some embodiments of the present invention, in the compound represented by formula (I) or the pharmaceutically acceptable salt thereof, the above ring A is selected from

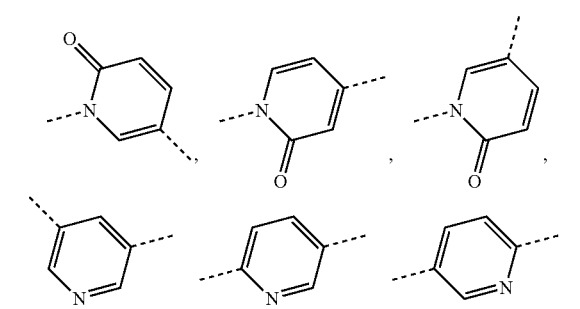

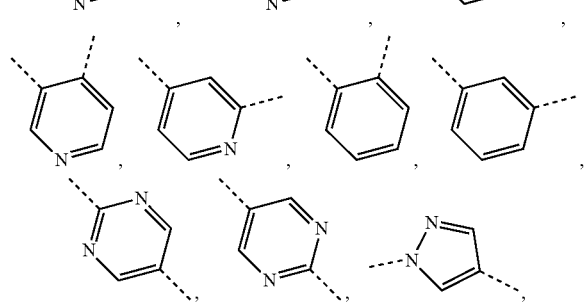

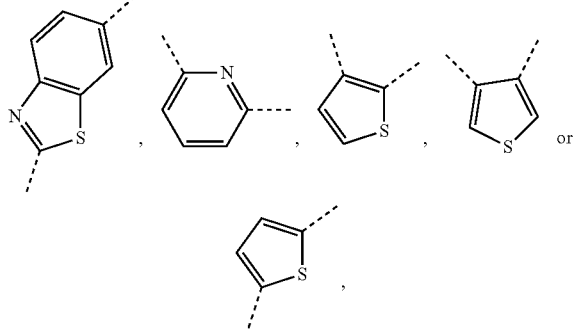

and said ring A is optionally substituted with 1, 2 or 3 R$_a$.

In some embodiments of the present invention, in the compound represented by formula (I) or the pharmaceutically acceptable salt thereof, the above ring A is selected from

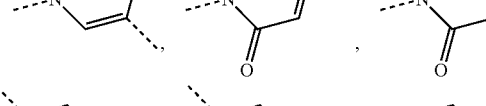

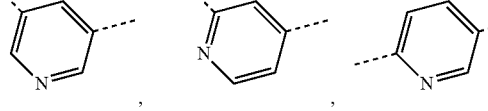

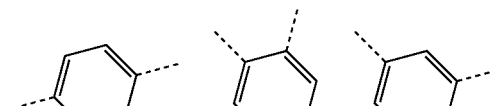

In some embodiments of the present invention, in the compound represented by formula (I) or the pharmaceutically acceptable salt thereof, the above L is selected from $C_{1-4}$ alkyl, $C_{1-4}$ alkoxy, $C_{1-4}$ alkylthio, $C_{1-4}$ alkylamino, $C_{1-4}$ alkyl-C(=O)NH—, $C_{2-4}$ alkenyl or $C_{1-3}$ alkyl-O—$C_{1-3}$ alkyl, and said L is optionally substituted with 1, 2 or 3 $R_b$.

In some embodiments of the present invention, in the compound represented by formula (I) or the pharmaceutically acceptable salt thereof, the above L is selected from and said L is optionally substituted with 1, 2 or 3 $R_b$.

In some embodiments of the present invention, in the compound represented by formula (I) or the pharmaceutically acceptable salt thereof, the above L is selected from In some embodiments of the present invention, in the compound represented by formula (I) or the pharmaceutically acceptable salt thereof, the above L is selected from

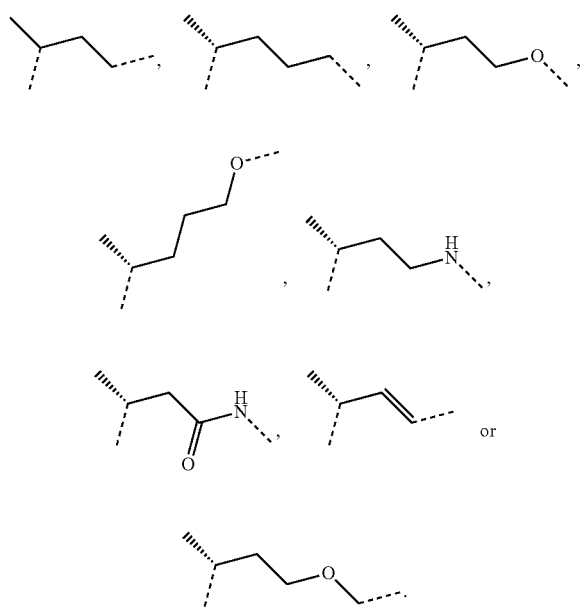

In some embodiments of the present invention, the above $L_1$ is selected from O, NH, NHS(=O)$_2$ and NHS(=O).

In some embodiments of the present invention, in the compound represented by formula (I) or the pharmaceutically acceptable salt thereof, the above $R_1$ is selected from H, $C_{1-3}$ alkyl, $C_{3-6}$ cycloalkyl, phenyl, pyridyl, pyridazinyl, pyrazinyl, imidazolyl, pyrazolyl, thiazolyl, isothiazolyl, oxazolyl, isoxazolyl or thienyl, and said $C_{1-3}$ alkyl, $C_{3-6}$ cycloalkyl, phenyl, pyridyl, pyridazinyl, pyrazinyl, imidazolyl, pyrazolyl, thiazolyl, isothiazolyl, oxazolyl, isoxazolyl or thienyl is optionally substituted with 1, 2 or 3 $R_c$, and said $R_c$ is as above defined.

In some embodiments of the present invention, in the compound represented by formula (I) or the pharmaceutically acceptable salt thereof, the above $R_1$ is selected from H, Me,

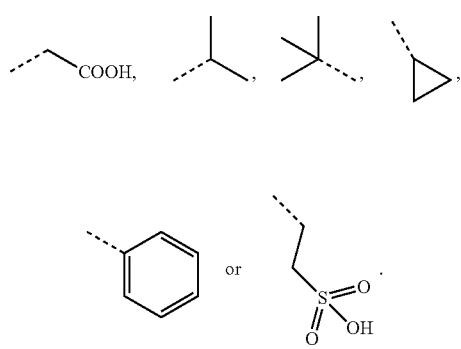

As preferred embodiments, the compound represented by formula (I) or the pharmaceutically acceptable salt thereof is selected from the compound represented by the following formula (II):

![Formula II structure]

wherein, $L_2$ is selected from $C_{1-6}$ alkyl, $C_{1-6}$ heteroalkyl or $C_{2-6}$ alkenyl;

ring B is selected from benzene ring or 5- to 6-membered heteroaromatic ring containing 1 to 2 heteroatoms, and said heteroatom is selected from N, O or S;

said ring B is optionally substituted with 1, 2 or 3 $R_2$, or with 1 oxo group, and said $R_2$ is selected from F, Cl, Br, I, OH, CN, NO$_2$, NH$_2$, COOH, S(=O)$_2$OH, $C_{1-3}$ alkylamino, N,N-di($C_{1-3}$ alkyl)amino, $C_{1-3}$ alkyl, $C_{1-3}$ alkyloxy or $C_{1-3}$ alkylthio;

$L_1$ is selected from O, NH, NHS(=O)$_2$ or NHS(=O);

$R_1$ is selected from H, $C_{1-6}$ alkyl, $C_{1-6}$ heteroalkyl, 5- to 6-membered aryl, 4- to 6-membered heteroaryl, $C_{3-6}$ cycloalkyl, or 3- to 6-membered heterocycloalkyl, and said $C_{1-6}$ alkyl, $C_{1-6}$ heteroalkyl, 5- to 6-membered aryl, 4- to 6-membered heteroaryl, $C_{3-6}$ cycloalkyl, or 3- to 6-membered heterocycloalkyl are optionally substituted with 1, 2, or 3 $R_e$, or with 1, 2 or 3 oxo groups, and said $R_c$ is selected from F, Cl, Br, I, OH, CN, NO$_2$, NH$_2$, COOH or S(=O)$_2$OH;

or a pharmaceutically acceptable salt thereof.

In some embodiments of the present invention, in the compound represented by formula (II) or the pharmaceutically acceptable salt thereof, $L_2$ is selected from —(CH$_2$)$_{1-6}$—, —(CH$_2$)$_{0-4}$—X—(CH$_2$)$_{0-4}$— or —(CH$_2$)$_{0-4}$—Y—(CH$_2$)$_{0-4}$—, and said X is selected from NH, O or S, and said Y is selected from —CH=CH—, providing that the chain length of $L_2$ is selected from 1 to 6, preferably 2 to 4.

In some embodiments of the present invention, in the compound represented by formula (II) or the pharmaceutically acceptable salt thereof, $L_2$ is selected from —CH$_2$CH$_2$—, —CH$_2$CH$_2$CH$_2$—, —CH=CH—, —CH$_2$CH=CH—, —CH=CHCH$_2$—, —CH$_2$CH$_2$O—, —CH$_2$CH$_2$CH$_2$O—, —CH$_2$CH$_2$NH—, —CH$_2$CH$_2$CH$_2$NH—, —CH$_2$CH$_2$S— or —CH$_2$CH$_2$CH$_2$S—, preferably from —CH$_2$CH$_2$—, —CH$_2$CH$_2$CH$_2$—, —CH=CH—, —CH$_2$CH$_2$O—, —CH$_2$CH$_2$CH$_2$O— or —CH$_2$CH$_2$NH—.

In some embodiments of the present invention, in the compound represented by formula (II) or the pharmaceutically acceptable salt thereof, ring B is selected from benzene ring, 5-membered heteroaromatic ring containing 1 to 2 heteroatoms selected from N, O or S, or 6-membered heteroaromatic ring containing 1 to 2 heteroatoms selected from N, and said ring B is optionally substituted with 1, 2, or 3 $R_2$ or with 1 oxo group, and said $R_2$ is as above defined.

In some embodiments of the present invention, in the compound represented by formula (II) or the pharmaceutically acceptable salt thereof, ring B is selected from benzene ring, pyrazolyl, imidazolyl, oxazolyl, isoxazolyl, thiazolyl, isothiazolyl, pyridyl, pyridazinyl, pyrimidinyl or pyrazinyl, and said ring B is optionally substituted with 1, 2 or 3 of $R_2$ or with 1 oxo group, and said $R_2$ is as above defined.

In some embodiments of the present invention, in the compound represented by formula (II) or the pharmaceutically acceptable salt thereof, said ring B is optionally substituted with 1 $R_2$, or with 1 oxo group, and said $R_2$ is selected from F, Cl, Br, I, OH, CN, $NO_2$, $NH_2$, COOH or $S(=O)_2OH$, preferably from F, Cl or Br.

In some embodiments of the present invention, in the compound represented by formula (II) or the pharmaceutically acceptable salt thereof, the $R_2$-substituted or oxo-substituted position is at the ortho-position relative to $L_2$ on ring B (a position).

In some embodiments of the present invention, in the compound represented by formula (II) or the pharmaceutically acceptable salt thereof, said $R_1$ is selected from H, $C_{1-3}$ alkyl, $C_{3-6}$ cycloalkyl, phenyl, pyridyl, pyridazinyl, pyrazinyl, imidazolyl, pyrazolyl, thiazolyl, isothiazolyl, oxazolyl, isoxazolyl or thienyl, and said $C_{1-3}$ alkyl, $C_{3-6}$ cycloalkyl, phenyl, pyridyl, pyridazinyl, pyrazinyl, imidazolyl, pyrazolyl, thiazolyl, isothiazolyl, oxazolyl, isoxazolyl, or thienyl is optionally substituted with 1, 2, or 3 $R_c$, and said $R_c$ is as above defined.

In some embodiments of the present invention, in the compound represented by formula (II) or the pharmaceutically acceptable salt thereof, said $R_1$ is selected from H, Me,

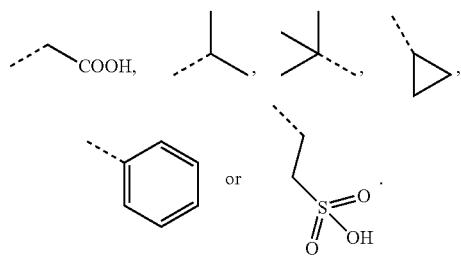

In some embodiments of the present invention, in the compound represented by formula (II) or the pharmaceutically acceptable salt thereof, the structure moiety $L_1$-$R_1$ is selected from —OH, —NHSO$_2$CH$_3$,

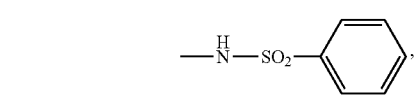

—NHSO$_2$C(CH$_3$)$_3$,  —NHCH$_2$CH$_2$SO$_2$OH.
—NHCH$_2$COOH.

—NHSO$_2$CH(CH$_3$)$_2$,

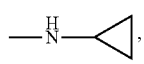

—NHCH$_3$, —OCH$_3$ or

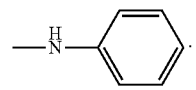

In some embodiments of the present invention, in the compound represented by formula (II) or the pharmaceutically acceptable salt thereof, the structure moiety

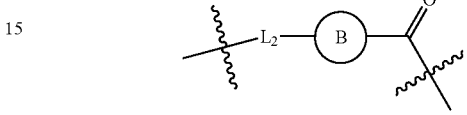

is selected from

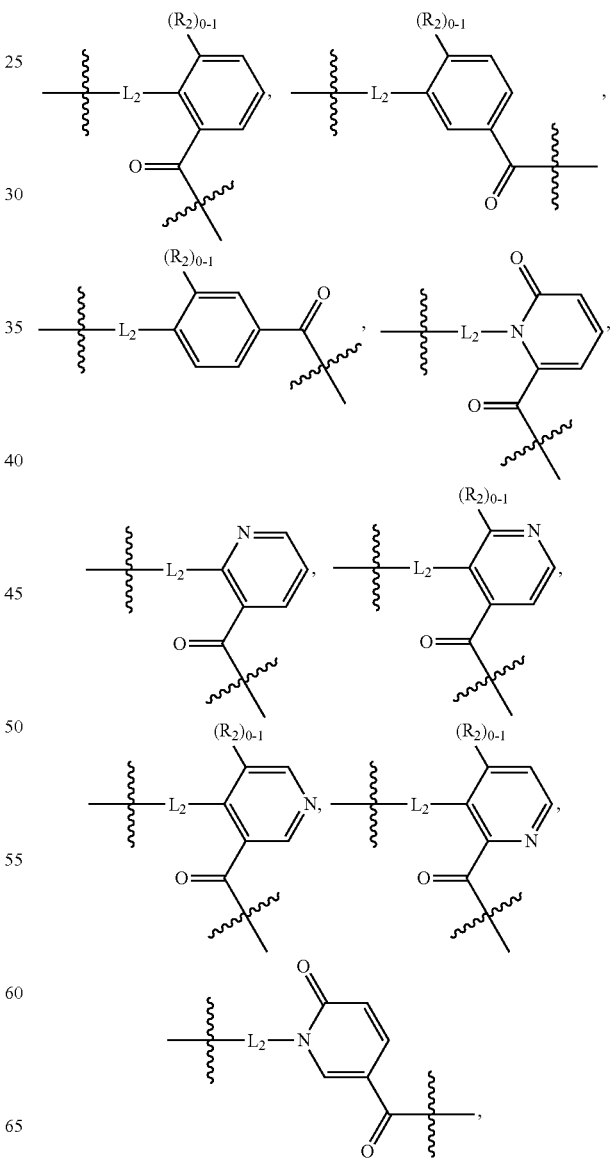

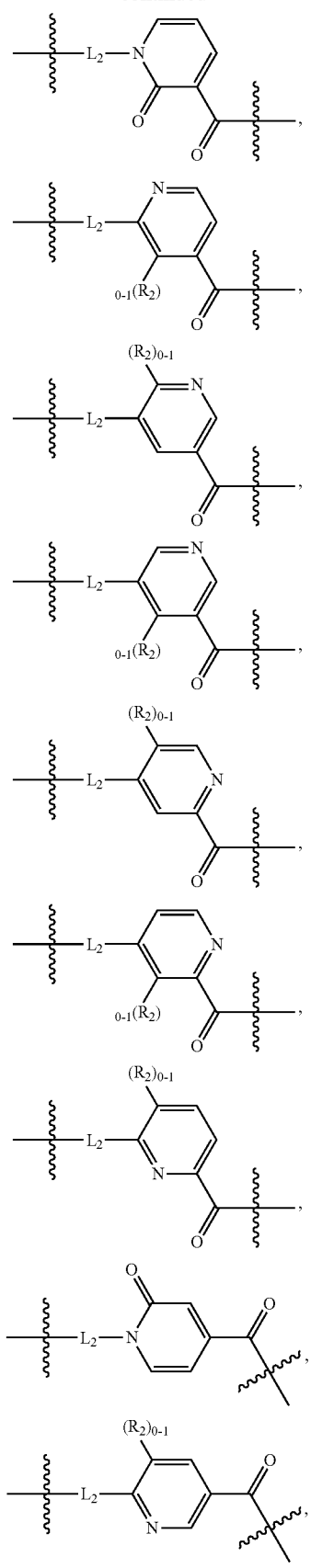
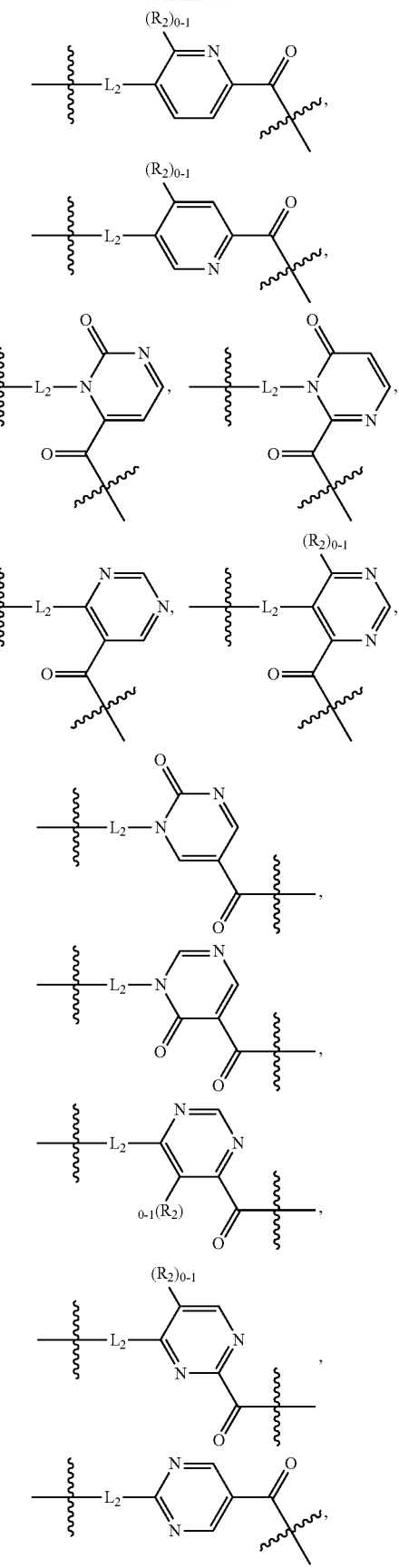

-continued
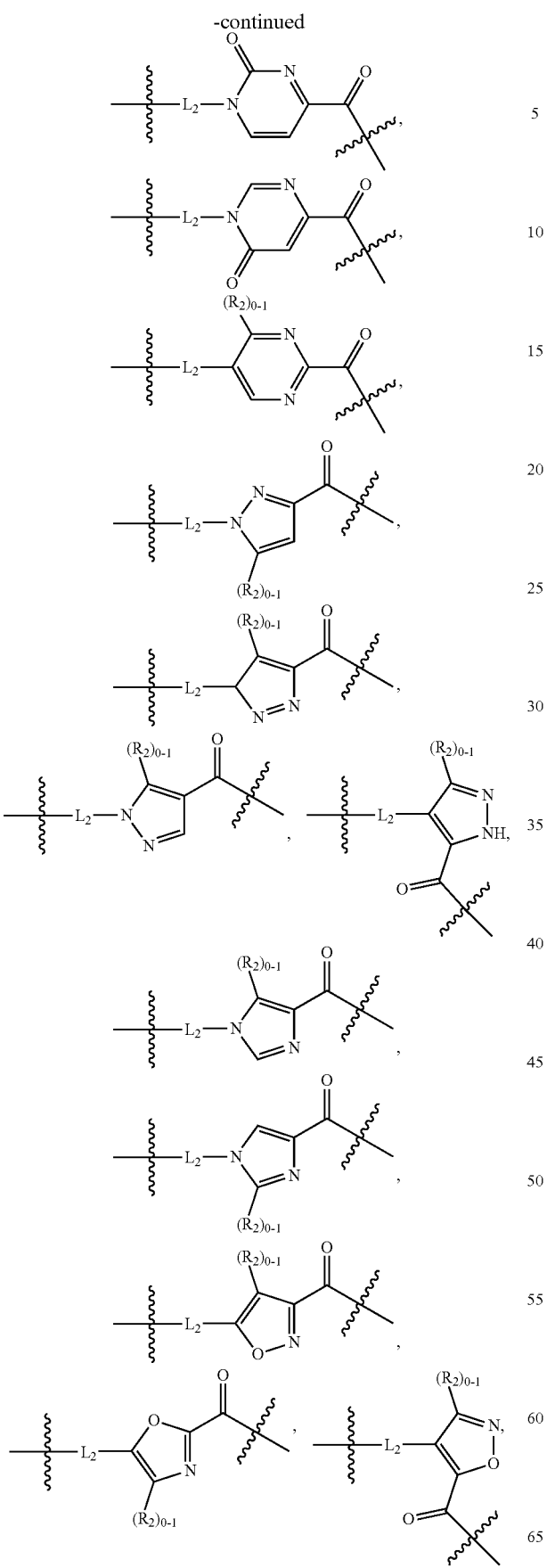
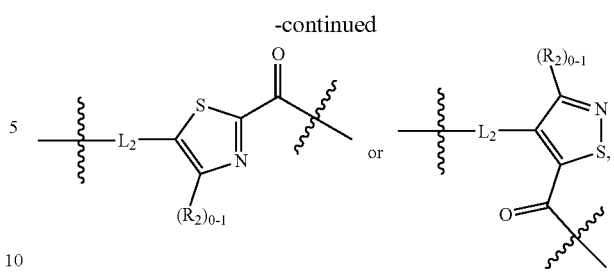
and said $L_2$ and $R_2$ are as above defined.
In some embodiments of the present invention, in the compound represented by formula (II) or the pharmaceutically acceptable salt thereof, the structure moiety
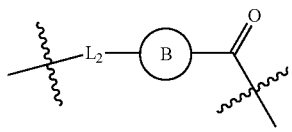
is selected from
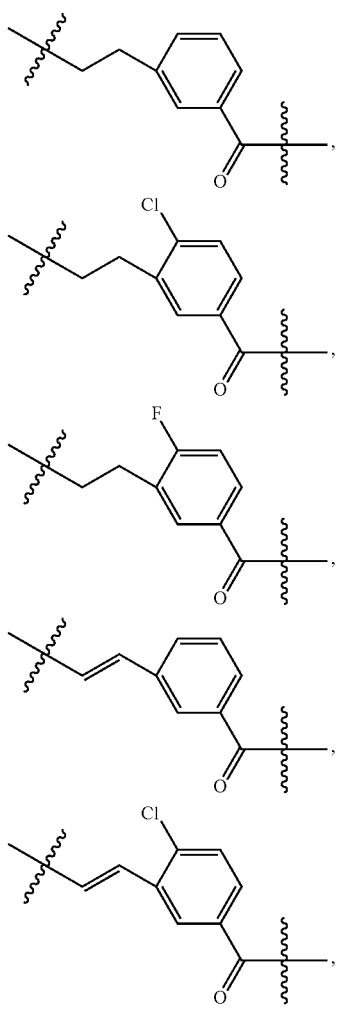

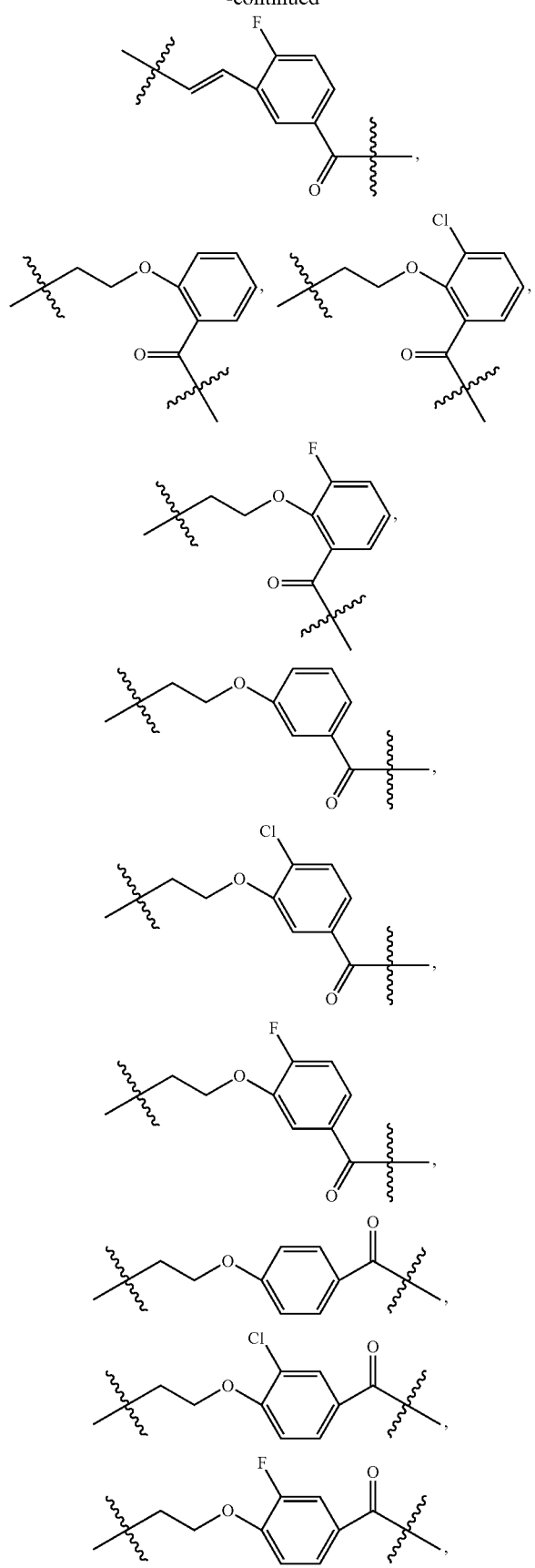
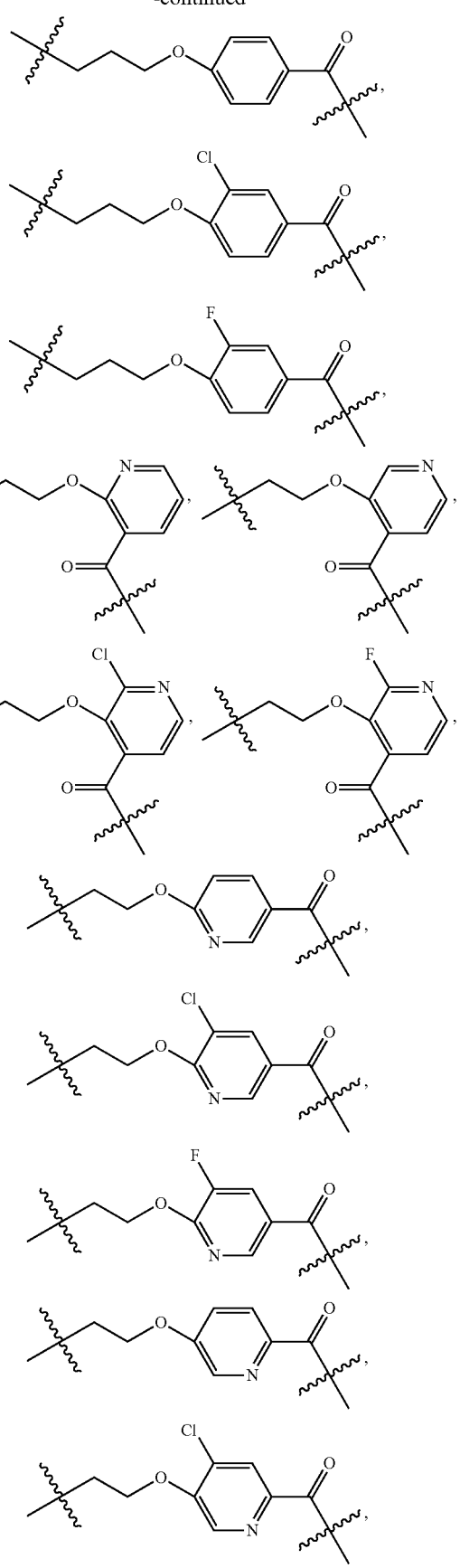

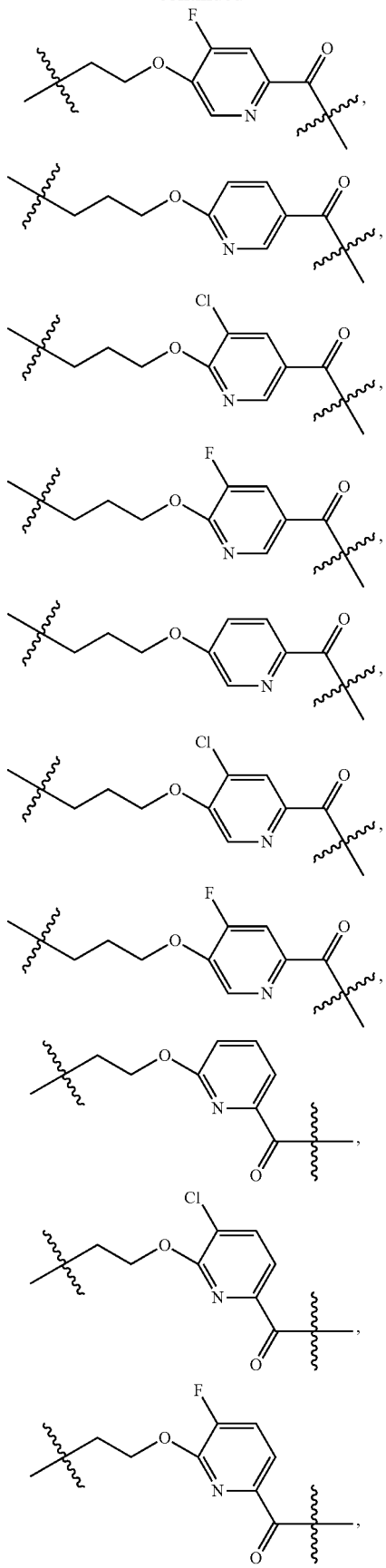

-continued

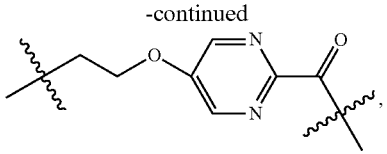,

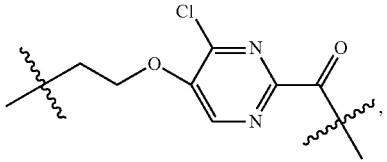,

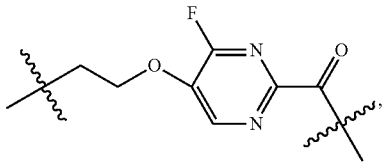,

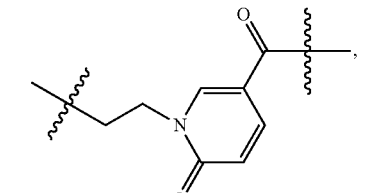,

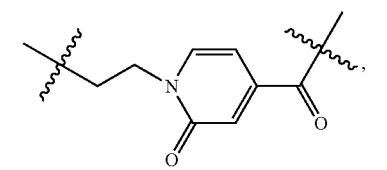,

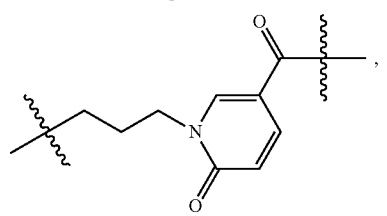,

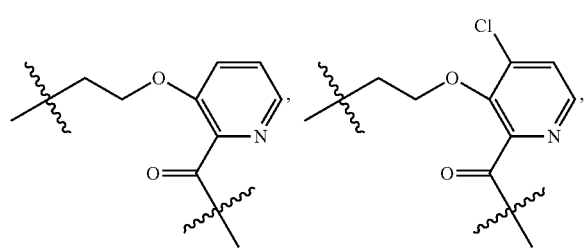,

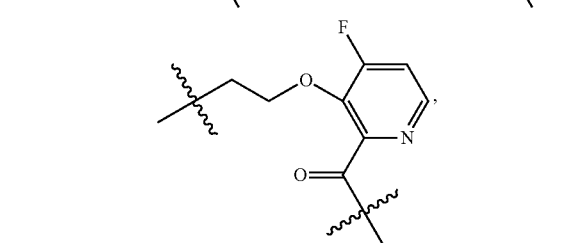,

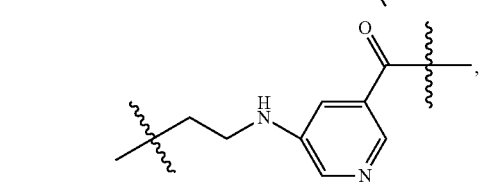,

-continued

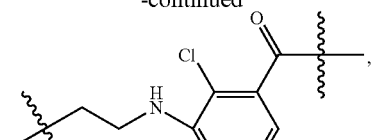,

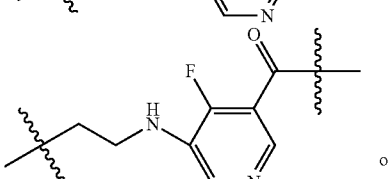 or

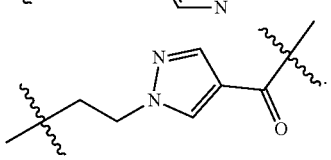.

The present invention also provides a compound represented by formula (III):

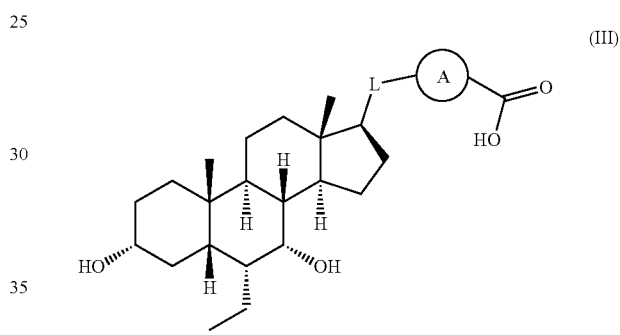

(III)

wherein, ring A is 5- to 12-membered aryl, 5- to 12-membered heteroaryl, or 5- to 6-membered non-aromatic heterocyclyl, 5- to 6-membered cycloalkyl, optionally substituted with 1, 2 or 3 of R;

L is $C_{1-6}$ alkyl, $C_{1-6}$ heteroalkyl, $C_{2-6}$ alkenyl, optionally substituted with 1, 2 or 3 of R;

R is F, Cl, Br, I, OH, CN, $NO_2$, $NH_2$, or R is selected from $C_{1-3}$ alkylamino, N,N-di($C_{1-3}$ alkyl)amino, $C_{1-3}$ alkyl, $C_{1-3}$ alkyloxy, $C_{1-3}$ alkylthio, optionally substituted with 1, 2 or 3 R';

R' is selected from F, Cl, Br, I, OH, $NH_2$, $NO_2$, CN, COOH, Me, Et, $CH_2F$, $CHF_2$, $CF_3$, $CH_3O$, $CH_3S$, $NH(CH_3)$, $N(CH_3)_2$;

said "hetero" represents heteroatom or heteroatomic group, selected from —C(═O)NH—, N, —NH—, —C(═NH)—, —S(═O)$_2$NH—, —S(═O)NH—, —O—, —S—, N, ═O, ═S, —C(═O)O—, —C(═O)—, —C(═S)—, —S(═O)—, —S(═O)$_2$—, and —NHC(═O)NH—;

in any of the above cases, the number of the heteroatom or heteroatomic groups is independently selected from 1, 2 or 3;

or a pharmaceutically acceptable salt thereof.

In some embodiments of the present invention, in the compound represented by formula (III) or the pharmaceutically acceptable salt thereof, the above R is selected from F, Cl, Br, I, Me, $CF_3$, $CHF_2$, $CH_2F$, Et, OMe, $NH(CH_3)$, $N(CH_3)_2$.

In some embodiments of the present invention, in the compound represented by formula (III) or the pharmaceutically acceptable salt thereof, the above ring A is phenyl, pyridyl, pyridin-2(1H)-onyl, pyrimidyl, pyrazolyl, imidazolyl, oxazolyl, thiazolyl, thienyl, pyrrolidinyl, piperidinyl, morpholinyl, piperazinyl, isoxazolyl, isothiazolyl, bicyclo[1.1.1]pentyl, benzoxazolyl, benzo[d]isoxazolyl, indazolyl, indolyl, quinolinyl, isoquinolinyl, quinazolinyl, 1H-pyrrolo[2,3-B]pyridyl, indolizinyl, benzothiazolyl and benzothienyl, optionally substituted with 1, 2 or 3 of R.

In some embodiments of the present invention, in the compound represented by formula (III) or the pharmaceutically acceptable salt thereof, the above ring A is selected from

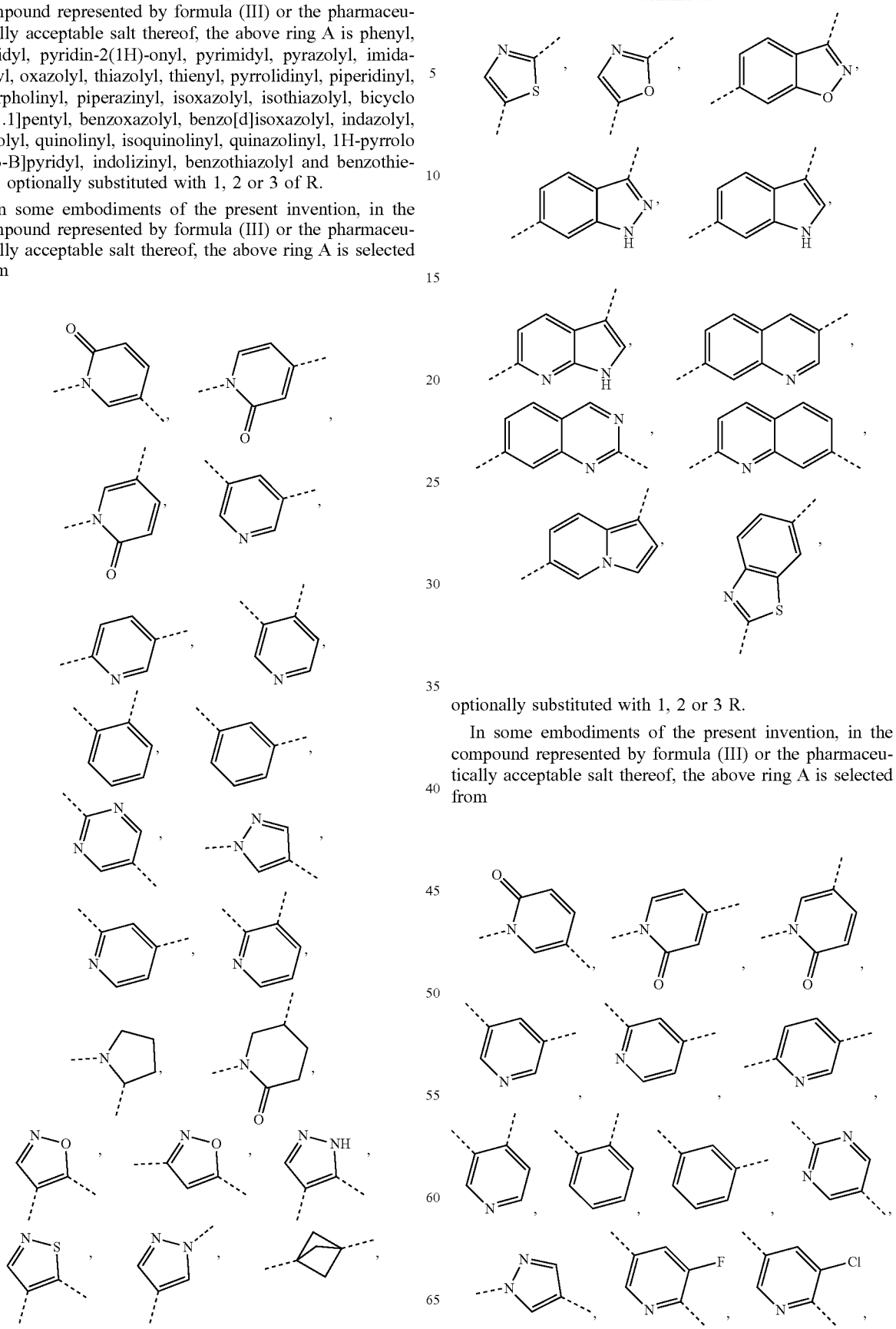

optionally substituted with 1, 2 or 3 R.

In some embodiments of the present invention, in the compound represented by formula (III) or the pharmaceutically acceptable salt thereof, the above ring A is selected from

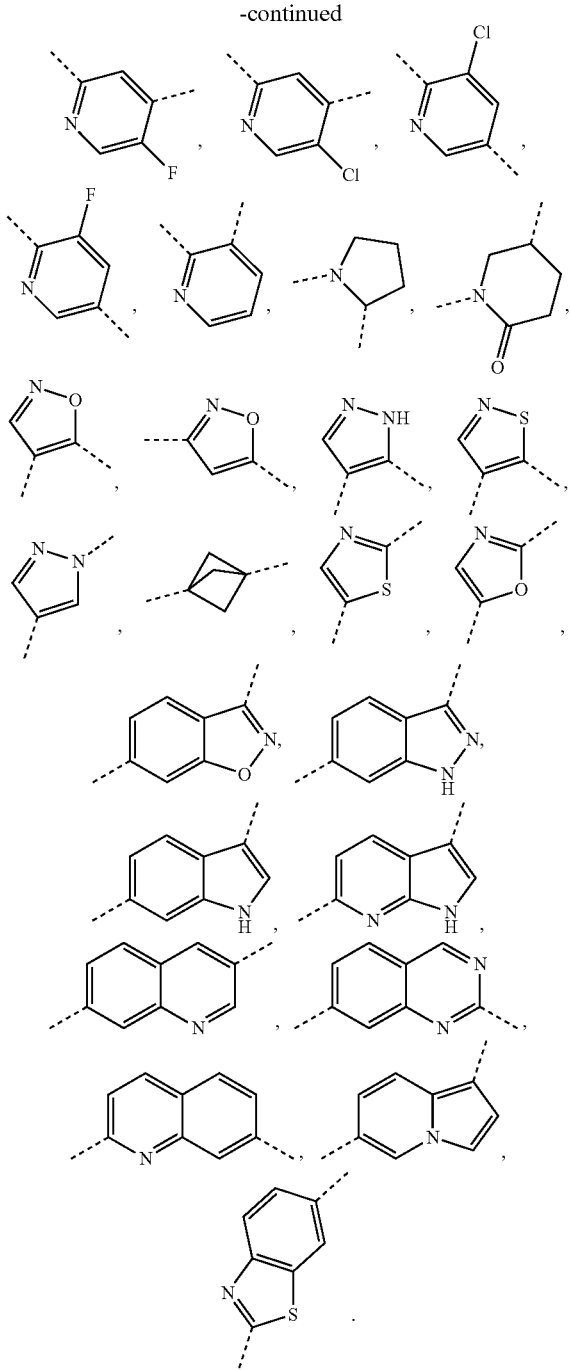

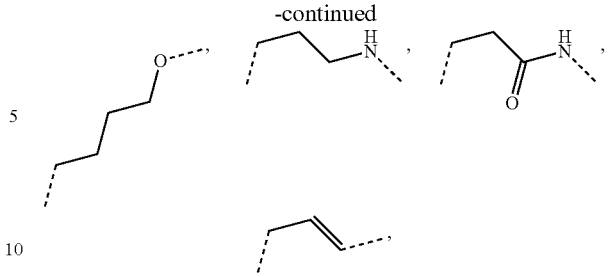

In some embodiments of the present invention, in the compound represented by formula (III) or the pharmaceutically acceptable salt thereof, the above L is selected from $C_{1-4}$ alkyl, $C_{1-4}$ alkoxy, $C_{1-4}$ alkylthio, $C_{1-4}$ alkylamino, $C_{1-4}$ alkyl-C(=O)NH—, $C_{2-4}$ alkenyl, optionally substituted with 1, 2 or 3 R.

In some embodiments of the present invention, in the compound represented by formula (III)

or the pharmaceutically acceptable salt thereof, the above L is selected from optionally substituted with 1, 2 or 3 R.

In some embodiments of the present invention, in the compound represented by formula (III) or the pharmaceutically acceptable salt thereof, the above L is selected from

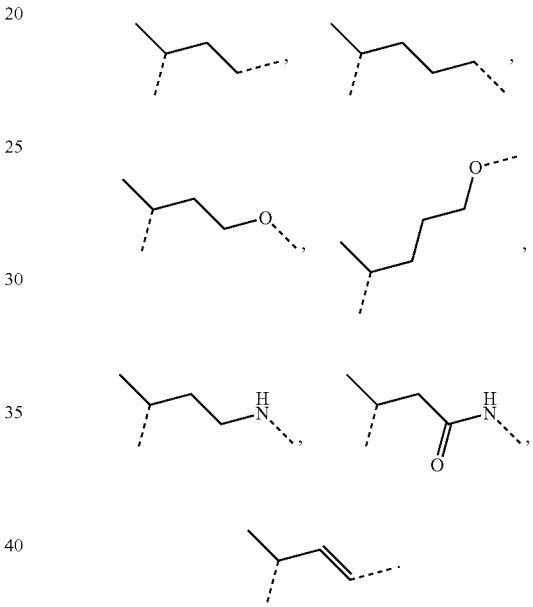

In some embodiments of the present invention, in the compound represented by formula (III) or the pharmaceutically acceptable salt thereof, the above L is selected from

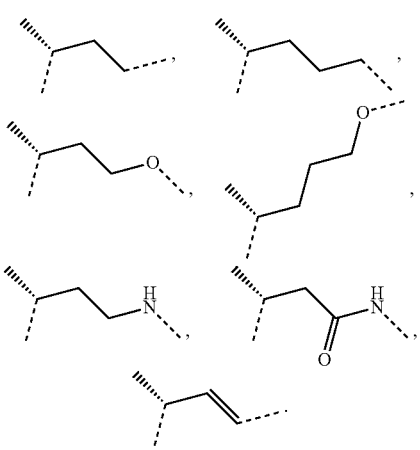

The compound of the present invention is selected from:
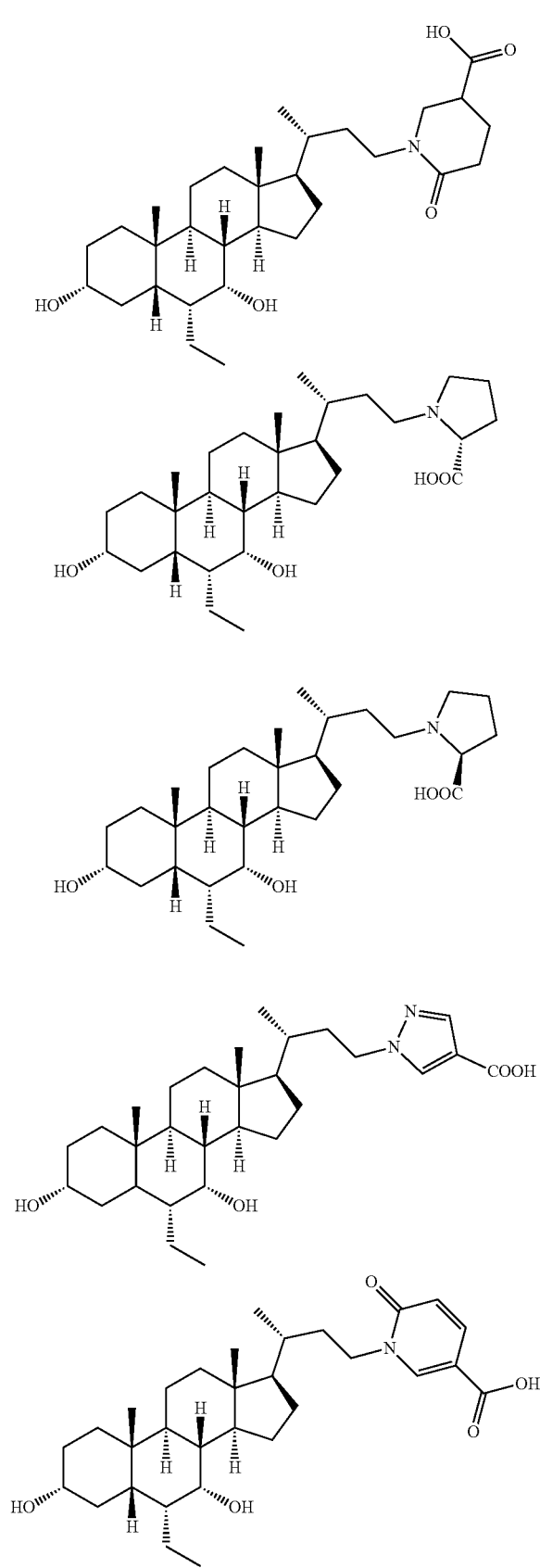
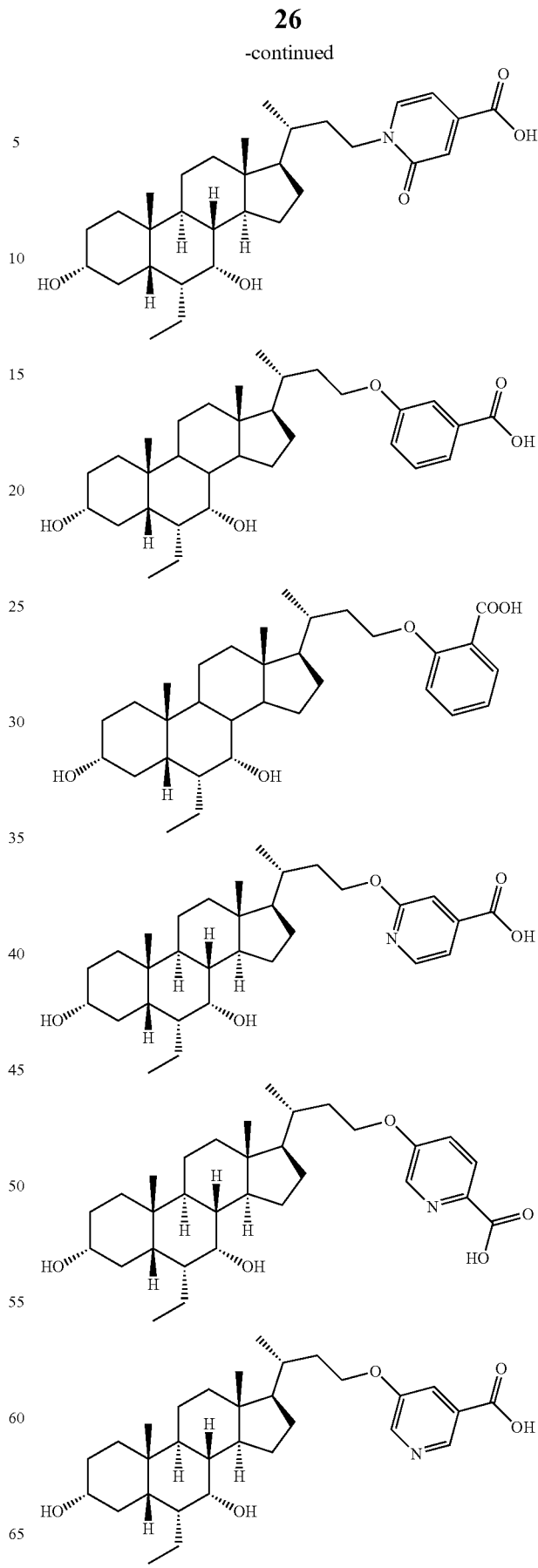

27
-continued
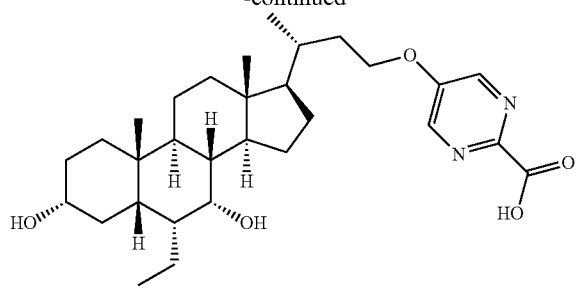
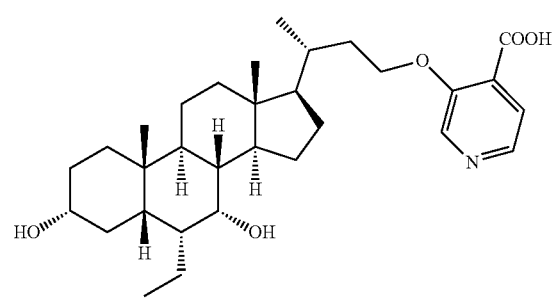
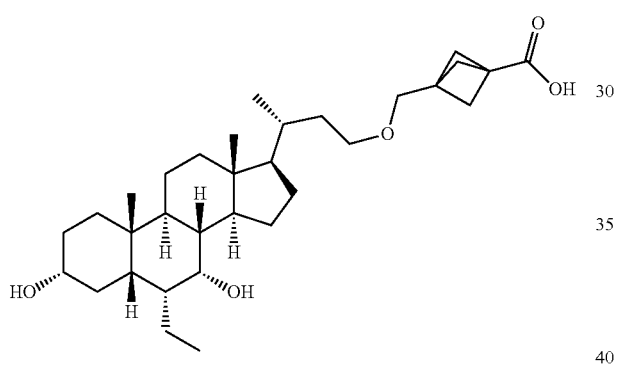
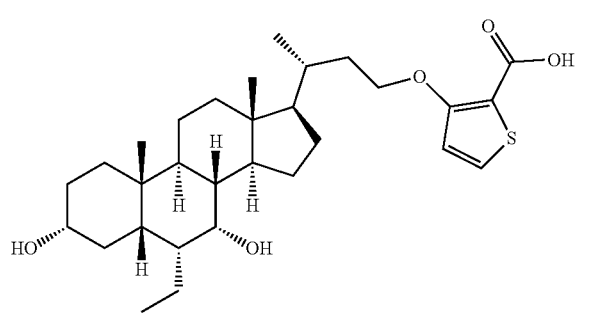
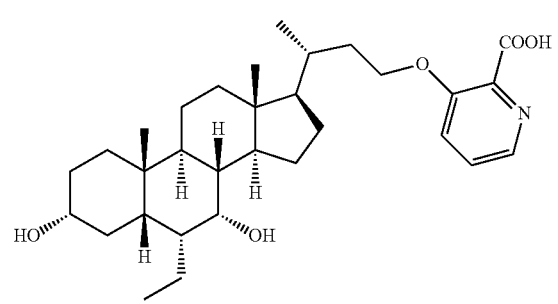
28
-continued
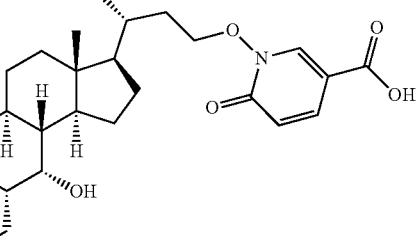
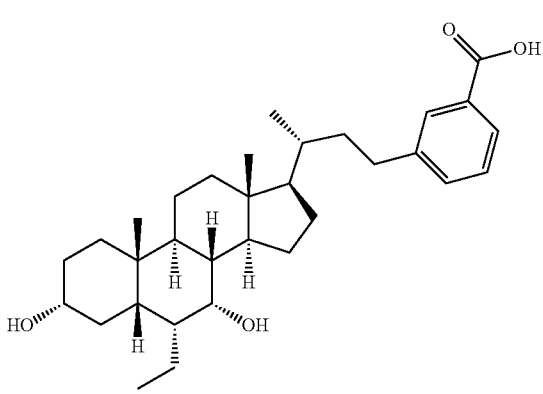
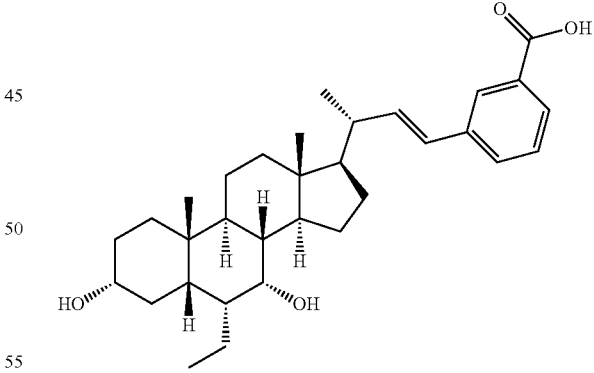
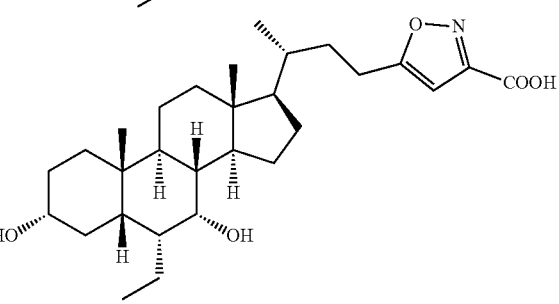

-continued
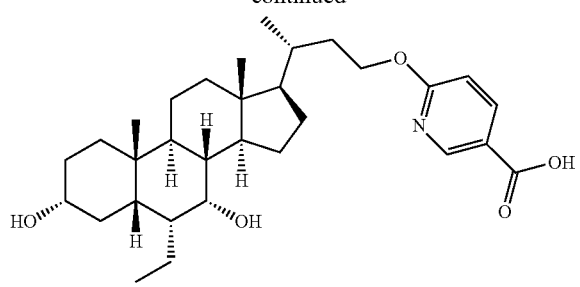
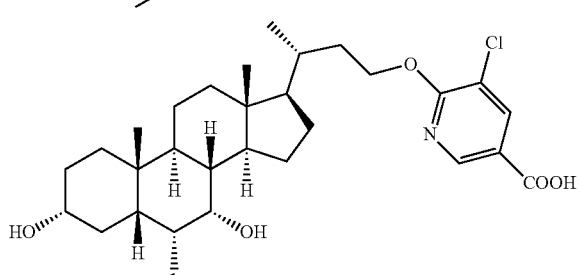
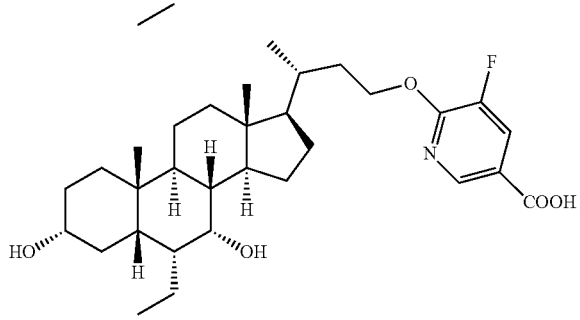
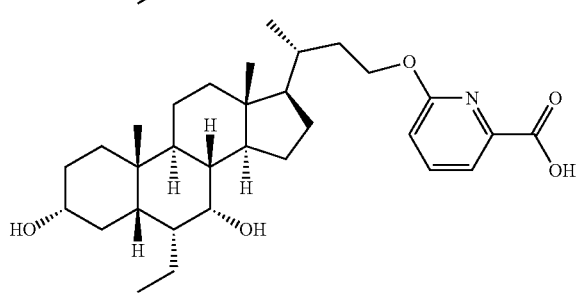
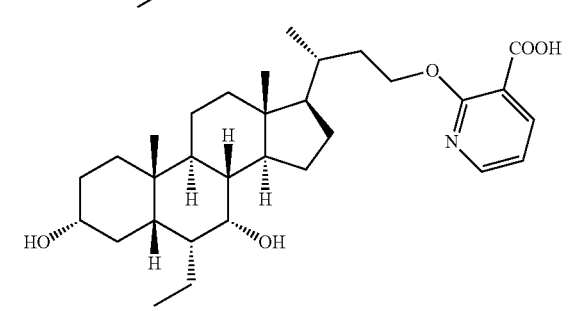
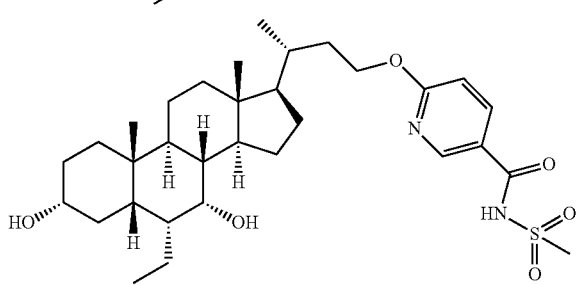
-continued
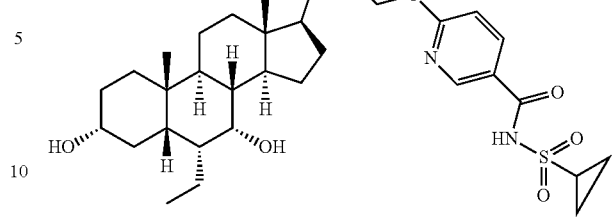
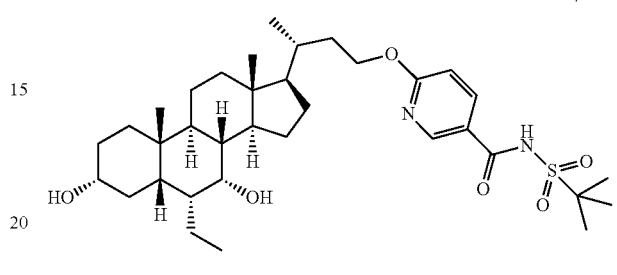
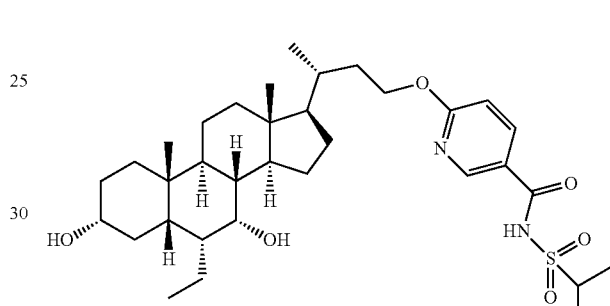
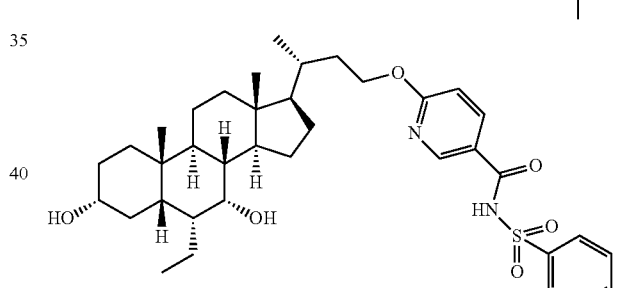
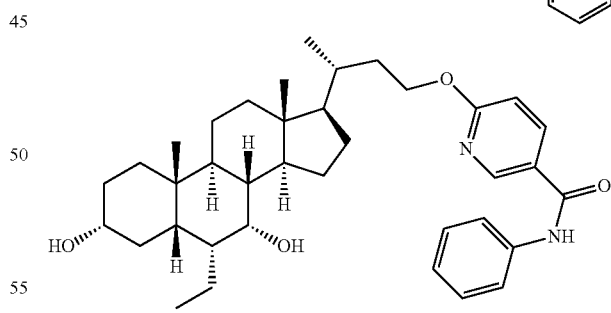
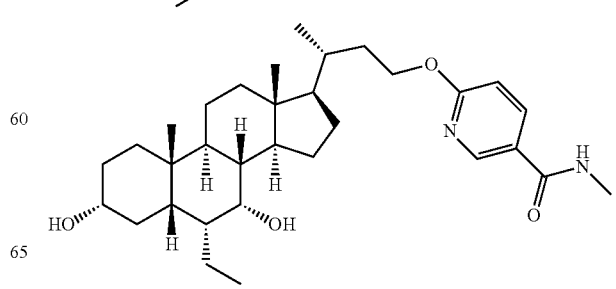

31
-continued
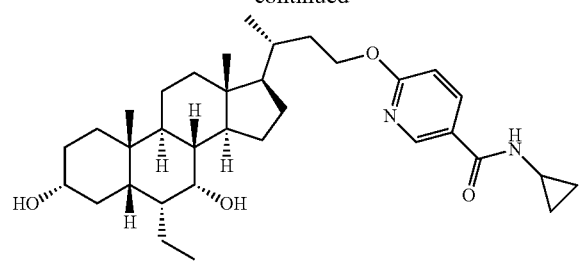
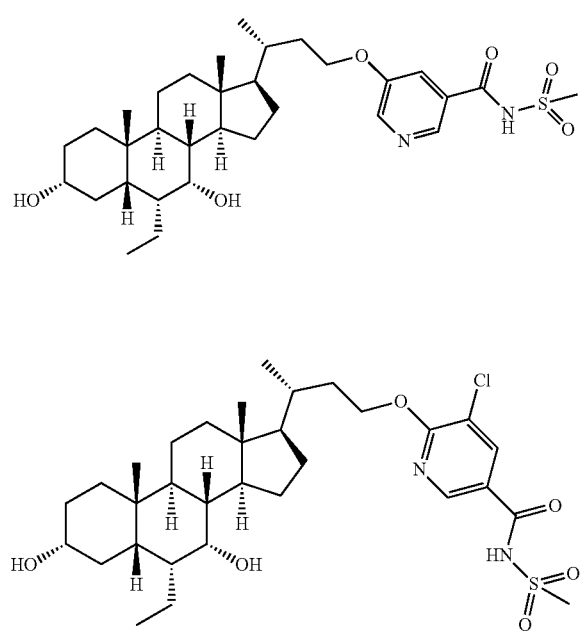
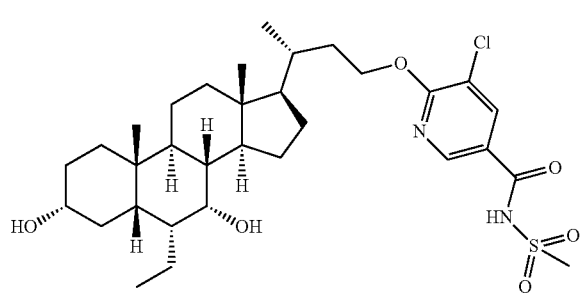
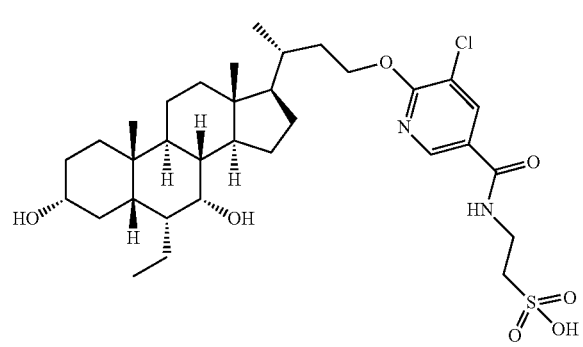
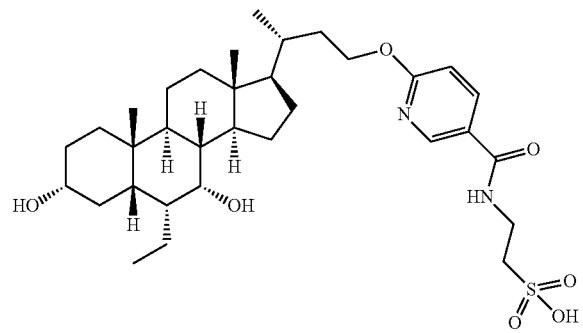
32
-continued
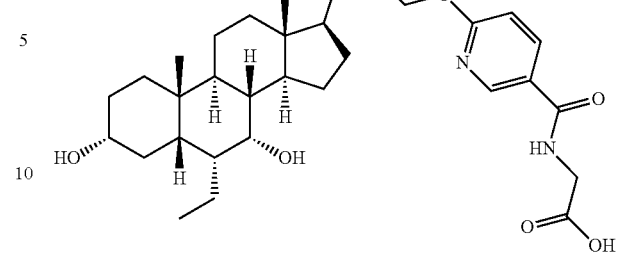
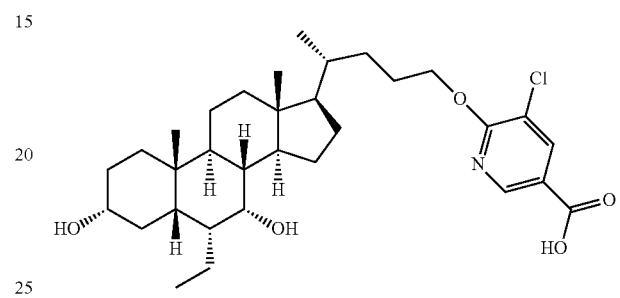
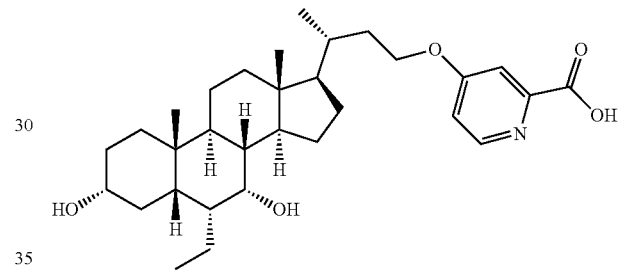
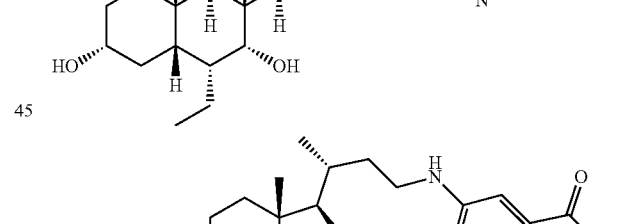
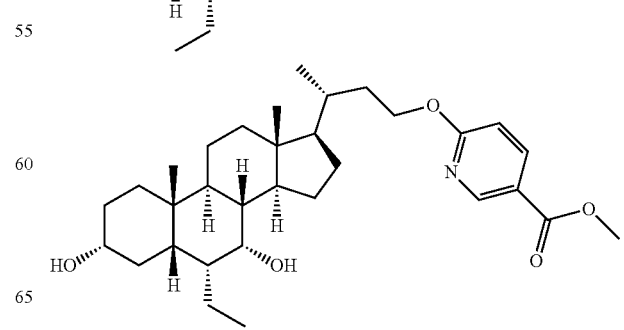

-continued
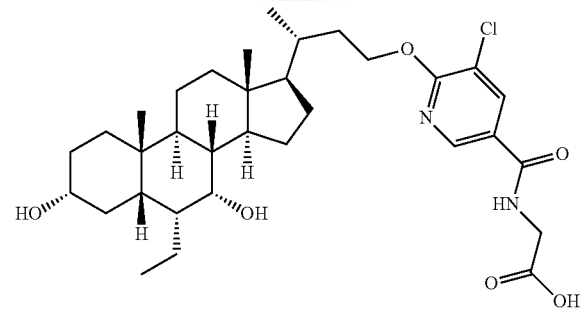
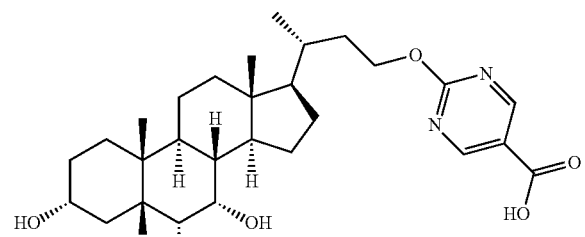
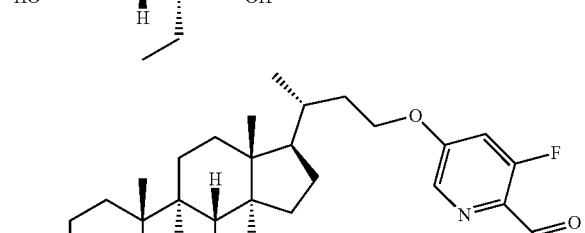
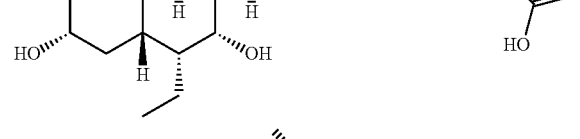
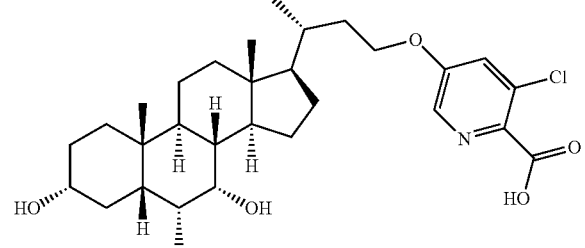
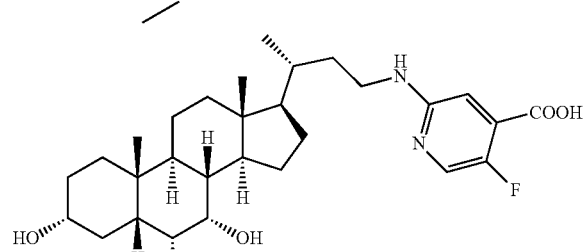
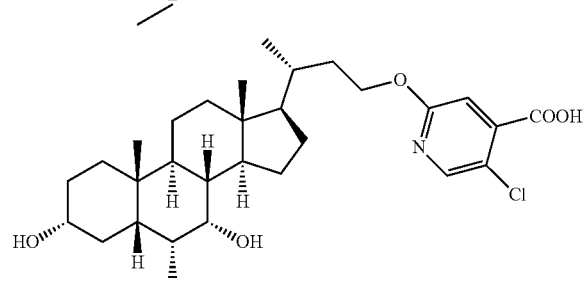
-continued
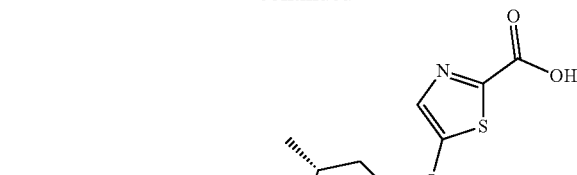
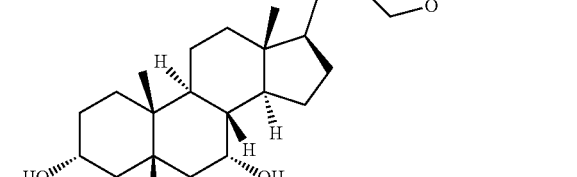
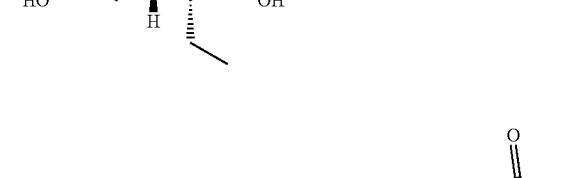
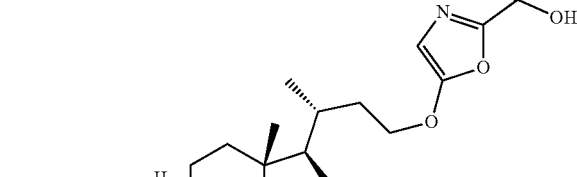
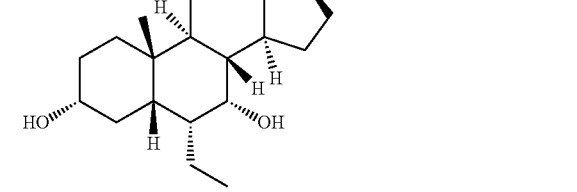
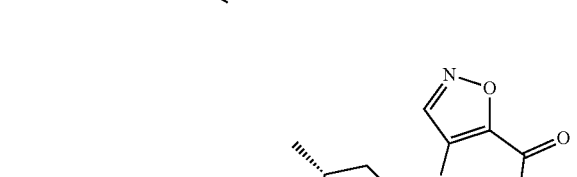
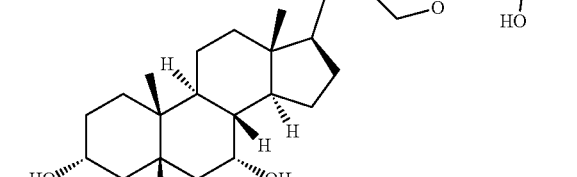
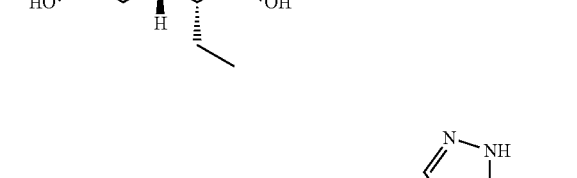
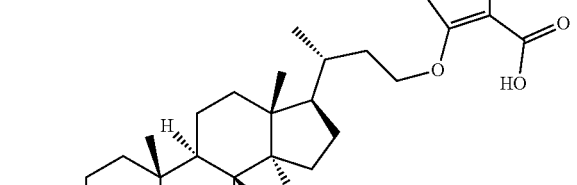

35
-continued
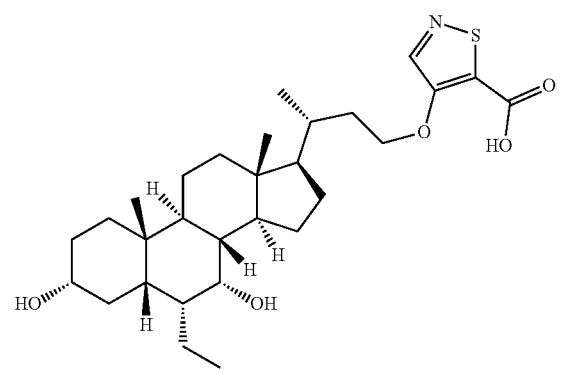
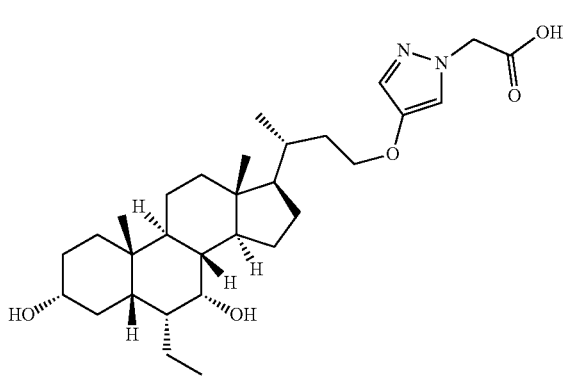
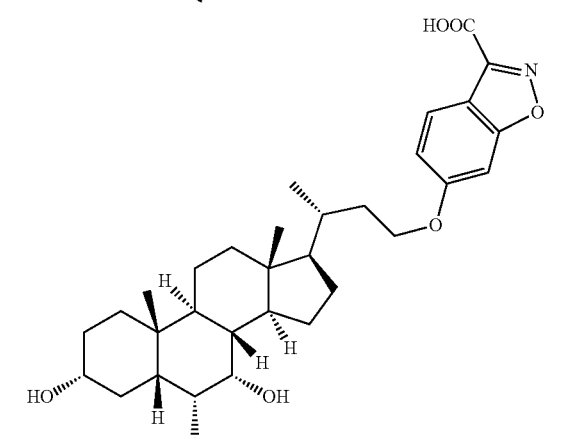
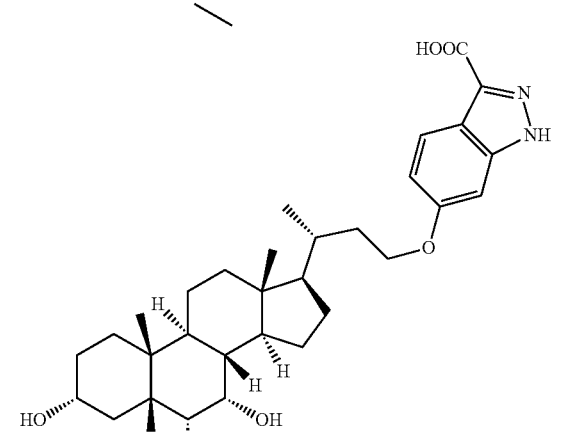
36
-continued
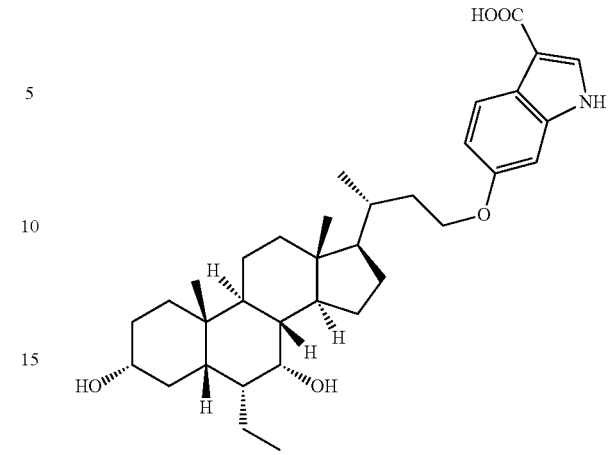
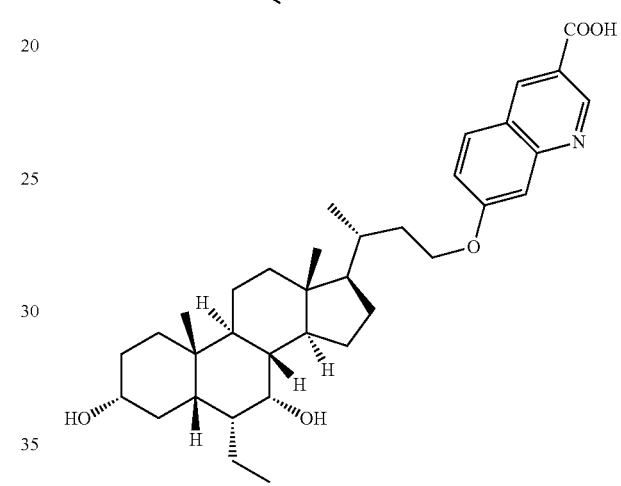
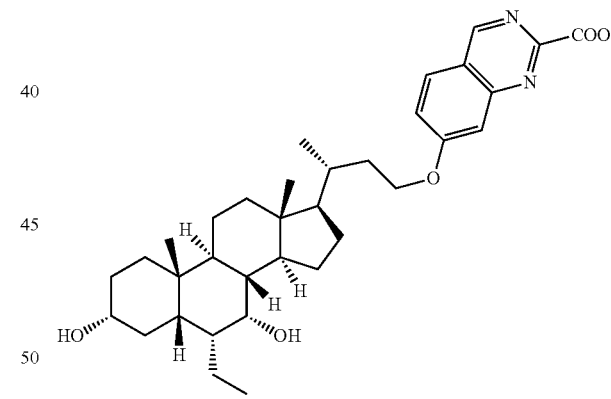
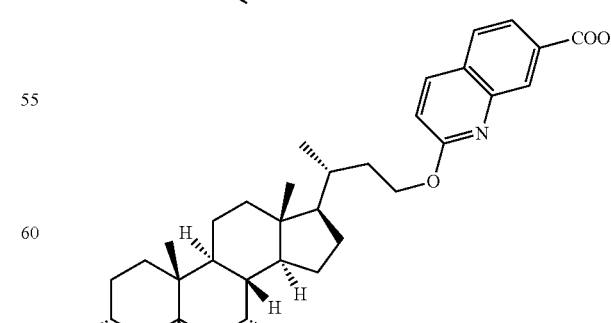

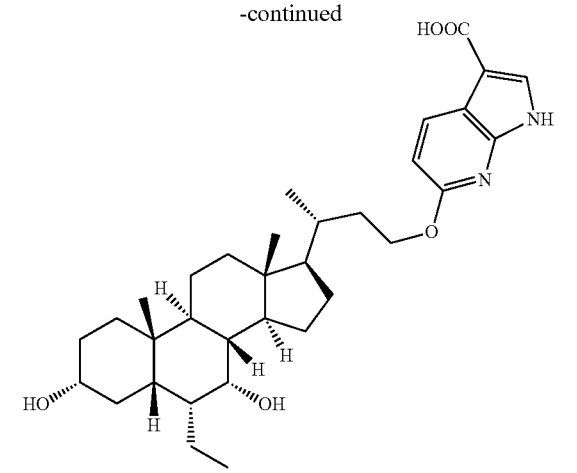

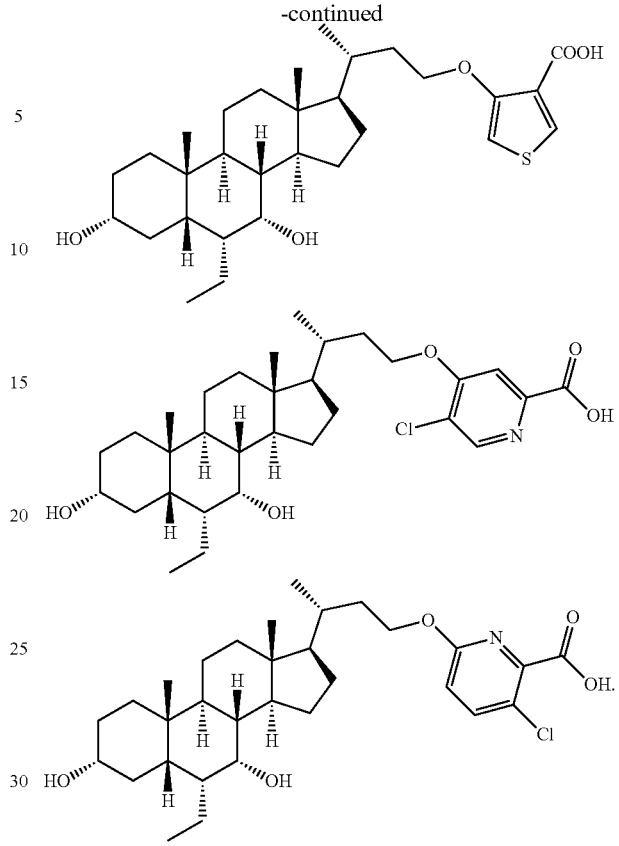

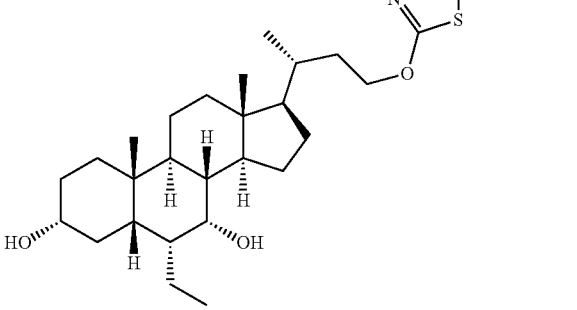

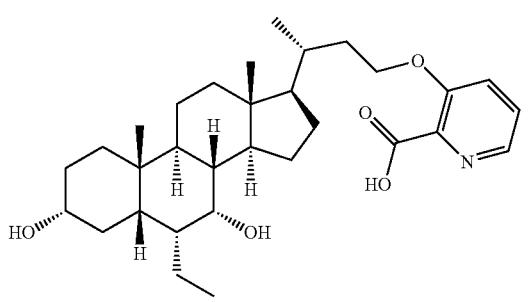

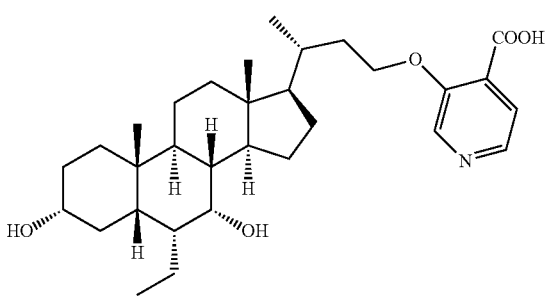

The present invention also provides a pharmaceutical composition comprising a therapeutically effective amount of the above compound or a pharmaceutically acceptable salt thereof, and a pharmaceutically acceptable carrier.

The present invention also provides use of the above compound, or the pharmaceutically acceptable salt thereof, or the above pharmaceutical composition in the preparation of a drug for treating Farnesoid X Receptor related diseases, cholestatic liver diseases, fibrotic diseases, hypercholesterol diseases, hypertriglyceride diseases and cardiovascular diseases.

The present invention also provides use of the above compound, or the pharmaceutically acceptable salt thereof, or the above pharmaceutical composition in the preparation of a drug for treating non-alcoholic fatty liver disease (NAFLD), non-alcoholic steatohepatitis (NASH), primary biliary cirrhosis (PBC), cholestatic hepatopathy, chronic liver disease, hepatitis C infection, alcoholic liver disease, hepatic fibrosis, primary sclerosing cholangitis (PSC), gallstone, biliary atresia, lower urinary tract symptom and benign prostatic hyperplasia (BPH), ureteral calculi, obesity, type 2 diabetes, atherosclerosis, arteriosclerosis, hepatic function injury resulting from hypercholesterolemia and hyperlipidemia.

The compound of the present invention is FXR agonist. The compound of the invention can be used for methods of preventing or treating dyslipidemia or diseases associated with dyslipidemia, comprising administering a therapeutically effective amount of the compound of the present invention to a patient in need thereof.

The compound of the present invention can be used for reducing total cholesterol level, reducing LDL cholesterol level, reducing VLDL cholesterol level, increasing HDL cholesterol level, and/or reducing triglyceride level. Reducing triglyceride level according to the present invention means that the triglyceride level in subjects in need thereof is reduced below the initial triglyceride level of the subjects to be prevented or treated before taking the compounds of the present application. For example, the compound of the present invention can reduce hepatic triglyceride production or hepatic triglyceride secretion by reducing fat absorption. The compound of the present invention can also reduce serum triglyceride and hepatic triglyceride.

The compound of the present invention can be used for preventing or treating cardiovascular diseases associated with hypertriglyceridemia and/or hypercholesterolemia in a subject (e.g., a mammal, particularly human), such as but not limited to, atherosclerosis, arteriosclerosis, hypercholesterolemia, hyperlipidemia, thrombosis, coronary artery disease, stroke or hypertensive disease.

The compound of the present invention can be used for preventing or treating liver/biliary system diseases in a subject (e.g., a mammal, particularly human), such as but not limited to, cholestatic liver diseases, hypercholesterol diseases, hypertriglyceride diseases or fibrotic diseases, such as but not limited to, non-alcoholic steatohepatitis (NASH), primary biliary cirrhosis (PBC), primary sclerosing cholangitis (PSC), gallstone, non-alcoholic cirrhosis, biliary atresia, cholestatic hepatopathy, chronic liver disease, hepatitis infection (type B or C), alcoholic liver disease or hepatic fibrosis.

The compound of the present invention can be used for preventing or treating obesity in a subject (e.g., a mammal, particularly human).

The compound of the present invention can be used for preventing or treating diabetes, or insulin resistance, glucose intolerance related diseases in a subject (e.g., a mammal, particularly human).

The compound of the present invention can be used for preventing or treating lower urinary tract symptom (surrounding area) and benign prostatic hyperplasia (BPH) or ureteral calculi in a subject (e.g., a mammal, particularly human).

Another aspect of the present invention provides use of the compound represented by formula I, II or III, the pharmaceutically acceptable salt thereof or the above pharmaceutical composition in the preparation of a drug for preventing or treating a disease benefiting from FXR agonism, and said disease benefiting from FXR agonism includes cardiovascular diseases, liver/biliary system diseases, obesity, diabetes, lower urinary tract symptom (surrounding area) and benign prostatic hyperplasia (BPH) or ureteral calculi.

Another aspect of the present invention provides a method for preventing or treating a disease benefiting from FXR agonism, comprising administering a therapeutically effective amount of the compound of formula I, II or III, the pharmaceutically acceptable salt thereof, or the above pharmaceutical composition to a patient, and said disease benefiting from FXR agonism includes cardiovascular diseases, liver/biliary system diseases, obesity, diabetes, lower urinary tract symptom (surrounding area) and benign prostatic hyperplasia (BPH) or ureteral calculi.

The cardiovascular diseases include cardiovascular diseases associated with hypertriglyceridemia and/or hypercholesterolemia. The cardiovascular diseases further include atherosclerosis, arteriosclerosis, hypercholesterolemia, hyperlipidemia, thrombosis, coronary artery disease, stroke or hypertension. The liver/biliary system diseases include cholestatic liver diseases, hypercholesterol diseases, hyper- triglyceride diseases or fibrotic diseases. The liver/biliary system diseases further include non-alcoholic steatohepatitis (NASH), primary biliary cirrhosis (PBC), primary sclerosing cholangitis (PSC), gallstone, nonalcoholic cirrhosis, biliary atresia, cholestatic hepatopathy, chronic liver disease, hepatitis infection (type B or C), alcoholic liver disease or hepatic fibrosis.

Definitions and Introductions

Unless otherwise indicated, the following terms and phrases used herein are intended to have the following meanings. A particular term or phrase should not be considered to be indefinite or unclear in the absence of a specific definition, but should be interpreted as its ordinary meanings. When a trade name appears herein, it is intended to refer to the corresponding commodity or active ingredient thereof.

The term "substituted" means that any one or more of the hydrogen atoms on a specific atom are substituted by a substituent, as long as the valence state of the specific atom is normal and the substituted compound is stable.

The term "oxo" means that the two hydrogen atoms on a specific atom are substituted by =O. When an aromatic ring is oxo-substituted, the oxo-substituted ring may remain aromatic, or lose aromaticity. It can be understood that the oxo-substituted group is stable. For example, when the benzene ring is oxo-substituted, it can be selected from

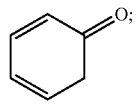

when pyridine is oxo-substituted, it can be selected from

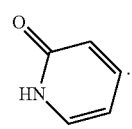

The term "optional" or "optionally" means that the subsequently described event or situation may occur or not, and the description includes the event or situation occurs and not. For example, an ethyl is "optionally" substituted by a halogen, meaning that the ethyl may be unsubstituted ($CH_2CH_3$), monosubstituted (e.g., $CH_2CH_2F$), polysubstituted (e.g., $CHFCH_2F$, $CH_2CHF_2$, etc.) or completely substituted ($CF_2CF_3$). Also, for example, "optionally, said ring B is substituted by 1, 2 or 3 $R_2$, or by 1 oxo group" means that ring B is substituted by 1, 2 or 3 $R_2$ or by 1 oxo group, or ring B is not substituted by $R_2$ or oxo group. It can be understood by the skilled in the art that, for any groups containing one or more substituents, any substitutions or substitution patterns that are unable to exist spatially and/or cannot be synthesized will not be introduced.

The $C_{m-n}$ herein means that the moiety has an integer number of carbon atom in a designated range. For example, "$C_{1-6}$" means that the group may have 1, 2, 3, 4, 5 or 6 carbon atoms.

Numerical range herein means each integer in a designated range. For example, "$C_{1-3}$ alkyl" means that the group may be selected from $C_1$, $C_2$ and $C_3$ alkyl; "$C_{3-10}$ cycloalkyl" means the group may be selected from $C_3$, $C_4$, $C_5$, $C_6$, $C_7$, $C_8$, $C_9$ and $C_{10}$ cycloalkyl; "5- to 6-membered cycloalkyl" means that the group may be selected from 5- and 6-membered heterocycloalkyl.

When any variable (e.g., R) appears more than once in composition or structure of a compound, its definition in each case is independent. Thus, for example, if a group is substituted by 0-2 R, this group may be optionally substituted by at most two R, and R in each case has independent options. Furthermore, the combination of substituents and/or variants thereof is allowed only if such combination results in stable compounds.

When part of groups can be substituted or oxo-substituted herein, the substitution or oxo-substitution is independent with each other, including the cases that the groups are either substituted or oxo-substituted only, or substituted and oxo-substituted simultaneously. For example, when ring A is optionally substituted by 1, 2 or 3 $R_a$, or by 1, 2 or 3 oxo groups, it includes that: 1) there are no substituents and oxo groups on ring A, 2) ring A is only substituted by 1, 2 or 3 $R_a$, 3) ring A is only substituted by 1, 2 or 3 oxo groups, 4) ring A is substituted by $R_a$ and oxo groups simultaneously.

In some preferred embodiments of the present application, part of moiety structures may be connected to other structures at the left end, and may be connected to other structures at the right end at the same time. When a dashed line or a solid line represents a linkage bond, the skilled in the art can understand by reading the present application that the dashed line or solid line directionally indicates the linkage state of the moiety structure with other structures.

For example, if ring A is selected from

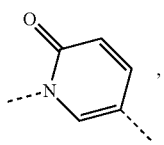

the leftward dashed line indicates that N atom is connected to the L group of the compound represented by Formula (I), and the rightward dashed line indicates that C atom is connected to the carbonyl moiety of the compound represented by formula (I); also, for example, if ring A is selected from

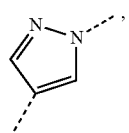

the leftward dashed line indicates that C atom is connected to the L group of the compound represented by formula (I), and the rightward dashed line indicates that N atom is connected to the carbonyl moiety of the compound represented by formula (I). The leftward dashed or solid line refers to protruding to the upper left, left, or lower left from the moiety structure per se; and the rightward dashed or solid line refers to protruding to the upper right, right, or lower right from the moiety structure per se.

In some preferred embodiments of the present invention, the chain length refers to the number of the atoms used to form the open chain group, and the atoms include C atom, N atom, O atom or S atom with different valences. For example, when $L_2$ is selected from —$CH_2CH_2CH_2$—, the chain length is 3; when $L_2$ is selected from —$(CH_2)_2$—O—$(CH_2)_2$—, the chain length is 5; when $L_2$ is selected from —$(CH_2)_2$—CH=CH—$(CH_2)_2$—, the chain length is 6.

The term "halo" or "halogen" refers to fluorine, chlorine, bromine and iodine.

The term "hydroxy" refers to —OH group.
The term "cyano" refers to —CN group.
The term "thiol" refers to —SH group.
The term "amino" refers to —$NH_2$ group.
The term "nitro" refers to —$NO_2$ group.
The term "alkoxy" refers to —O-alkyl.
The term "alkylamino" refers to —NH-alkyl.
The term "dialkylamino" refers to —N(alkyl)$_2$.
The term "alkylsulfonyl" refers to —$SO_2$-alkyl.
The term "alkylthio" refers to —S-alkyl.

The term "alkyl" refers to a hydrocarbyl with the general formula of $C_6H_{2n+1}$. The alkyl may be linear or branched. For example, the term "$C_{1-6}$ alkyl" refers to an alkyl containing 1 to 6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moieties (i.e., alkyl) of alkoxy, alkylamino, dialkylamino, alkylsulfonyl and alkylthio have the same definition as above.

The term "heteroalkyl" refers to an alkyl structure containing a heteroatom. Unless otherwise indicated, the heteroalkyl is typically an alkyl containing 1 to 3 heteroatoms (preferably 1 or 2 heteroatoms) independently selected from sulfur, oxygen and/or nitrogen.

The term "alkenyl" refers to a linear or branched unsaturated aliphatic hydrocarbyl having at least one double bond consisting of carbon and hydrogen atoms. Non-limiting examples of alkenyl include, but are not limited to, vinyl, 1-propenyl, 2-propenyl, 1-butenyl, isobutenyl, 1,3-butadienyl, etc. The term "linear alkenyl" refers to straight chain alkenyl.

The term "aryl" refers to an all-carbon monocyclic group with a conjugated π-electron system or a fused polycyclic aromatic ring group. For example, an aryl may have 6 to 20, 6 to 14, or 6 to 12 carbon atoms. Non-limiting examples of aryl include, but are not limited to, phenyl, naphthyl, anthryl and 1,2,3,4-tetrahydronaphthalene, etc.

The term "heteroaryl" refers to a monocyclic or fused polycyclic system containing at least one cyclic atom selected from N, O, S with the remaining cyclic atoms being C, and having at least one aromatic ring. Preferred heteroaryl has a single 4- to 8-, especially 5- to 8-membered ring, or has a plurality of fused rings containing 6 to 14, especially 6 to 10 cyclic atoms. Non-limiting examples of heteroaryl include, but are not limited to, pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

The term "cycloalkyl" refers to a carbocyclic ring that is fully saturated and can exist as a monocyclic ring, bridged ring or spirocyclic ring. Unless otherwise indicated, the carbocyclic ring is typically a 3- to 10-membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl etc.

The term "non-aromatic heterocyclyl" refers to a fully saturated or partially unsaturated (but not fully unsaturated heteroaromatic) non-aromatic ring that may be present as a monocyclic ring, bicyclic ring or spirocyclic ring. Unless otherwise indicated, the heterocyclic ring is typically a 3- to 6-membered ring containing 1 to 3 heteroatoms (preferably 1 or 2 heteroatoms) independently selected from sulfur, oxygen, and/or nitrogen. Non-limiting examples of heterocyclyl include, but are not limited to oxiranyl, tetrahydrofuranyl, dihydrofuranyl, pyrrolidinyl, N-methyl pyrrolidinyl, dihydropyrrolyl, piperidinyl, piperazinyl, pyrazolidinyl, 4H-pyranyl, morpholinyl, thiomorpholinyl, tetrahydrothienyl, etc.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to the salt of the compound of the present invention, which is prepared from the compound with specific substituents found in the present invention and a relatively nontoxic acid or base. When the compound of the present invention contains relatively acidic functional groups, the base addition salts thereof can be obtained by contacting the neutral form of such compound with a sufficient amount of base in a pure solution or suitable inert solvent. When the compound of the present invention contains relatively basic functional groups, the acid addition salts thereof can be obtained by contacting the neutral form of such compound with a sufficient amount of acid in a pure solution or suitable inert solvent. Pharmaceutically acceptable salts can be mentioned as metal salts, ammonium salts, salts formed with organic bases, salts formed with inorganic acids, salts formed with organic acids, salts formed with basic or acidic amino acids, etc.

Preferably, the salt is contacted with a base or acid in a conventional manner and the parent compound is then isolated, thereby regenerating the neutral form of the compound. The parent form of the compound differs from the various salt forms thereof in certain physical properties, for example, different solubilities in polar solvents.

Certain compounds of the present invention may have asymmetric carbon atoms (optical centers) or double bonds. Racemates, diastereomers, geometric isomers, and individual isomers are all included within the scope of the present invention.

The graphic representations of racemic, ambiscalemic and scalemic or enantiomerically pure compounds herein are from Maehr, J. Chem. Ed. 1985, 62: 114-120. Unless otherwise stated, the absolute configuration of a stereocenter is represented by solid and broken wedges. When the compounds described herein contain olefinic double bonds or other geometric asymmetrical centers, unless otherwise specified, they include E, Z geometric isomers. Likewise, all tautomeric forms are included within the scope of the present invention.

The compound of the present invention may exist in specific geometric or stereoisomeric forms. All such compounds envisaged by the present invention include cis and trans isomers, (−)- and (+)-enantiomer pairs, (R)- and (S)-enantiomers, diastereomers, (D)-isomers, (L)-isomers, and racemic mixtures and other mixtures thereof, such as enantiomers or diastereomers enriched mixtures, all of which fall within the scope of the present invention. Other asymmetric carbon atoms may be present in the substituents such as alkyl. All these isomers and their mixtures are included in the scope of the present invention.

The optically active (R)- and (S)-isomers as well as the D and L isomers can be prepared by chiral synthesis or chiral reagents or other conventional techniques. If an enantiomer of a certain compound of the present invention is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by a conventional method well known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compound of the present invention may contain non-natural proportions of atomic isotopes on one or more atoms which constitute the compound. For example, the compound may be labeled with a radioisotope, such as tritium ($^{3}H$), iodine-125 ($^{125}I$) or C-14 ($^{14}C$). Any isotopic composition transformations of the compound of the present invention, whether are radioactive or not, are included in the scope of the present invention.

The term "pharmaceutically acceptable carrier" refers to any formulation or carrier medium capable of delivering an effective amount of the active substance of the present invention, without interfering with the biological activity of the active substance and having no toxic side effects on the host or patient. Representative carriers include water, oils, vegetables and minerals, cream bases, lotion bases, ointment bases, etc. These bases include suspensions, tackifiers, transdermal enhancers, etc. Their formulations are well known to the skilled in the cosmetic field or topical drug field. Other information about carriers can refer to Remington: The Science and Practice of Pharmacy, $21^{st}$ Ed., Lippincott, Williams & Wilkins (2005), the contents of which are incorporated herein by reference.

The term "excipient" generally refers to the carrier, diluent and/or medium which is required to formulate an effective pharmaceutical composition.

For drugs or pharmacologically active agents, the term "effective amount" or "therapeutically effective amount" refers to a sufficient amount of a drug or agent that is non-toxic but can achieve the desired effect. For the oral dosage form of the present invention, the "effective amount" of one active substance in the composition means the amount needed to achieve the desired effect when used in combination with another active substance in the composition. The determination of the effective amount varies with each individual, depending on the age and general condition of the subject, as well as the specific active substance. The appropriate effective amount in each case can be determined by the skilled in the art according to a routine experiment.

The term "active ingredient", "therapeutic agent", "active substance" or "active agent" refers to a chemical entity that can effectively treat target disorders, diseases or conditions.

When the number of a linking group is 0, such as —$(CRR)_0$—, it means that the linking group is a single bond.

When a substituent is vacant, it means that the substituent does not exist. For example, when X is vacant in A-X, the structure is actually A. When a bond of one substituent can cross-link to two atoms on one ring, this substituent may be bonded to any atom on the ring. When it does not specify through which atom the listed substituent is linked to a compound included but not specifically mentioned in a chemical structure formula, this substituent may be bonded through any of its atoms. The combination of substituents and/or variants thereof is allowable only if such combination will result in stable compounds. For example, the structural unit

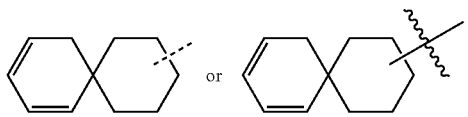

indicates that a substitution may occur at any position on cyclohexyl or cyclohexadiene.

Unless otherwise defined, the term "halogenated element" or "halogen" per se or as a part of another substituent denotes a fluorine, chlorine, bromine or iodine atom. Furthermore, the term "haloalkyl" is intended to include monohaloalkyl and polyhaloalkyl. For example, the term "halo $(C_1-C_4)$alkyl" is intended to include, but is not limited to, trifluoromethyl, 2,2,2-trifluoroethyl, 4-chlorobutyl, 3-bromopropyl, etc.

Examples of haloalkyl include, but are not limited to, trifluoromethyl, trichloromethyl, pentafluoroethyl, and pentachloroethyl. "Alkoxy" represents the above alkyl having a specific number of carbon atoms linked through an oxygen bridge. $C_{1-6}$ alkoxy includes $C_1$, $C_2$, $C_3$, $C_4$, $C_5$ and $C_6$ alkoxy. Examples of alkoxy include, but are not limited to, methoxy, ethoxy, n-propoxy, isopropoxy, n-butoxy, sec-butoxy, tert-butoxy, n-pentoxy and S-pentoxy. "Cycloalkyl" includes saturated ring groups, such as cyclopropyl, cyclobutyl or cyclopentyl. 3- to 7-membered cycloalkyl includes $C_3$, $C_4$, $C_5$, $C_6$ and $C_7$ cycloalkyl. "Alkenyl" includes a linear or branched hydrocarbon chain, in which one or more carbon-carbon double bonds are present at any stable site on the chain, for example, vinyl and propenyl.

The term "protecting group" includes, but is not limited to, "amino protecting group", "hydroxy protecting group" or "thiol protecting group". The term "amino protecting group" refers to a protecting group suitable for preventing side reactions on the nitrogen position of the amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; silyl, such as trimethylsilyl (TMS) and tert-butyldimethylsilyl (TBS), etc. The term "hydroxy protecting group" refers to protecting groups suitable for preventing side reactions of hydroxyl. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (benzhydryl, DPM); silyl, such as trimethylsilyl (TMS), tert-butyldimethylsilyl (TBS), etc. An important consideration factor in any synthetic route planning in the art is the selection of suitable protecting groups for reactive functional groups (such as amino in the present application). For trained practitioners, (Protective Groups In Organic Synthesis, Wiley and Sons, 1991) of Greene and Wuts is authoritative in this regard. All references cited in the present application are incorporated herein in their entirety.

The compound of the present invention can be prepared by a variety of synthetic methods well known by the skilled in the art, including the following exemplified embodiments, the embodiments formed by combining them with other chemical synthesis methods, and equivalent alternatives known to the skilled in the art. Preferred embodiments include, but are not limited to the examples of the present invention.

The solvents used in the present invention are commercially available. The present invention employs the following abbreviations: aq represents aqua; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent, equal quantity; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents carbobenzyloxy, which is an amine protecting group; BOC represents t-butyl carbonyl, which is an amine protecting group; HOAc represents acetic acid; $NaCNBH_3$ represents sodium cyanoborohydride; r.t. represents room temperature; 0/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(phenylsulfonyl)benzenesulfonamide; NC S represents 1-chloropyrrolidine-2,5-dione; $n$-$Bu_4NF$ represents tetrabutylammonium fluoride; iPrOH represents 2-propanol; mp represents melting point; LDA represents lithium diisopropylamide.

DETAILED DESCRIPTION OF THE INVENTION

In order to illustrate the present invention in more details, the following examples are given, but the scope of the present invention is not limited thereto.

Reference Example 1: Preparation of INT-747

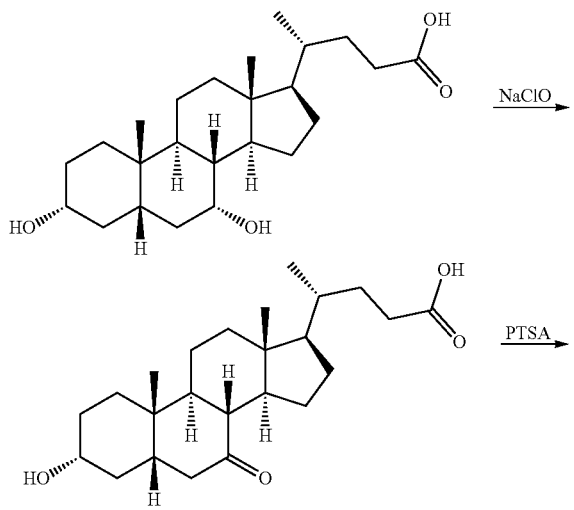

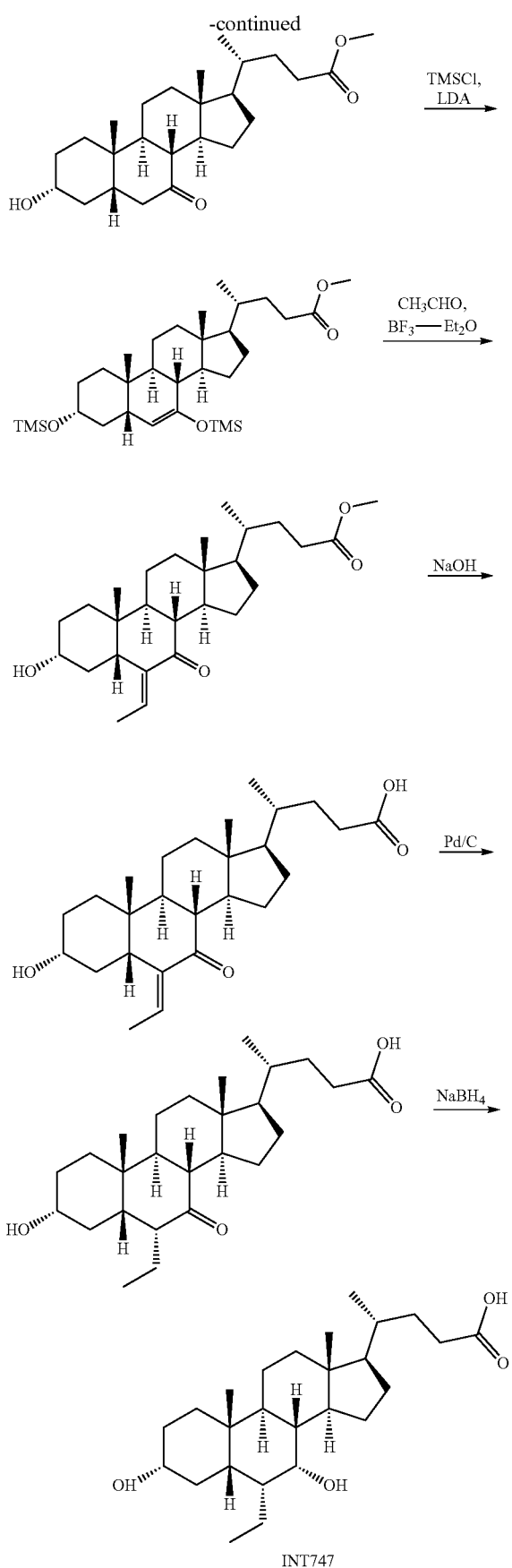

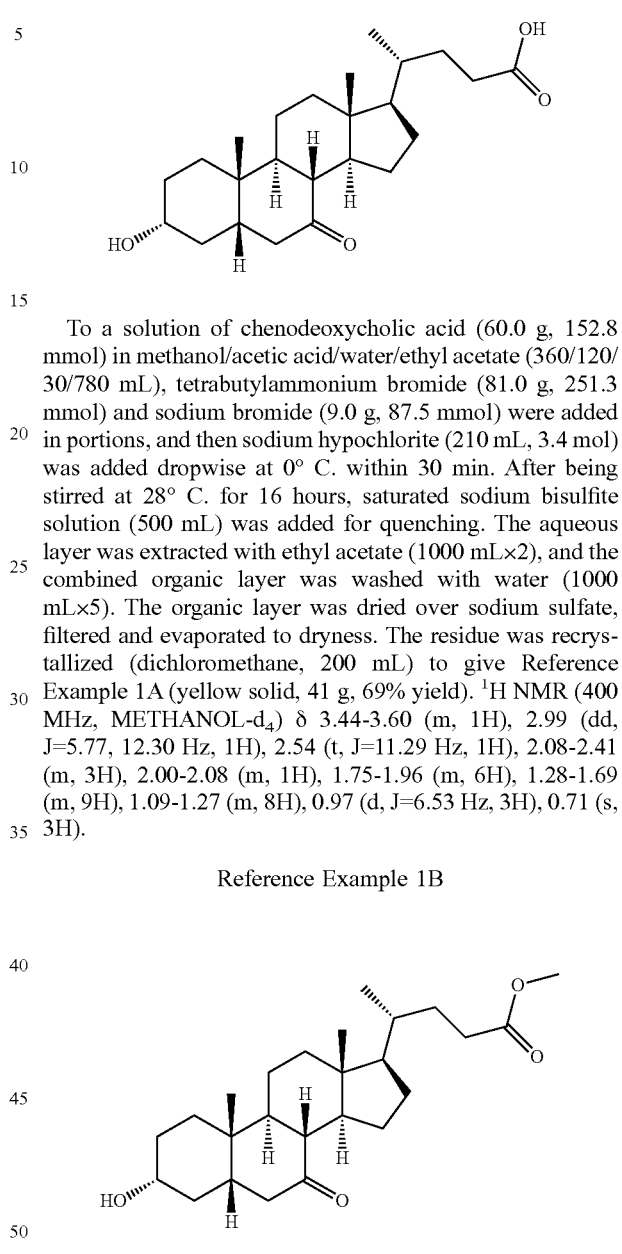

Reference Example 1A

To a solution of chenodeoxycholic acid (60.0 g, 152.8 mmol) in methanol/acetic acid/water/ethyl acetate (360/120/30/780 mL), tetrabutylammonium bromide (81.0 g, 251.3 mmol) and sodium bromide (9.0 g, 87.5 mmol) were added in portions, and then sodium hypochlorite (210 mL, 3.4 mol) was added dropwise at 0° C. within 30 min. After being stirred at 28° C. for 16 hours, saturated sodium bisulfite solution (500 mL) was added for quenching. The aqueous layer was extracted with ethyl acetate (1000 mL×2), and the combined organic layer was washed with water (1000 mL×5). The organic layer was dried over sodium sulfate, filtered and evaporated to dryness. The residue was recrystallized (dichloromethane, 200 mL) to give Reference Example 1A (yellow solid, 41 g, 69% yield). $^1$H NMR (400 MHz, METHANOL-$d_4$) δ 3.44-3.60 (m, 1H), 2.99 (dd, J=5.77, 12.30 Hz, 1H), 2.54 (t, J=11.29 Hz, 1H), 2.08-2.41 (m, 3H), 2.00-2.08 (m, 1H), 1.75-1.96 (m, 6H), 1.28-1.69 (m, 9H), 1.09-1.27 (m, 8H), 0.97 (d, J=6.53 Hz, 3H), 0.71 (s, 3H).

Reference Example 1B

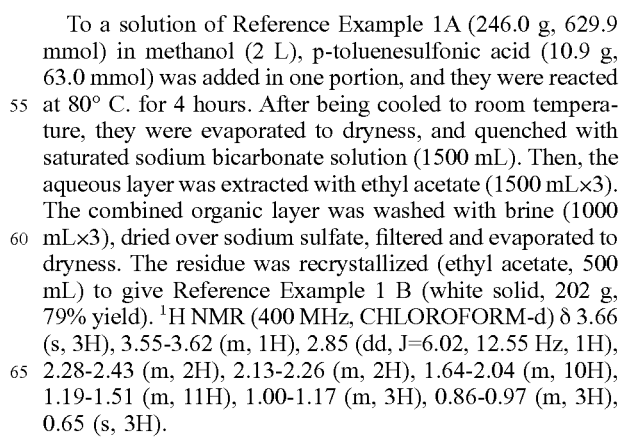

To a solution of Reference Example 1A (246.0 g, 629.9 mmol) in methanol (2 L), p-toluenesulfonic acid (10.9 g, 63.0 mmol) was added in one portion, and they were reacted at 80° C. for 4 hours. After being cooled to room temperature, they were evaporated to dryness, and quenched with saturated sodium bicarbonate solution (1500 mL). Then, the aqueous layer was extracted with ethyl acetate (1500 mL×3). The combined organic layer was washed with brine (1000 mL×3), dried over sodium sulfate, filtered and evaporated to dryness. The residue was recrystallized (ethyl acetate, 500 mL) to give Reference Example 1 B (white solid, 202 g, 79% yield). $^1$H NMR (400 MHz, CHLOROFORM-d) δ 3.66 (s, 3H), 3.55-3.62 (m, 1H), 2.85 (dd, J=6.02, 12.55 Hz, 1H), 2.28-2.43 (m, 2H), 2.13-2.26 (m, 2H), 1.64-2.04 (m, 10H), 1.19-1.51 (m, 11H), 1.00-1.17 (m, 3H), 0.86-0.97 (m, 3H), 0.65 (s, 3H).

Reference Example 1C

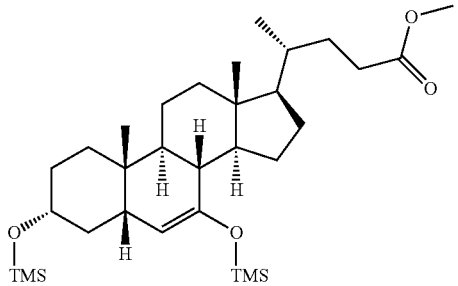

To a solution of chlorotrimethylsilane (107.5 g, 989.5 mmol) in tetrahydrofuran (500 mL), lithium diisopropylamide (87.4 g, 815.6 mmol) was added dropwise at −78° C. under nitrogen atmosphere, and after being stirred for 40 min, a solution of Reference Example 1B (50 g, 123.6 mmol) in tetrahydrofuran (300 mL) was further added dropwise. After completion of the dropwise addition, they were stirred at −78° C. for another 40 min, and then triethylamine (182.5 g, 1.8 mol) was added. They were quenched with saturated sodium hydrogencarbonate (1000 mL) after 1 hour, and the aqueous layer was extracted with ethyl acetate (1000 mL×3). The combined organic layer was further washed with water (100 mL×6) and saturated saline solution (1000 mL×2). The organic layer was dried over sodium sulfate, filtered and evaporated to dryness, so as to give Reference Example 1C (brown-yellow oil, 68 g, 100% yield), which can be directly used in the next step without further purification. $^1$H NMR (400 MHz, CHLOROFORM-d) δ 4.75 (dd, J=1.38, 5.90 Hz, 1H), 3.69 (s, 3H), 3.48-3.59 (m, 1H), 2.13-2.42 (m, 2H), 1.52-2.04 (m, 10H), 1.29-1.48 (m, 7H), 0.99-1.23 (m, 5H), 0.95 (d, J=6.53 Hz, 3H), 0.85 (s, 3H), 0.70 (s, 3H), 0.17-0.20 (m, 9H), 0.13 (s, 9H).

Reference Example 1D

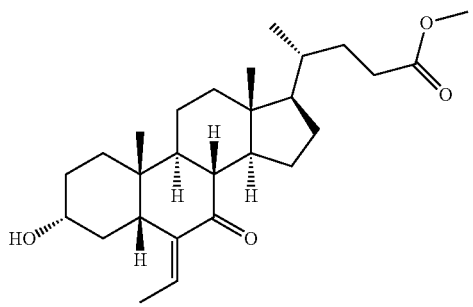

To a solution of Reference Example 1C (68.0 g, 123.9 mmol) in dichloromethane (500 mL), anhydrous acetaldehyde (10.1 g, 229.2 mmol) was added. A solution of boron trifluoride-diethyl ether (64.4 g, 453.4 mmol) in dichloromethane (300 mL) was added dropwise at −78° C. under nitrogen atmosphere. The dropping was required to be kept at an internal temperature of −78° C. After being stirred for 1 hour, it was warmed up to 30° C. and stirred for another 2 hours. The above solution was quenched with saturated sodium hydrogencarbonate (1000 mL). The aqueous layer was extracted with dichloromethane (1000 mL×3). The combined organic layer was washed with saturated saline solution (1000 mL×2), dried over sodium sulfate, filtered and evaporated to dryness. The residue was purified by column chromatography to give Reference Example 1D (yellow solid, 43 g, 81% yield). $^1$H NMR (400 MHz, CHLOROFORM-d) δ 6.12 (q, J=7.03 Hz, 1H), 3.52-3.66 (m, 4H), 2.54 (dd, J=4.02, 13.05 Hz, 1H), 2.13-2.40 (m, 5H), 1.68-1.98 (m, 7H), 1.65 (d, J=7.03 Hz, 3H), 1.00-1.52 (m, 11H), 0.97 (s, 3H), 0.89 (d, J=6.53 Hz, 3H), 0.61 (s, 3H).

Reference Example 1E

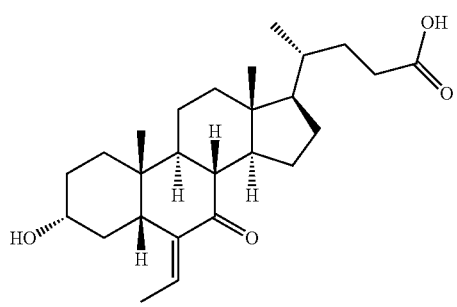

To a solution of Reference Example 1D (212.0 g, 492.3 mmol) in methanol (500 mL), a solution of NaOH (39.4 g, 984.6 mmol) in water (50 mL) was added, and they were stirred at 50° C. for 2 hours. After the solvent was evaporated to dryness, water (500 mL) was added, and ethyl acetate (500 mL×2) was employed for extracting. The aqueous phase was adjusted to pH 3 with dilute HCl, and extracted with dichloromethane (600 mL×2). The combined organic layer was concentrated. The residue was purified by recrystallization (ethanol, 200 mL) to give Reference Example 1E (yellow solid, 147 g, 72% yield). $^1$H NMR (400 MHz, CHLOROFORM-d) δ 6.19 (q, J=7.36 Hz, 1H), 3.60-3.74 (m, 1H), 2.58 (dd, J=4.02, 13.05 Hz, 1H), 2.40 (tt, J=5.02, 10.29 Hz, 3H), 2.19-2.32 (m, 2H), 1.61-2.06 (m, 10H), 1.04-1.54 (m, 14H), 1.01 (s, 3H), 0.95 (d, J=6.53 Hz, 3H), 0.65 (s, 3H).

Reference Example 1F

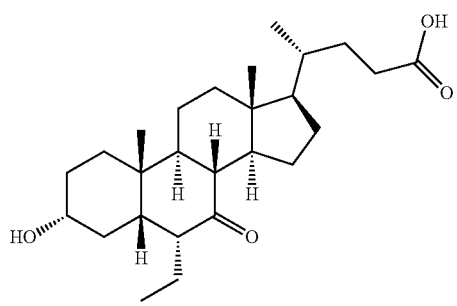

To a solution of Reference Example 1E (140.0 g, 336.1 mmol) in a solution of NaOH (0.5 mol) in water (600 mL), 10% Pd—C (19.9 g, 134.4 mmol) was added in one portion, and 15 psi of hydrogen was introduced, and they were reacted at 100° C. for 16 hours. After suction filtration, the filtrate was adjusted to pH 3 with dilute hydrochloric acid. The aqueous layer was extracted with dichloromethane (1500 mL×3). The combined organic layer was washed with brine (1000 mL×3), and dried over sodium sulfate, filtered and evaporated to dryness, so as to give Reference Example 1F (white solid, 101 g, 72% yield), which can be directly used in the next step without further purification. $^1$H NMR (400 MHz, CHLOROFORM-d) δ 3.49-3.60 (m, 1H), 2.70 (q, J=6.02 Hz, 1H), 2.12-2.45 (m, 4H), 1.65-2.02 (m, 9H), 1.29-1.52 (m, 6H), 1.05-1.24 (m, 8H), 0.93 (d, J=6.53 Hz, 5H), 0.81 (t, J=7.53 Hz, 3H), 0.66 (s, 3H).

Reference Compound INT-747

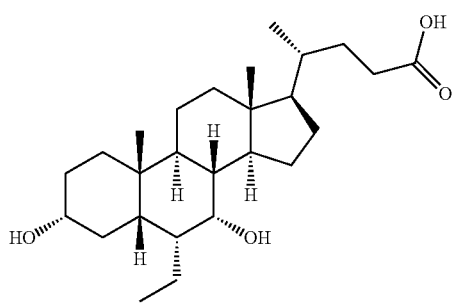

To a solution of Reference Example 1F (16.0 g, 38.2 mmol) in sodium hydroxide (2 mol, 100 mL), sodium borohydride (8.7 g, 229.3 mmol) was added in portions, and they were stirred at 100° C. for 2 hours. After being cooled to room temperature, saturated aqueous ammonium chloride solution (150 mL) was added. The pH thereof was adjusted to 3 with dilute hydrochloric acid. The aqueous layer was extracted with dichloromethane (300 mL×3). The combined organic layer were washed with brine (200 mL×3), dried over sodium sulfate, filtered and evaporated. The residue was purified by column chromatography, so as to give the reference compound INT-747 (white solid, 14.5 g, 90% yield). $^1$H NMR (400 MHz, CHLOROFORM-d) δ 3.71 (br. s, 1H), 3.36-3.48 (m, 1H), 2.18-2.47 (m, 2H), 1.56-2.01 (m, 10H), 1.06-1.54 (m, 15H), 0.86-0.97 (m, 9H), 0.66 (s, 3H).

Route 1

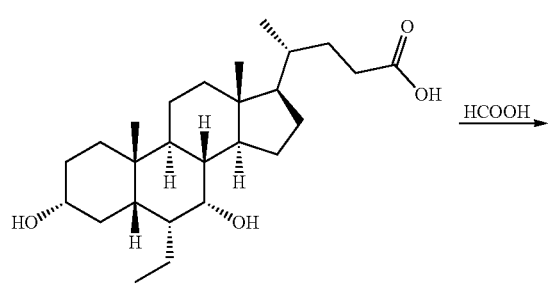

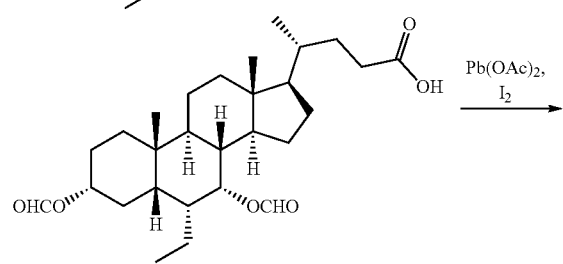

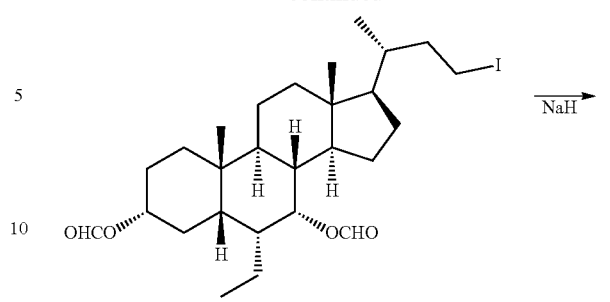

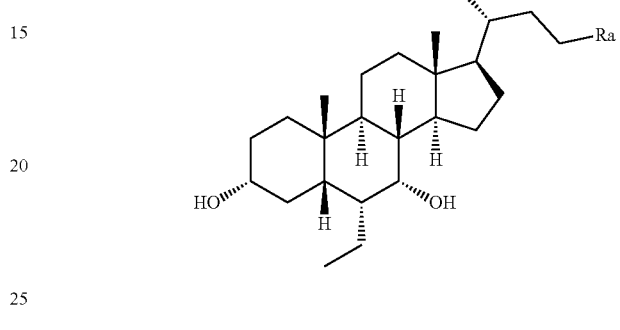

Ra =

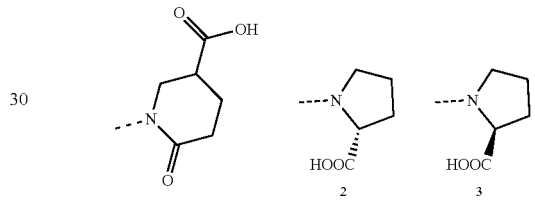

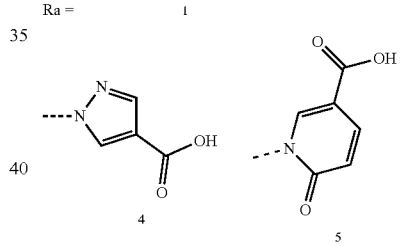

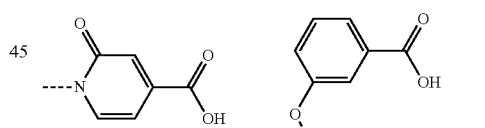

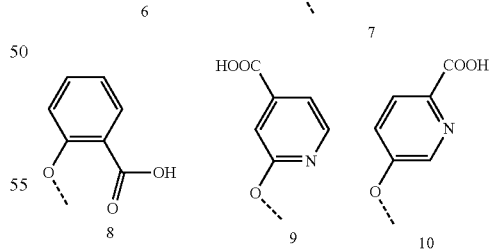

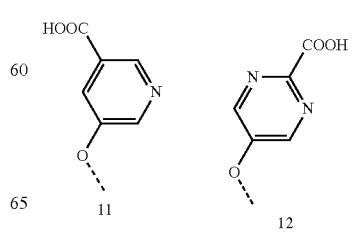

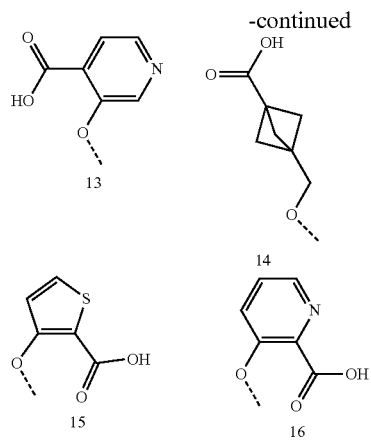

13 14 15 16

Example 1

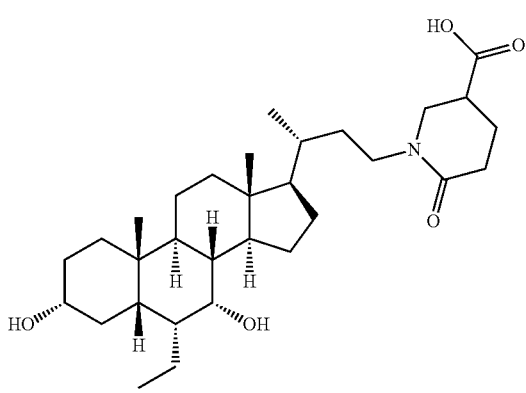

Example 1A

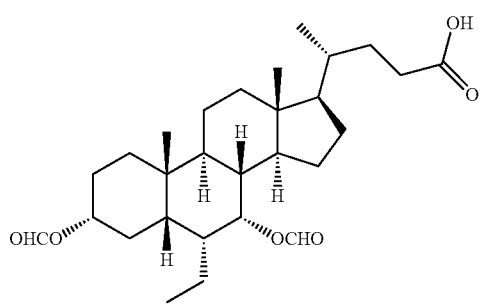

To a solution of the reference compound INT-747 (2.7 g, 6.4 mmol) and formic acid (0.3 g, 6.4 mmol) in tetrahydrofuran (40 mL), perchloric acid (6.0 g, 60.0 mmol) was added under nitrogen atmosphere. After being stirred at 55° C. for 6 hours and concentrated under vacuum, the above solution was diluted with water (100 mL). The aqueous layer was extracted with ethyl acetate (100 mL×2). The combined organic layer was dried over anhydrous sodium sulfate, filtered and evaporated to dryness. The residue was purified by column chromatography, so as to give Example 1 A as a white solid (2.8 g, 92% yield). NMR (400 MHz, CHLO-ROFORM-d) δ 8.16 (s, 1H), 8.05 (s, 1H), 5.20 (br. s., 1H), 4.77-4.65 (m, 1H), 2.45-2.34 (m, 1H), 2.31-2.21 (m, 1H), 2.01-1.58 (m, 11H), 1.55-1.30 (m, 8H), 1.22-1.05 (m, 6H), 0.97-0.88 (m, 9H), 0.66 (s, 3H).

Example 1B

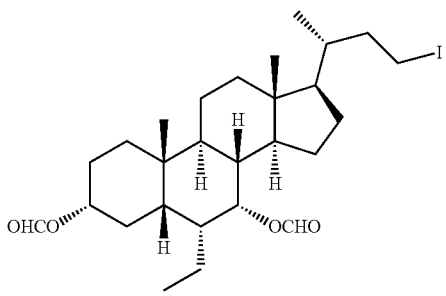

To a solution of Example 1A (100.0 mg, 0.2 mmol) and lead acetate (186.0 mg, 0.4 mmol) in carbon tetrachloride (2 mL), iodine (106.0 mg, 0.4 mmol) was added, and the reaction system was reacted for 12 hours under light irradiation. The reaction of the above solution was quenched by adding a solution of sodium thiosulfate (1 mL). The aqueous layer was extracted with dichloromethane (10 mL×3), dried over anhydrous sodium sulfate, filtered and evaporated to dryness. The residue was purified by a preparative thin layer plate (petroleum ether:ethyl acetate=5:1), so as to give Example 1B (colorless solid, 50.0 mg, 38% yield). ¹H-NMR (CDCl₃, 400 MHz) δ 8.14 (s, 1H), 8.03 (s, 1H), 5.19 (br. s., 1H), 4.62-4.77 (m, 1H), 3.23-3.32 (m, 1H), 3.00-3.12 (m, 1H), 1.96-2.02 (m, 2H), 1.85-1.92 (m, 2H), 1.70-1.82 (m, 7H), 1.66-1.72 (m, 2H), 1.39-1.45 (m, 2H), 1.23-1.32 (m, 5H), 1.09-1.19 (m, 6H), 0.96 (s, 3H), 0.90-0.93 (m, 6H), 0.67 (s, 3H).

Example 1

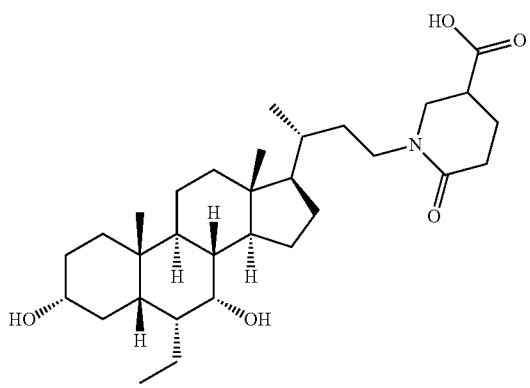

To a solution of methyl 6-oxopiperidine-3-carboxylate (21.0 mg, 134 μmol) in N,N-dimethylformamide (1 mL), sodium hydrogen (7.0 mg, 179 μmol, 60%) was added. After half an hour, a solution of Example 1B (50.0 mg, 89.5 μmol) in N,N-dimethylformamide (1 mL) was slowly added dropwise at 0° C. After the dropwise addition was completed, the reaction system was slowly warmed up to room temperature, and reacted for 12 hours. Water (3 mL) and lithium hydroxide monohydrate (4 mg, 89.5 mmol) were added to the reaction system, and it was stirred for another 3 hours. Water (10 mL) was added, and the reaction system was adjusted to pH=6 with hydrochloric acid (1M), extracted with dichloromethane:methanol=10:1 (10 mL×3). The organic layer was dried over anhydrous sodium sulfate, filtered, and evaporated to dryness. The residue was purified by preparative thin layer plate (dichloromethane:methanol=10:1), so as to give Example 1 (15 mg, 32.4% yield). $^1$H NMR (400 MHz, METHANOL-$d_4$) δ 3.67 (br. s., 1H), 3.58-3.48 (m, 2H), 3.45-3.34 (m, 2H), 3.31-3.27 (m, 1H), 2.87 (d, J=13.1 Hz, 1H), 2.49-2.29 (m, 2H), 2.11 (br. s., 2H), 2.00-1.35 (m, 19H), 1.30-1.10 (m, 6H), 1.04 (d, J=6.5 Hz, 3H), 0.95-0.90 (m, 6H), 0.72 (s, 3H).

Example compounds 2-16 were synthesized via the same procedure as Example 1, and shown as follows:

| Compound No. | Yield % | Compound structure | $^1$H NMR |
|---|---|---|---|
| Example 2 | 6% | | $^1$H NMR (400 MHz, CHLOROFORM-d) δ 3.97-3.88 (m, 1H), 3.77-3.66 (m, 2H), 3.47-3.37 (m, 1H), 3.17-3.04 (m, 1H), 2.83 (q, J = 9.1 Hz, 1H), 2.37-2.31 (m, 2H), 2.08 (d, J = 12.8 Hz, 7H), 1.93-1.79 (m, 4H), 1.69-1.45 (m, 7H), 1.23-1.11 (m, 4H), 1.00 (d, J = 4.5 Hz, 3H), 0.92-0.90 (m, 8H), 0.88 (d, J = 2.0 Hz, 4H), 0.68 (s, 3H) |
| Example 3 | 6% | | $^1$H NMR (400 MHz, CHLOROFORM-d) δ 4.03-3.91 (m, 1H), 3.73 (t, J = 7.2 Hz, 1H), 3.68 (br. s., 1H), 3.41 (d, J = 4.8 Hz, 1H), 3.25-3.16 (m, 1H), 3.05 (br. s., 1H), 2.87-2.80 (m, 1H), 2.39-2.25 (m, 2H), 2.06-1.95 (m, 2H), 1.92-1.77 (m, 6H), 1.77-1.76 (m, 1H), 1.72-1.56 (m, 4H), 1.50 (d, J = 5.0 Hz, 3H), 1.44 (d, J = 12.3 Hz, 3H), 1.19-1.11 (m, 4H), 1.06-1.00 (m, 1H), 0.96 (d, J = 4.5 Hz, 3H), 0.91-0.89 (m, 1H), 0.90 (br. s., 3H), 0.88 (br. s., 2H), 0.86 (d, J = 2.5 Hz, 4H), 0.84 (d, J = 3.0 Hz, 2H), 0.68-0.62 (m, 3H) |
| Example 4 | 52.7% | | $^1$H NMR (400 MHz, CHLOROFORM-d) δ 7.96 (s, 1H), 7.93 (s, 1H), 4.26-4.16 (m, 1H), 4.15-4.06 (m, 1H), 3.70 (br. s., 1H), 3.46-3.33 (m, 1H), 2.10-2.02 (m, 1H), 1.99-1.86 (m, 2H), 1.84-1.77 (m, 3H), 1.71-1.56 (m, 4H), 1.50-1.40 (m, 5H), 1.34-1.30 (m, 2H), 1.26 (s, 3H), 1.22-1.17 (m, 3H), 1.01 (d, J = 6.5 Hz, 4H), 0.92 (s, 1H), 0.89 (s, 3H), 0.88-0.85 (m, 2H), 0.64 (s, 3H) |
| Example 5 | 57% | | $^1$H NMR (400 MHz, METHANOL-$d_4$) δ 8.40 (s, 1H), 7.97 (dd, J = 2.0, 9.5 Hz, 1H), 6.54 (d, J = 9.5 Hz, 1H), 4.20-3.98 (m, 2H), 3.67 (br. s., 1H), 3.32-3.28 (m, 1H), 2.05-1.73 (m, 8H), 1.63-1.21 (m, 16H), 1.12 (d, J = 6.0 Hz, 3H), 1.07-0.99 (m, 1H), 0.95-0.90 (m, 6H), 0.71 (s, 3H). |

-continued

| Compound No. | Yield % | Compound structure | ¹H NMR |
|---|---|---|---|
| Example 6 | 10.9% | | ¹H NMR (400 MHz, METHANOL-d₄) δ 7.66 (d, J = 5.0 Hz, 1H), 7.15-6.97 (m, 1H), 6.82 (br. s., 1H), 3.32-3.29 (m, 1H), 2.04-1.25 (m, 25H), 1.26-1.25 (m, 1H), 1.11 (d, J = 6.0 Hz, 3H), 0.95-0.89 (m, 6H), 0.70 (s, 3H). |
| Example 7 | 53% | | ¹H NMR (400 MHz, METHANOL-d₄) δ 0.75 (s, 3 H) 0.87-0.97 (m, 6 H) 1.07 (d, J = 6.53 Hz, 3 H) 1.12-2.11 (m, 25 H) 3.27-3.32 (m, 1 H) 3.69 (br. s., 1 H) 4.01-4.17 (m, 2 H) 7.16 (dd, J = 8.16, 2.13 Hz, 1 H) 7.38 (t, J = 7.91 Hz, 1 H) 7.54 (s, 1 H) 7.61 (d, J = 7.53 Hz, 1 H). |
| Example 8 | 16% | | ¹H NMR (400 MHz, METHANOL-d₄) δ 0.74 (s, 3 H) 0.90-0.96 (m, 6 H) 1.06 (d, J = 6.53 Hz, 3 H) 1.21-2.13 (m, 25 H) 3.31 (br. s., 1 H) 3.68 (br. s., 1 H) 4.07-4.27 (m, 2 H) 7.03 (t, J = 7.53 Hz, 1 H) 7.15 (d, J = 8.53 Hz, 1 H) 7.46-7.66 (m, 1 H) 7.82 (dd, J = 7.78, 1.25 Hz, 1 H). |
| Example 9 | 10.9% | | ¹H NMR (400 MHz, CD₃OD) δ 8.71 (br. s., 1H), 8.37 (br. s., 1H), 7.89 (br. s., 1H), 4.16 (d, J = 6.8 Hz, 2H), 3.67 (br. s., 1H), 3.37 (s, 1H), 2.01-1.20 (m, 25H), 1.06 (d, J = 6.5 Hz, 3H), 0.94-0.90 (m, 6H), 0.73 (s, 3H). |
| Example 10 | 16% | | ¹H NMR (400 MHz, METHANOL-d₄) δ 8.57 (br. s., 1H), 8.47 (d, J = 8.3 Hz, 1H), 8.19 (d, J = 8.0 Hz, 1H), 4.37 (d, J = 5.3 Hz, 2H), 3.68 (br. s., 1H), 3.37 (s, 1H), 2.03-1.28 (m, 25H), 1.10 (d, J = 6.3 Hz, 3H), 0.95-0.91 (m, 6H), 0.75 (s, 3H). |

| Compound No. | Yield % | Compound structure | ¹H NMR |
|---|---|---|---|
| Example 11 | 72% | 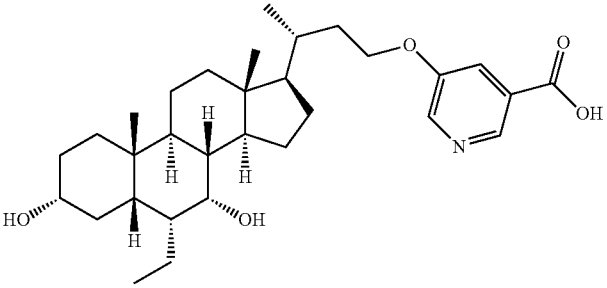 | ¹H NMR (400 MHz, METHANOL-$d_4$) δ 8.71 (br. s., 1H), 8.37 (br. s., 1H), 7.89 (br. s., 1H), 4.16 (d, J = 6.8 Hz, 2H), 3.67 (br. s., 1H), 3.37 (s, 1H), 2.01-1.20 (m, 25H), 1.06 (d, J = 6.5 Hz, 3H), 0.94-0.90 (m, 6H), 0.73 (s, 3H). |
| Example 12 | 61% | 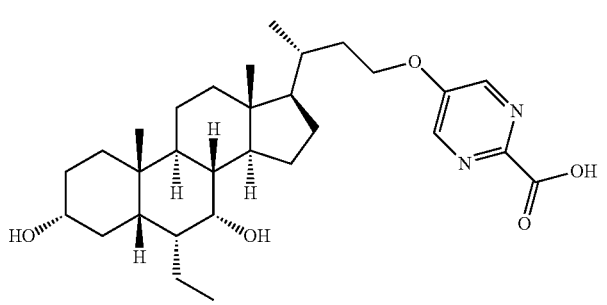 | ¹H NMR (400 MHz, METHANOL-$d_4$) δ 8.62 (s, 2H), 4.38-4.26 (m, 2H), 3.68 (br. s., 1H), 3.31-3.25 (m, 1H), 2.13-1.67 (m, 9H), 1.65-1.14 (m, 15H), 1.12-0.98 (m, 4H), 0.96-0.89 (m, 6H), 0.75 (s, 3H). |
| Example 13 | 31% | 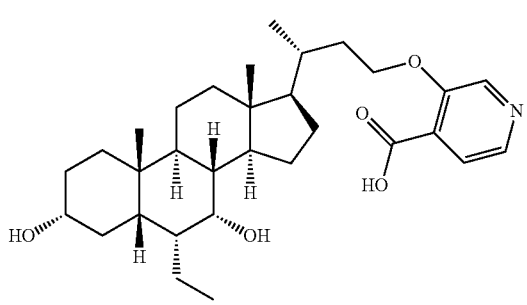 | ¹H NMR (400 MHz, METHANOL-$d_4$) δ 8.40 (s, 1H), 8.22 (br. s., 1H), 7.52 (br. s., 1H), 4.22 (dd, J = 7.5, 15.8 Hz, 2H), 3.68 (br. s., 1H), 3.35-3.34 (m, 1H), 2.01-1.37 (m, 25H), 1.06 (d, J = 6.3 Hz, 3H), 0.94-0.89 (m, 6H), 0.74 (s, 3H). |
| Example 14 | 16% | 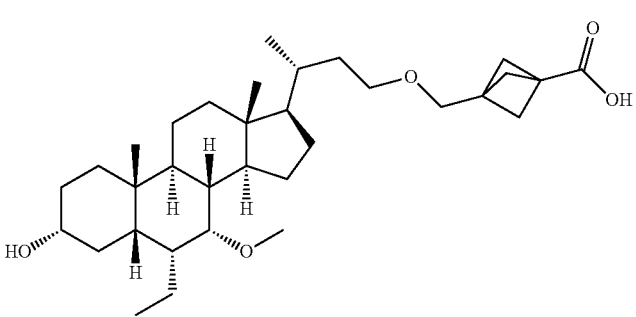 | ¹H NMR (400 MHz, METHANOL-$d_4$) δ 3.72-3.63 (m, 3H), 3.54-3.39 (m, 4H), 2.26 (s, 3H), 1.96 (s, 3H), 1.88-1.04 (m, 25H), 0.99-0.87 (m, 9H), 0.70 (s, 3H) |
| Example 15 | 75% | 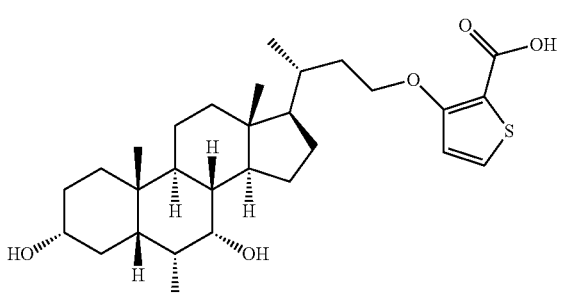 | ¹H NMR (400 MHz, METHANOL-$d_4$) δ 7.67-7.48 (m, 1H), 7.06-6.94 (m, 1H), 4.34-4.12 (m, 2H), 3.66 (br s, 1H), 3.30-3.26 (m, 1H), 2.06-1.14 (m, 25H), 1.04 (d, J = 6.5 Hz, 3H), 0.94-0.86 (m, 6H), 0.72 (s, 3H) |

-continued
| Compound No. | Yield % | Compound structure | ¹H NMR |
|---|---|---|---|
| Example 16 | 34% | | ¹H NMR (400 MHz, METHANOL-d₄) δ 8.40 (s, 1H), 8.22 (br s, 1H), 7.52 (br s, 1H), 4.22 (br dd, J = 7.5, 15.8 Hz, 2H), 3.68 (br s, 1H), 3.35-3.34 (m, 1H), 2.01-1.37 (m, 25H), 1.06 (br d, J = 6.3 Hz, 3H), 0.94-0.89 (m, 6H), 0.74 (s, 3H) |
Route 2
Example 17 and Example 18
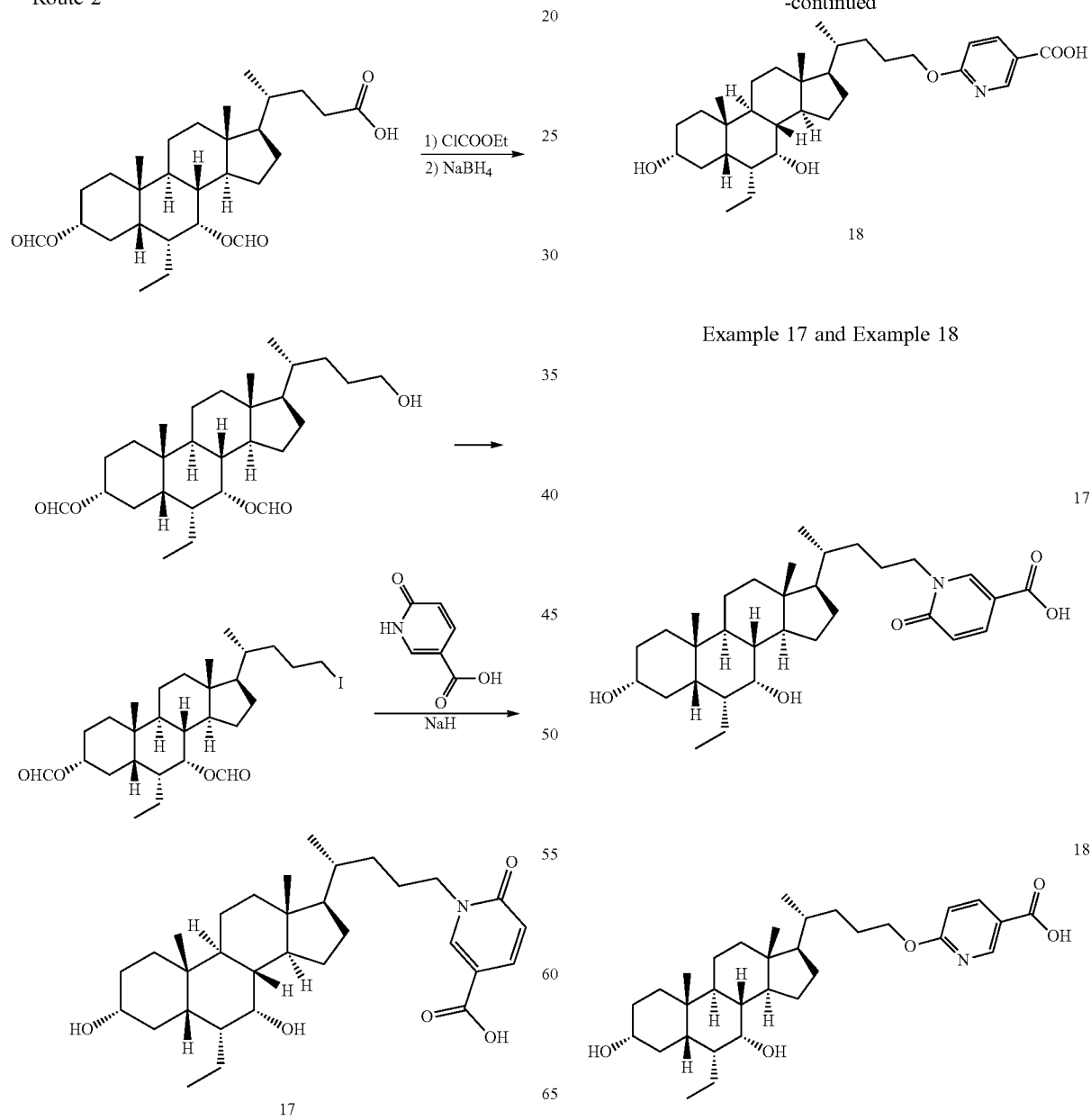

Example 2A

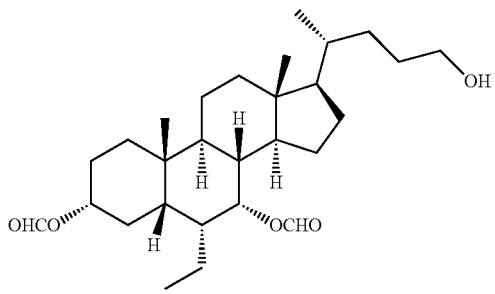

To a solution of Example 1A (500.0 mg, 1 mmol) in tetrahydrofuran (5 mL), triethylamine (153.0 mg, 1.5 mmol) and ethyl chloroformate (167.0 mg, 1.5 mmol) were added, and the reaction system was reacted at 25° C. for 2 hours. The system was cooled to 0° C., and a solution of sodium borohydride (210.0 mg, 5.6 mmol) in methanol (5 mL) was slowly added to the reaction system, and they were reacted at 0° C. for 15 min, and further reacted at 25° C. for 15 min. The reaction was quenched with 0.2 M dilute hydrochloric acid (1 mL). The aqueous layer was extracted with ethyl acetate (10 mL×3). The organic layer was dried over anhydrous sodium sulfate, filtered and evaporated to dryness. The residue was purified by column chromatography (petroleum ether:ethyl acetate=4:1), so as to give Example 2A (250.0 mg, 70%). $^1$H NMR (400 MHz, CHLOROFORM-d) δ 8.15 (s, 1H), 8.04 (s, 1H), 5.19 (br. s., 1H), 4.77-4.66 (m, 1H), 3.66-3.57 (m, 2H), 2.06-1.77 (m, 7H), 1.45-1.06 (m, 21H), 0.97-0.88 (m, 9H), 0.66 (s, 3H).

Example 2B

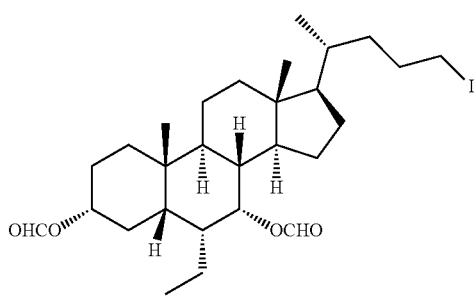

To a mixed solution of Example 2A (280.0 mg, 605 μmol), triphenylphosphine (476.0 mg, 1.8 mmol) and imidazole (124.0 mg, 1.8 mmol) in toluene (4 mL) and acetonitrile (1 mL), iodine (461.0 mg, 1.8 mmol) was added, and the reaction system was reacted at 25° C. for 3 hours. A solution of saturated sodium sulfite (10 mL) was added to the reaction system, and the aqueous layer was extracted with ethyl acetate (10 mL×3). The organic layers were combined and dried over anhydrous sodium sulfate, filtered, and evaporated to dryness. The residue was purified by column chromatography (petroleum ether:ethyl acetate=20:1), so as to give Example 2B (250.0 mg, 70%). $^1$H-NMR (CDCl$_3$, 400 MHz) □δ 8.16 (s, 1H), 8.07-8.02 (m, 1H), 5.20 (br. s., 1H), 4.76-4.66 (m, 1H), 3.24-3.08 (m, 2H), 2.01-1.72 (m, 10H), 1.46-1.06 (m, 17H), 0.97-0.89 (m, 9H), 0.66 (s, 3H).

Example 17 and Example 18

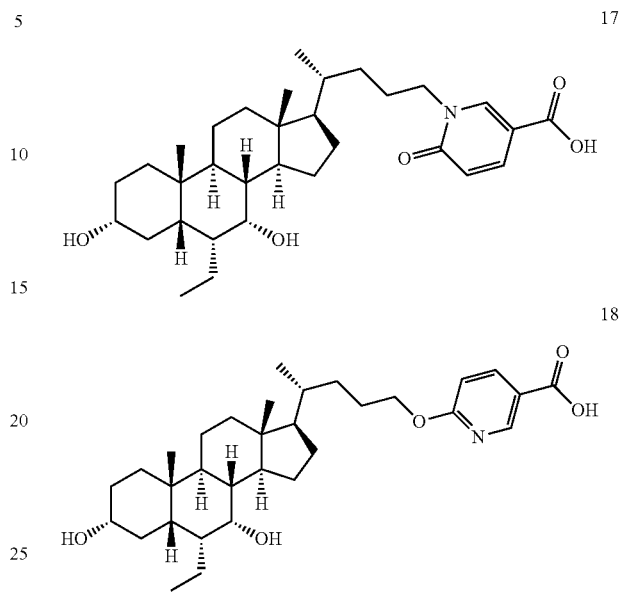

To a solution of methyl 6-hydroxynicotinate (80.0 mg, 523 μmop in N,N-dimethylformamide (3 mL), sodium hydrogen (21.0 mg, 523 mmol, 60%) was added at 0° C. After half an hour, a solution of Example 2B (150.0 mg, 262 μmop in N,N-dimethylformamide (5 mL) was added dropwise at 0° C. After the dropwise addition was completed, the reaction system was slowly warmed up to room temperature, and reacted for 12 hours. Water (3 mL) and lithium hydroxide monohydrate (55 mg, 1.31 mmol) were added to the reaction system, and stirred for another 3 hours. Water (10 mL) was added, and the system was adjusted to pH=6 with hydrochloric acid (1M), extracted with dichloromethane:methanol=10:1 (10 mL×3). The organic layer was dried over anhydrous sodium sulfate, filtered and evaporated to dryness. The residue was isolated and purified by a preparative thin layer plate (dichloromethane:methanol=10:1), so as to give Example 17 (40 mg, 29%), $^1$H NMR (400 MHz, METHANOL-d$_4$) δ 8.44 (d, J=2.5 Hz, 1H), 7.97 (dd, J=2.5, 9.5 Hz, 1H), 6.55 (d, J=9.5 Hz, 1H), 4.10-3.96 (m, 2H), 3.70-3.63 (m, 1H), 3.37-3.34 (m, 1H), 2.02-1.11 (m, 27H), 0.98 (d, J=6.0 Hz, 3H), 0.95-0.88 (m, 6H), 0.71 (s, 3H); and Example 18 (20 mg, 14%), $^1$H NMR (400 MHz, METHANOL-d$_4$) δ 8.77 (s, 1H), 8.21 (dd, J=1.8, 8.8 Hz, 1H), 6.84 (d, J=8.5 Hz, 1H), 4.34 (d, J=2.5 Hz, 2H), 3.78-3.58 (m, 1H), 3.38-3.33 (m, 1H), 2.02-1.22 (m, 27H), 1.01 (d, J=6.5 Hz, 3H), 0.95-0.90 (m, 6H), 0.72 (s, 3H).

Route 3

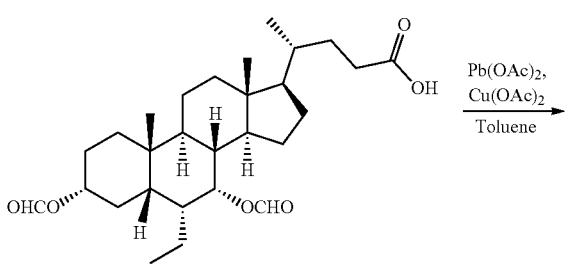

Example 3A

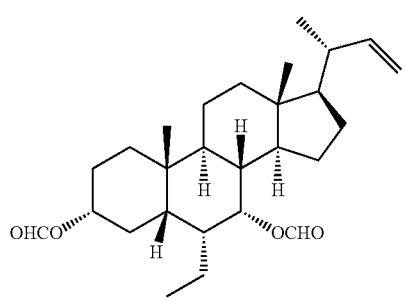

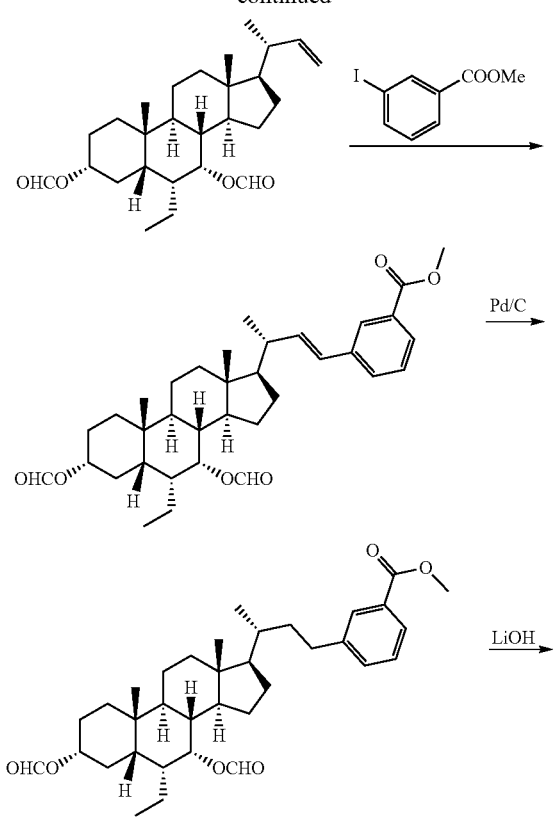

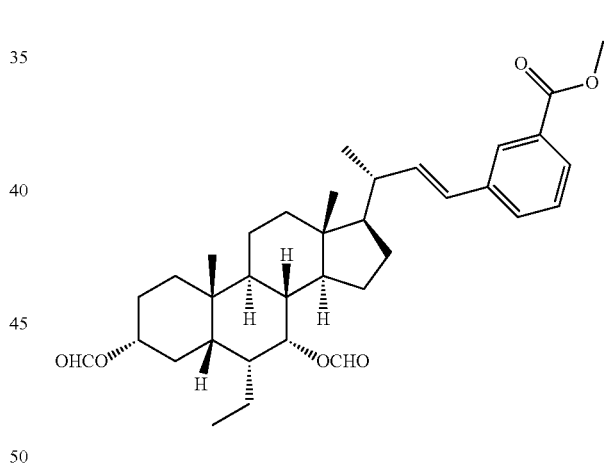

To a solution of Example 2A (500.0 mg, 1.1 mmol), copper acetate (99.0 mg, 0.6 mmol) and lead acetate (2.4 g, 11.0 mmol) in toluene (5 mL), pyridine (980.0 mg, 12.4 mmol) was added, and the reaction system was reacted at 110° C. for 12 hours. The reaction system was filtered, and the filtrate was concentrated. The residue was purified by column chromatography (petroleum ether:ethyl acetate=20:1), so as to give the title compound (120.0 mg, 27.0%). $^1$H NMR (400 MHz, CHLOROFORM-d) δ 8.15 (s, 1H), 8.05 (s, 1H), 5.71-5.59 (m, 1H), 5.19 (br. s., 1H), 4.93-4.80 (m, 2H), 4.76-4.67 (m, 1H), 2.12-1.61 (m, 11H), 1.52-1.09 (m, 13H), 1.04 (d, J=6.8 Hz, 3H), 0.97 (s, 3H), 0.91 (t, J=7.4 Hz, 3H), 0.68 (s, 3H).

Example 313

19

Example 19

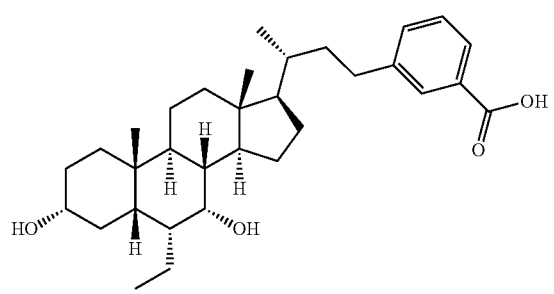

To a solution of Example 3A (100.0 mg, 0.2 mmol), sodium carbonate (74.0 mg, 0.7 mmol) and tetrabutylammonium bromide (66.0 mg, 0.2 mmol) in N,N-dimethylformamide (2 mL), palladium acetate (5.0 mg, 23.0 μmop and methyl 2-iodobenzoate (60.8 mg, 0.2 mmol) were added under nitrogen, and the reaction system was reacted at 85° C. for 12 hours. The solvent was evaporated to dryness and water (10 mL) was added to the reaction system. The aqueous layer was extracted with dichloromethane (20 mL×3). The organic layers were combined. The organic phase was dried over anhydrous sodium sulfate, filtered and evaporated to dryness. The residue was purified by preparative thin layer chromatography (petroleum ether:ethyl acetate=10:1), so as to give the title compound (80.0 mg, 61.0%).

$^1$H NMR (400 MHz, CHLOROFORM-d) δ 8.16 (s, 1H), 8.07 (s, 1H), 8.01 (s, 1H), 7.90-7.84 (m, 1H), 7.51 (d, J=7.8

Hz, 1H), 7.41-7.33 (m, 1H), 6.40-6.31 (m, 1H), 6.16 (dd, J=8.8, 15.8 Hz, 1H), 5.21 (br. s., 1H), 4.79-4.63 (m, 1H), 3.94 (s, 3H), 2.29 (d, J=6.8 Hz, 1H), 2.08-1.62 (m, 11H), 1.52-1.20 (m, 11H), 1.15 (d, J=6.5 Hz, 3H), 1.00 (s, 3H), 0.95-0.90 (m, 3H), 0.74 (s, 3H).

Example 3C

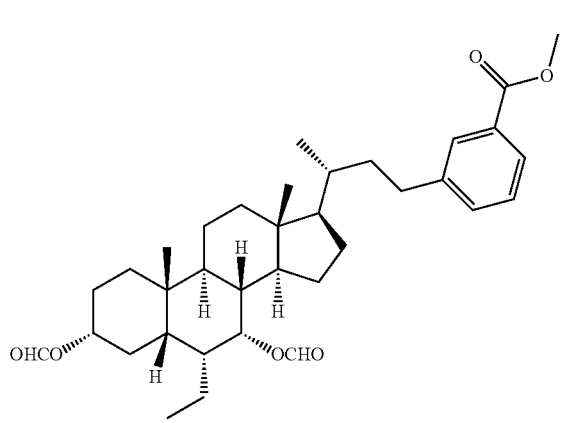

To a solution of Example 3B (100.0 mg, 0.2 mmol) in methanol (3 mL), wet palladium on carbon (50 mg, 10%) was added under nitrogen, and the reaction system was reacted under hydrogen condition (15 psi) at 25° C. for 12 hours. The reaction system was filtered and evaporated to dryness, so as to give Example 3C (90.0 mg, 90.0%). $^1$H NMR (400 MHz, CHLOROFORM-d) δ 8.18-8.11 (m, 1H), 8.06-8.00 (m, 1H), 7.85-7.81 (m, 2H), 7.35-7.31 (m, 2H), 5.18 (br. s., 1H), 4.76-4.51 (m, 1H), 2.77-2.64 (m, 1H), 2.54-2.44 (m, 1H), 1.95-1.20 (m, 25H), 1.01 (d, J=6.5 Hz, 3H), 0.95-0.87 (m, 6H), 0.64 (s, 3H).

Example 19

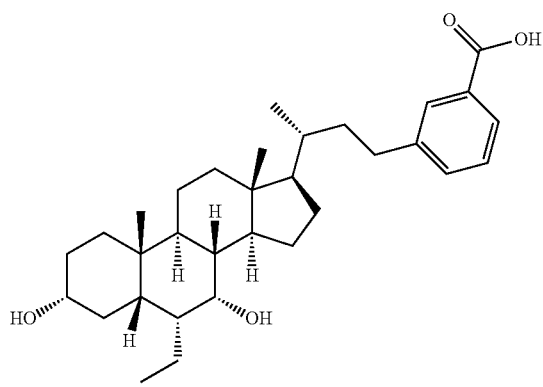

To a solution of Example 3C (160.0 mg, 282.0 μmol) in tetrahydrofuran (1 mL), methanol (1 mL) and water (1 mL), lithium hydroxide (59.0 mg, 1.4 mmol) was added. The reaction system was reacted at 20° C. for 12 hours. Water (5 mL) was added to the reaction system, and the system was adjusted to pH=1-2 with hydrochloric acid (1 M). The aqueous phase was extracted with ethyl acetate (10 mL×3). The organic layers were combined and dried over anhydrous sodium sulfate, filtered and evaporated to dryness. The residue was isolated and purified by preparative isolation (HCl), so as to give Example 19 (80 mg, 57%). $^1$H NMR (400 MHz, METHANOL-d$_4$) δ 7.93-7.76 (m, 2H), 7.45-7.35 (m, 2H), 3.67 (br. s., 1H), 3.37-3.35 (m, 1H), 2.84-2.73 (m, 1H), 2.60 (d, J=10.5 Hz, 1H), 2.06-1.27 (m, 25H), 1.09 (d, J=6.3 Hz, 3H), 0.94-0.91 (m, 6H), 0.70 (s, 3H).

Route 4

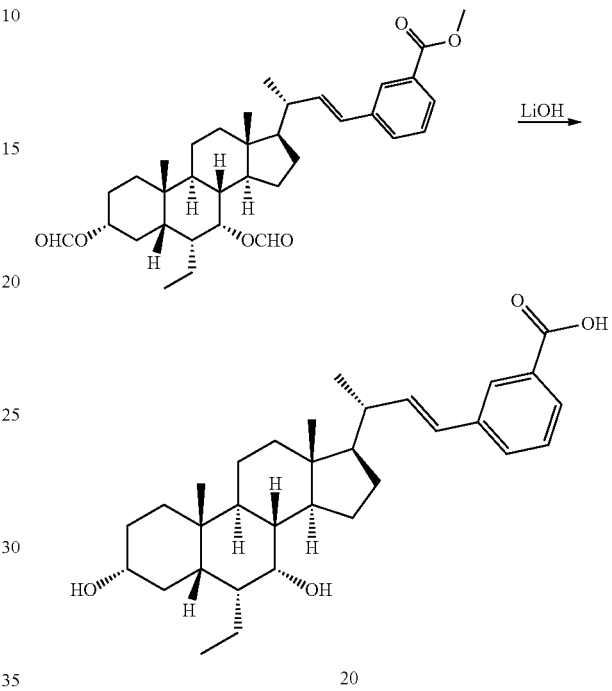

Example 20

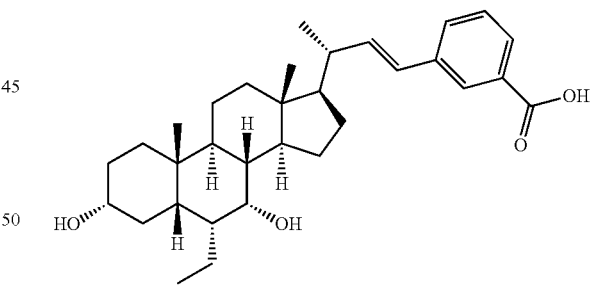

To a solution of Example 3B (40.0 mg, 70.8 μmop in tetrahydrofuran (0.5 mL), methanol (0.5 mL) and water (0.5 mL), lithium hydroxide (15 mg, 0.35 mmol) was added. The reaction system was reacted at 20° C. for 12 hours. Water (5 mL) was added to the reaction system, and the system was adjusted to pH=1-2 with hydrochloric acid (1 M). The aqueous phase was extracted with ethyl acetate (10 mL×3). The organic layers were combined and dried over anhydrous sodium sulfate, filtered and evaporated to dryness. The residue was purified by preparative thin layer chromatography (dichloromethane:methanol=10:1), so as to give Example 20 (25.0 mg, 71.0%). $^1$H NMR (400 MHz, METHANOL-d$_4$) δ 8.00 (br. s., 1H), 7.84 (d, J=7.0 Hz, 1H), 7.55 (d, J=7.5 Hz, 1H), 7.42-7.34 (m, 1H), 6.46-6.32 (m, 1H), 6.19 (dd, J=8.8, 15.6 Hz, 1H), 3.72-3.62 (m, 1H), 3.39-3.37 (m, 1H), 2.32 (d, J=6.0 Hz, 1H), 2.07-1.29 (m, 22H), 1.17 (d, J=6.3 Hz, 3H), 0.95-0.89 (m, 6H), 0.78 (s, 3H).

Route 5

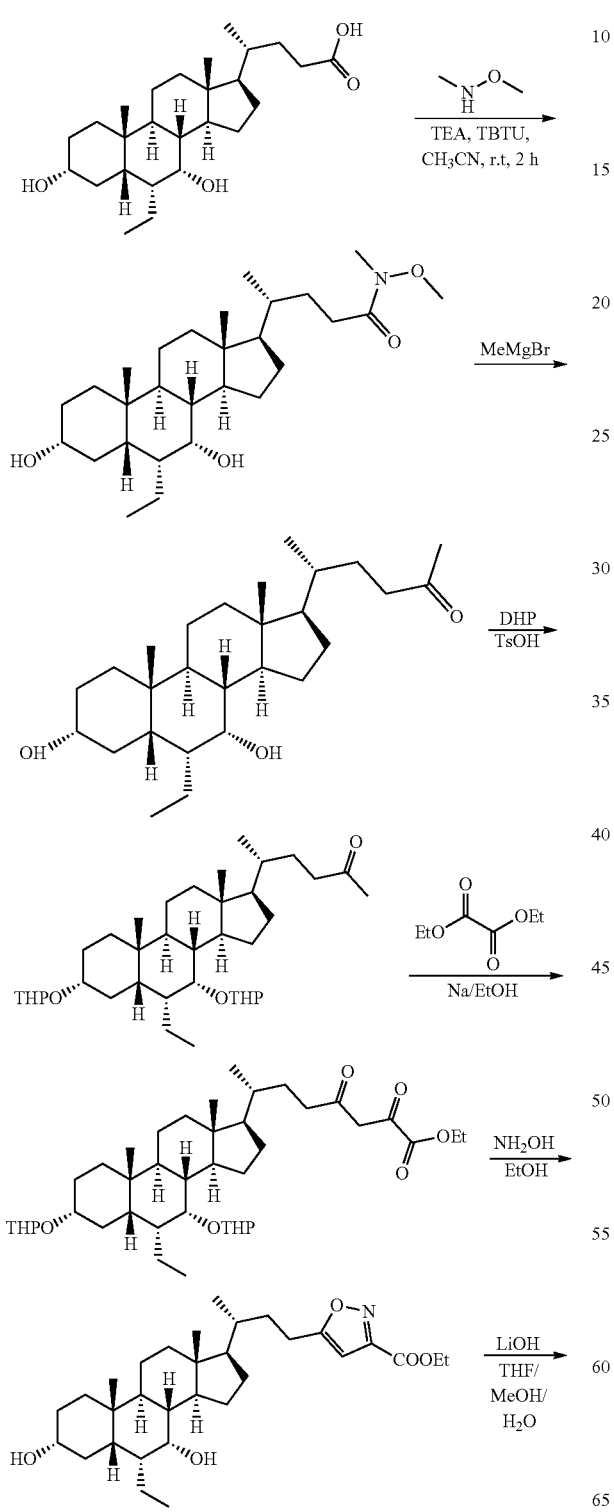

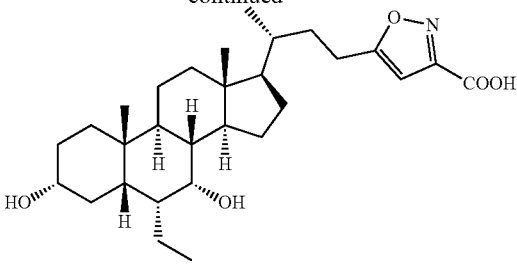

Example 21

Example 5A

After a mixture of Reference Example 1 (100.0 mg, 0.2 mmol), triethylamine (48.0 mg, 0.5 mmol) and O,N-dimethylhydroxylamine hydrochloride (23.0 mg, 0.2 mmol) in acetonitrile (2 mL) were stirred at 25° C. for 0.5 hour, O-benzotriazol-N,N,N',N'-tetramethyluronium tetrafluoroborate (95.0 mg, 0.3 mmol) was added thereto. The resulting mixture was stirred at 25° C. for 12 hours. After the solvent was removed by evaporation under vacuum, the residue was purified by column chromatography, so as to give Example 5A as a white solid (90 mg, 82% yield). $^1$H NMR (400 MHz, CHLOROFORM-d) δ 3.73-3.67 (m, 4H), 3.45-3.36 (m, 1H), 3.18 (s, 3H), 2.51-2.40 (m, 1H), 2.38-2.27 (m, 1H), 2.00-1.89 (m, 2H), 1.87-1.74 (m, 5H), 1.71-1.56 (m, 5H), 1.53-1.31 (m, 11H), 1.23-1.14 (m, 3H), 1.06-0.99 (m, 1H), 0.96 (d, J=6.3 Hz, 3H), 0.93-0.88 (m, 6H), 0.67 (s, 3H).

Example 5B

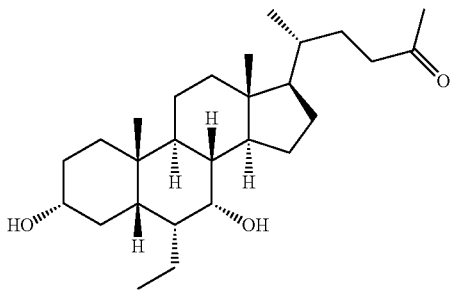

To a solution of Example 5A (100.0 mg, 0.2 mmol) in tetrahydrofuran (5 mL), a solution of methylmagnesium bromide (0.4 mL, 1.1 mmol, 3N) in diethyl ether was added at 0° C., and they were stirred at 0° C. for another 30 min, and then warmed up to room temperature and stirred for 12 hours. The reaction was quenched by adding ice water, and then they were extracted with ethyl acetate (60 mL×2). After being washed with water, the organic phase was dried over anhydrous sodium sulfate, and filtered. After the solvent was removed under vacuum, the residue was purified by preparative TLC, so as to give Example 5B as a white solid (6 mg, 66% yield). $^1$H NMR (400 MHz, CHLOROFORM-d) δ 3.71 (br. s., 1H), 3.48-3.35 (m, 1H), 2.51-2.41 (m, 1H), 2.39-2.29 (m, 1H), 2.14 (s, 3H), 1.99-1.79 (m, 5H), 1.76-1.56 (m, 5H), 1.51-1.30 (m, 10H), 1.22-1.11 (m, 3H), 1.00 (dt, J=3.3, 14.2 Hz, 1H), 0.94-0.87 (m, 9H), 0.66 (s, 3H).

Example 5C

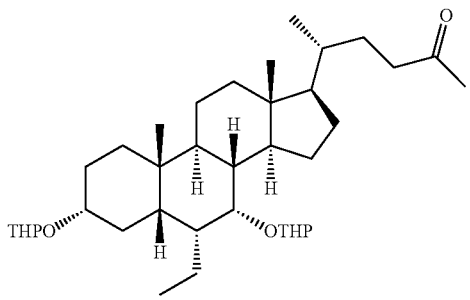

Example 5B (1.0 g, 2.4 mmol) was dissolved in 1,4-dioxane (20.0 mL), and 1,4-dihydropyran (2.0 g, 23.9 mmol, 2.2 mL) and p-toluenesulfonic acid (90.9 mg, 478.0 μmop were added thereto. The reaction solution was stirred at 30° C. for 36 hours. The solvent was removed by concentration, and water (5 mL) was added to the reaction solution, which was extracted with ethyl acetate (10 mL×3). The organic layer was washed with water (10 mL), dried over anhydrous sodium sulfate, filtered and concentrated, so as to give a crude product. The crude product was isolated by column chromatography, so as to give Example 5C (450.0 mg, 32.1% yield, colorless oil). $^1$H NMR (400 MHz, CHLOROFORM-d) δ 4.73 (d, J=3.3 Hz, 1H), 4.56 (d, J=4.3 Hz, 1H), 3.95-3.81 (m, 2H), 3.76-3.72 (m, 1H), 3.55-3.31 (m, 4H), 2.52-2.41 (m, 111), 2.34 (ddd, J=5.8, 9.9, 16.0 Hz, 1H), 1.97-1.80 (m, 7H), 1.74-1.67 (m, 4H), 1.55 (br. s., 4H), 1.41 (d, J=7.3 Hz, 3H), 1.33-1.27 (m, 3H), 1.17-1.08 (m, 3H), 0.90 (s, 311), 0.88 (s, 3H), 0.69-0.59 (m, 3H).

Example 5D

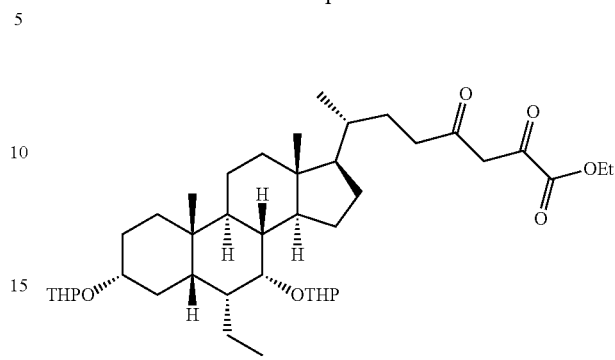

Metal sodium (68.2 mg, 3.0 mmol) was dissolved in anhydrous ethanol (5 mL), cooled to 0° C., to which Example 5C (170.0 mg, 296.8 μmol, dissolved in 2 mL of anhydrous ethanol) was slowly added, and they were stirred for another half an hour at 0° C. Then, diethyl oxalate (65.0 mg, 445.1 μmol, 60.8 μL, dissolved in 1 mL of anhydrous ethanol) was added dropwise. After being stirred at 0° C. for half an hour, the reaction solution was warmed up to 25° C. and stirred for another 35 hours. Ethanol (6 mL) was added to the reaction solution, and the solvent was removed by concentration. Ethyl acetate (40 mL) was added, and 2 mol of citric acid aqueous solution was added under stirring in an ice bath (to pH=5-6). The aqueous phase was extracted with ethyl acetate (10 mL×2). The organic layer was washed with water (10 mL), saline solution (10 mL), dried over anhydrous sodium sulfate, filtered and concentrated, so as to give a crude product. The crude product was isolated by column chromatography, so as to give Example 5D (90.0 mg, 44.2% yield). $^1$H NMR (400 MHz, CHLOROFORM-d) δ 4.73 (d, J=3.3 Hz, 1H), 4.57 (d, J=4.0 Hz, 1H), 4.36 (q, J=7.0 Hz, 2H), 3.97-3.80 (m, 2H), 3.70 (br. s., 1H), 3.52-3.34 (m, 3H), 2.54 (ddd, J=5.1, 10.3, 15.4 Hz, 1H), 2.44-2.29 (m, 1H), 1.98-1.90 (m, 2H), 1.82 (br. s., 3H), 1.74-1.67 (m, 4H), 1.53 (br. s., 7H), 1.38 (s, 3H), 1.26 (t, J=7.0 Hz, 2H), 1.16 (d, J=9.8 Hz, 2H), 0.95 (d, J=6.5 Hz, 2H), 0.89 (s, 3H), 0.71-0.59 (m, 3H).

Example 5E

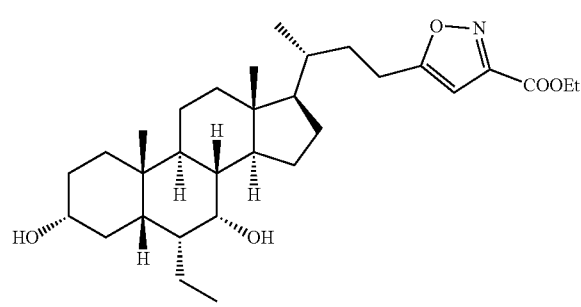

Example 5D (90.0 mg, 131.0 μmol) was dissolved in ethanol (3.0 mL), and hydroxylamine hydrochloride (27.3 mg, 393.0 μmol) was added thereto, and the reaction solution was stirred at 80° C. for 5 hours. The solvent was removed by concentration, and water (5 mL) was added to the reaction solution. The aqueous phase was extracted with ethyl acetate (10 mL×3). The organic layer was washed with water (10 mL), dried over anhydrous sodium sulfate, filtered, and the filtrate was evaporated to dryness under vacuum. Example 5E was obtained without purifying the crude product (86.0 mg, crude product, yellow oil). $^1$H NMR (400 MHz, CHLOROFORM-d) δ 6.39 (s, 1H), 4.43 (q, J=7.3 Hz, 2H), 3.72 (br. s., 1H), 3.43-3.40 (m, 1H), 2.90-2.64 (m, 2H), 2.42 (t, J=6.9 Hz, 2H), 2.00-1.95 (m, 2H), 1.75 (d, J=6.8 Hz, 3H), 1.69 (br. s., 4H), 1.60 (d, J=3.3 Hz, 3H), 1.48 (d, J=7.5 Hz, 4H), 1.41 (s, 3H), 1.28 (br. s., 4H), 1.20 (d, J=8.5 Hz, 3H), 0.90 (s, 3H), 0.89-0.88 (m, 1H), 0.65 (s, 3H).

Example 21

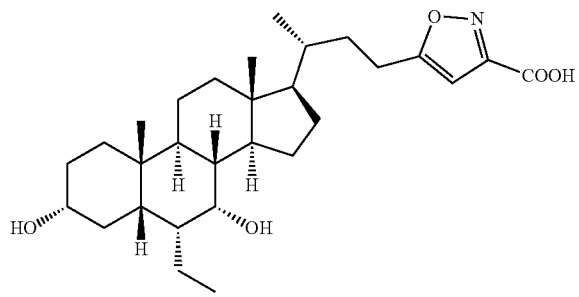

Example 5E (115.0 mg, 222.9 μmol) was dissolved in tetrahydrofuran (1.0 mL), water (1.0 mL) and methanol (1.0 mL), and lithium hydroxide monohydrate (93.6 mg, 2.2 mmol) were added thereto. The reaction solution was stirred at 25° C. for 12 hours. The reaction solution was acidified with 1 mol of hydrochloric acid (to pH=5-6), and extracted with ethyl acetate (10 mL×3). The organic layer was washed with water (10 mL), dried over anhydrous sodium sulfate and filtered. The filtrate was evaporated to dryness under vacuum. The crude product was isolated by thin layer chromatography, so as to give Example 21 (28.0 mg, 25.8% yield). $^1$H NMR (400 MHz, METHANOL-$d_4$) δ 6.41 (s, 1H), 3.67 (br. s., 1H), 3.31 (br. s., 1H), 2.94-2.83 (m, 1H), 2.80-2.70 (m, 1H), 2.03 (d, J=12.0 Hz, 1H), 1.96-1.83 (m, 5H), 1.80-1.73 (m, 2H), 1.64 (br. s., 1H), 1.58-1.50 (m, 5H), 1.48-1.42 (m, 2H), 1.42-1.34 (m, 3H), 1.32-1.27 (m, 3H), 1.24 (d, J=9.5 Hz, 2H), 1.05 (d, J=6.0 Hz, 3H), 0.93 (s, 3H), 0.92-0.89 (m, 3H), 0.71 (s, 3H).

Route 6

$R_b$=H or X, for example:

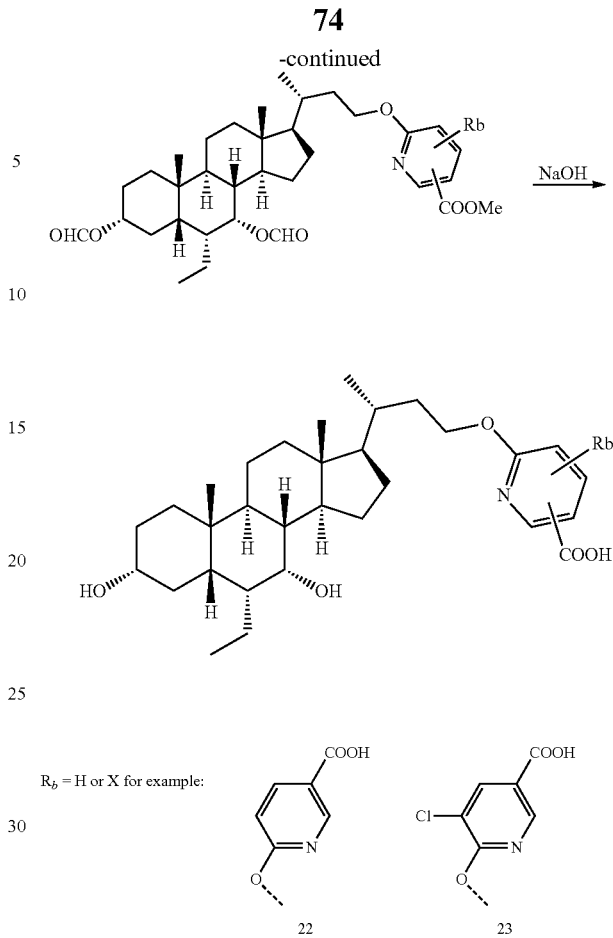

(?) indicates text missing or illegible when filed

Example 22

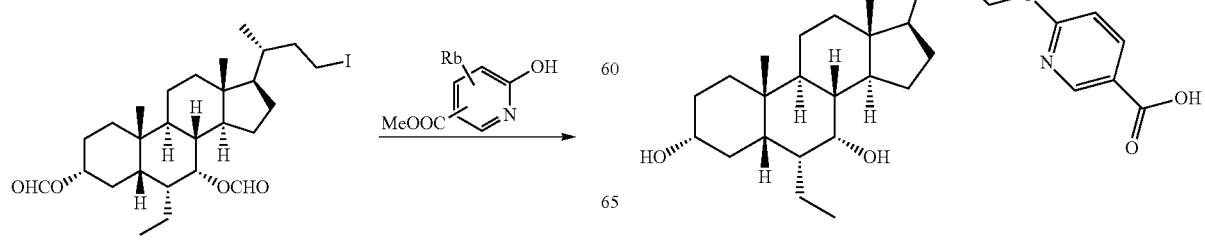

Example 6A

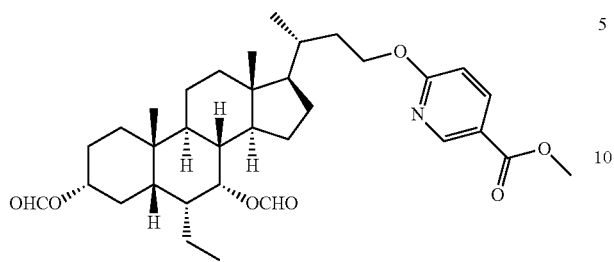

To a solution of methyl 6-hydroxynicotinate (438.7 mg, 2.9 mmol), Example 1B (800 mg, 1.4 mmol) in chloroform (20 mL), silver carbonate (790 mg, 2.9 mmol) was added. The reaction system was reacted at 60° C. for 72 hours, filtered, and concentrated. The residue was isolated by column (petroleum ether:ethyl acetate=10:1), so as to give the title compound 6A (400 mg, 47.9%). $^1$H NMR (400 MHz, CHLOROFORM-d) δ 8.82 (d, J=2.3 Hz, 1H), 8.16 (s, 1H), 8.16-8.12 (m, 1H), 8.05 (s, 1H), 6.74 (d, J=8.5 Hz, 1H), 5.21 (br. s., 1H), 4.80-4.61 (m, 1H), 4.48-4.27 (m, 2H), 3.91 (s, 3H), 2.02-1.63 (m, 11H), 1.46-1.09 (m, 14H), 1.02 (d, J=6.5 Hz, 3H), 0.97 (s, 3H), 0.94-0.89 (m, 3H), 0.68 (s, 3H).

Example 22

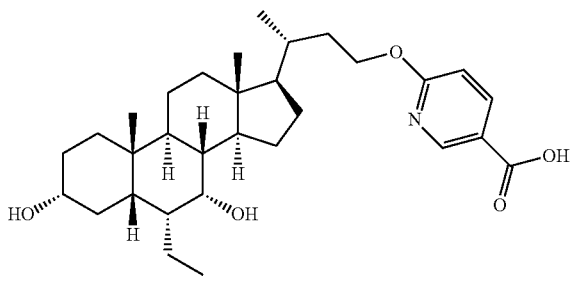

To a solution of Example 6A (800 mg, 1.4 mmol) in methanol (10 mL), a solution of 10% sodium hydroxide (volume ratio of methanol to water was 1:1) (600 mg, 15 mmol, 6 mL) was added, and the reaction system was reacted at 70° C. for 2 hours. The solvent was evaporated to dryness. The system was adjusted to pH=1-2 with dilute hydrochloric acid (1M) and extracted with dichloromethane:methanol=10:1 (20 mL×3). The organic layer was dried over anhydrous sodium sulfate, filtered and concentrated. The residue was purified by preparative chromatography, so as to give the title compound 22 (460 mg, 64% yield). $^1$H NMR (400 MHz, METHANOL-d$_4$) δ 8.78 (d, J=1.8 Hz, 1H), 8.21 (dd, J=2.3, 8.5 Hz, 1H), 6.84 (d, J=8.8 Hz, 1H), 4.56-4.23 (m, 2H), 3.68 (br. s., 1H), 3.35-3.34 (m, 1H), 2.04-1.17 (m, 25H), 1.07 (d, J=6.5 Hz, 3H), 0.96-0.89 (m, 6H), 0.74 (s, 3H).

The preparation of Examples 23-26 was referred to the procedure of the title compound 22.

| Compound No. | Yield % | Compound structure | $^1$H NMR |
|---|---|---|---|
| Example 23 | 47.2% | | $^1$H NMR (400 MHz, METHANOL-d$_4$) δ 8.68 (br. s., 1H), 8.24 (s, 1H), 4.61-4.37 (m, 2H), 3.67 (br. s., 1H), 3.37 (s, 1H), 2.04-1.18 (m, 25H), 1.08 (d, J = 6.3 Hz, 3H), 0.95-0.89 (m, 6H), 0.73 (s, 3H) |
| Example 24 | 56.6% | | $^1$H NMR (400 MHz, METHANOL-d$_4$) δ 8.58 (d, J = 1.8 Hz, 1H), 7.94 (dd, J = 1.8, 10.5 Hz, 1H), 4.55-4.37 (m, 2H), 3.74-3.58 (m, 1H), 3.32-3.28 (m, 1H), 2.08-1.20 (m, 25H), 1.08 (d, J = 6.5 Hz, 3H), 0.95-0.87 (m, 6H), 0.73 (s, 3H) |

-continued

| Compound No. | Yield % | Compound structure | ¹H NMR |
|---|---|---|---|
| Example 25 | 56.7% | 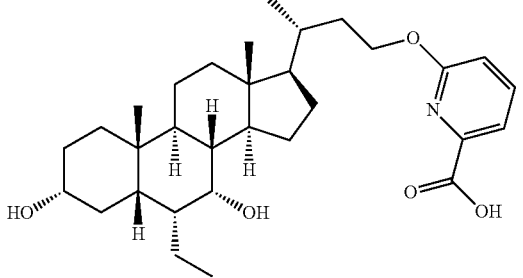 | ¹H NMR (400 MHz, METHANOL-d₄) δ = 7.85-7.78 (m, 1H), 7.73 (d, J = 7.3 Hz, 1H), 7.00 (d, J = 8.3 Hz, 1H), 4.53-4.34 (m, 2H), 3.68 (br s, 1H), 2.02-1.10 (m, 25H), 1.08 (br d, J = 6.5 Hz, 3H), 0.97-0.88 (m, 6H), 0.74 (s, 3H) |
| Example 26 | 75.6% | 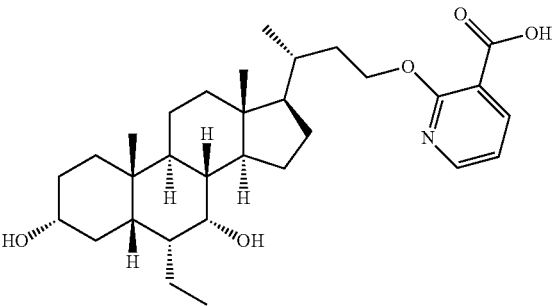 | ¹H NMR (400 MHz, METHANOL-d₄) δ = 8.30 (d, J = 5.5 Hz, 1H), 7.54 (dd, J = 1.3, 5.5 Hz, 1H), 7.43 (s, 1H), 4.57-4.29 (m, 2H), 3.66 (br s, 1H), 2.08-1.10 (m, 25H), 1.06 (d, J = 6.5 Hz, 3H), 0.95-0.87 (m, 6H), 0.73 (s, 3H) |

Route 7

Example 27

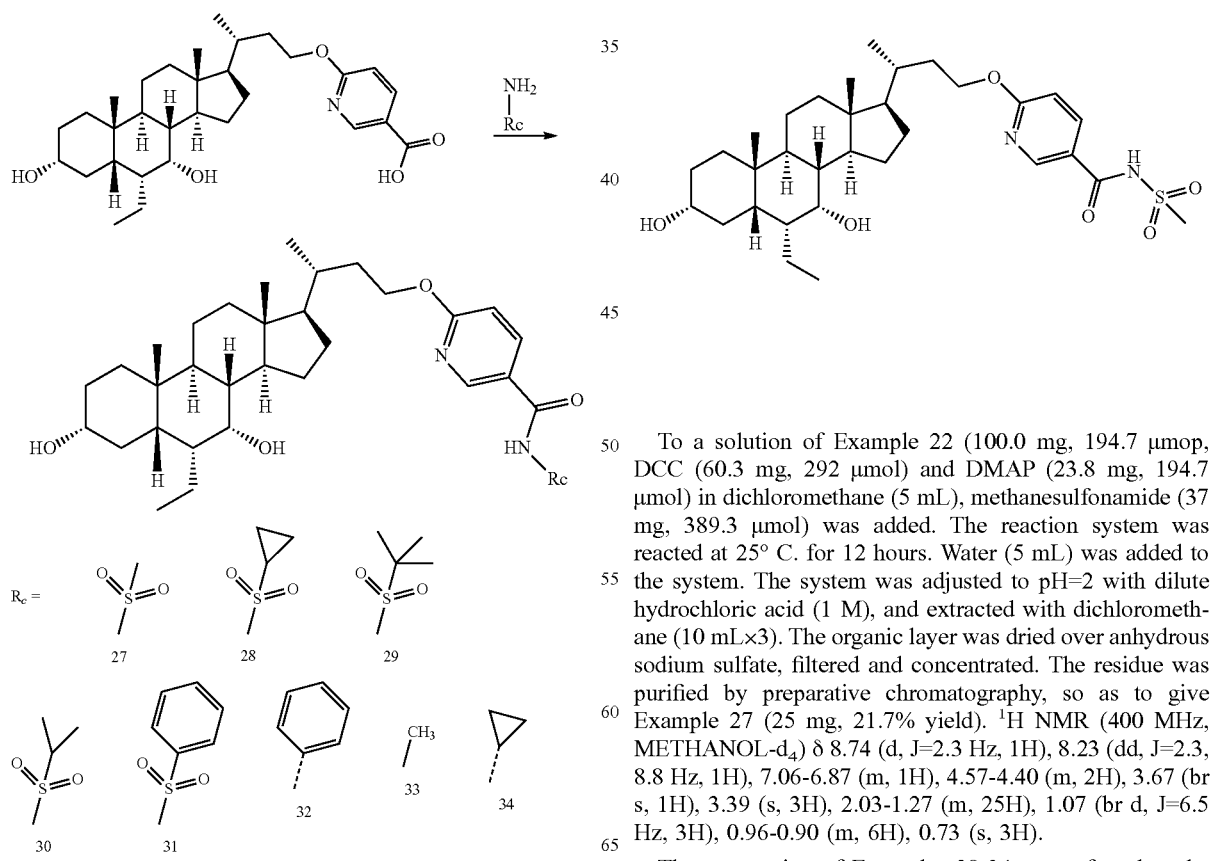

To a solution of Example 22 (100.0 mg, 194.7 μmop, DCC (60.3 mg, 292 μmol) and DMAP (23.8 mg, 194.7 μmol) in dichloromethane (5 mL), methanesulfonamide (37 mg, 389.3 μmol) was added. The reaction system was reacted at 25° C. for 12 hours. Water (5 mL) was added to the system. The system was adjusted to pH=2 with dilute hydrochloric acid (1 M), and extracted with dichloromethane (10 mL×3). The organic layer was dried over anhydrous sodium sulfate, filtered and concentrated. The residue was purified by preparative chromatography, so as to give Example 27 (25 mg, 21.7% yield). ¹H NMR (400 MHz, METHANOL-d₄) δ 8.74 (d, J=2.3 Hz, 1H), 8.23 (dd, J=2.3, 8.8 Hz, 1H), 7.06-6.87 (m, 1H), 4.57-4.40 (m, 2H), 3.67 (br s, 1H), 3.39 (s, 3H), 2.03-1.27 (m, 25H), 1.07 (br d, J=6.5 Hz, 3H), 0.96-0.90 (m, 6H), 0.73 (s, 3H).

The preparation of Examples 28-34 was referred to the procedure of the title compound 27.

| Compound No. | Yield % | Compound structure | ¹H NMR |
|---|---|---|---|
| Example 28 | 50.0 | 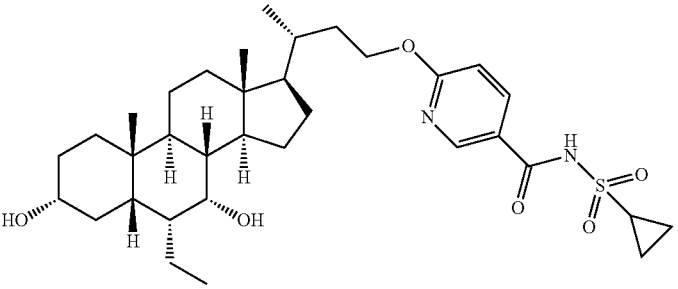 | ¹H NMR (400 MHz, METHANOL-d₄) δ 8.72 (d, J = 2.3 Hz, 1H), 8.23 (dd, J = 2.4, 8.9 Hz, 1H), 6.97 (d, J = 8.8 Hz, 1H), 4.54-4.32 (m, 2H), 3.65 (br s, 1H), 3.56-3.38 (m, 1H), 3.18-3.07 (m, 1H), 2.02-1.15 (m, 29H), 1.05 (d, J = 6.3 Hz, 3H), 0.93-0.87 (m, 6H), 0.71 (s, 3H) |
| Example 29 | 26.0 | 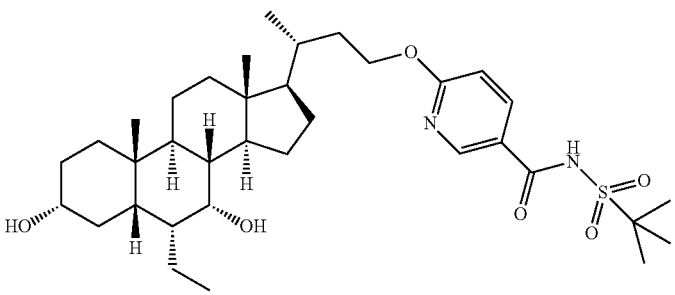 | ¹H NMR (400 MHz, METHANOL-d₄) δ 8.69 (d, J = 2.3 Hz, 1H), 8.16 (dd, J = 2.4, 8.9 Hz, 1H), 6.91 (d, J = 8.8 Hz, 1H), 4.56-4.27 (m, 2H), 3.66 (br s, 1H), 3.46 (s, 1H), 2.05-1.57 (m, 15H), 1.50 (s, 9H), 1.33-1.09 (m, 10H), 1.05 (d, J = 6.5 Hz, 3H), 0.93-0.86 (m, 6H), 0.71 (s, 3H) |
| Example 30 | 39.8 | 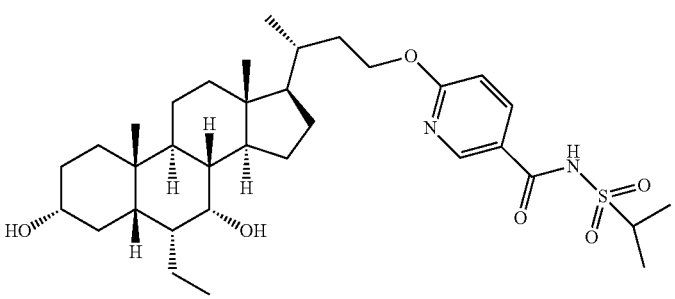 | ¹H NMR (400 MHz, METHANOL-d₄) δ = 8.70 (d, J = 2.0 Hz, 1H), 8.13 (dd, J = 2.5, 8.8 Hz, 1H), 6.86 (d, J = 8.8 Hz, 1H), 4.50-4.33 (m, 2H), 3.91 (quin, J = 6.9 Hz, 1H), 3.66 (br s, 1H), 3.50-3.34 (m, 1H), 2.05-1.49 (m, 16H), 1.42 (d, J = 7.0 Hz, 6H), 1.39-1.08 (m, 9H), 1.05 (d, J = 6.5 Hz, 3H), 0.93-0.86 (m, 6H), 0.72 (s, 3H) |
| Example 31 | 68.5 | 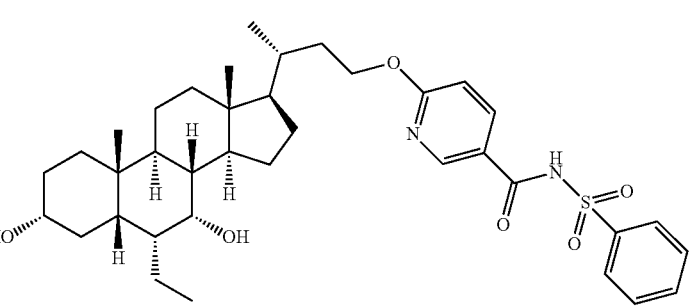 | ¹H NMR (400 MHz, CHLOROFORM-d) δ 8.62 (br s, 1H), 8.09 (br d, J = 7.8 Hz, 2H), 7.96 (br d, J = 6.0 Hz, 1H), 7.62-7.55 (m, 1H), 7.53-7.46 (m, 2H), 6.78-6.63 (m, 1H), 6.70 (br d, J = 5.8 Hz, 1H), 4.41-4.21 (m, 2H), 3.64 (br s, 1H), 3.37 (br s, 1H), 1.98-1.66 (m, 12H), 1.63-1.48 (m, 5H), 1.45-1.02 (m, 15H), 0.97-0.89 (m, 4H), 0.85-0.78 (m, 6H), 0.59 (s, 3H). |
| Example 32 | 76.8 | 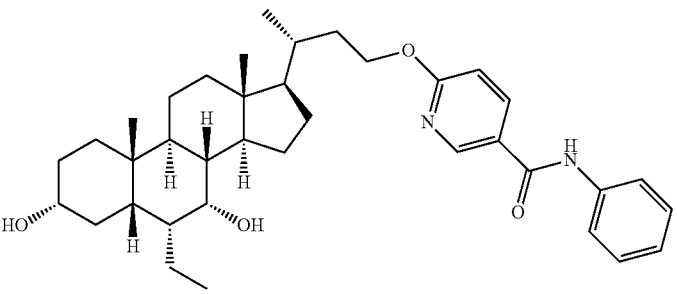 | ¹H NMR (400 MHz, CHLOROFORM-d) δ 8.74 (br s, 1H), 8.19-8.01 (m, 1H), 8.12 (br s, 1H), 7.60 (br d, J = 7.8 Hz, 2H), 7.35-7.26 (m, 1H), 7.30 (br t, J = 7.5 Hz, 1H), 7.13-7.04 (m, 1H), 6.80 (br s, 1H), 4.46-4.23 (m, 2H), 3.64 (br s, 1H), 3.34 (br s, 1H), 1.97-1.68 (m, 15H), 1.63-1.49 (m, 5H), 1.46-1.03 (m, 15H), 1.00-0.88 (m, 4H), 0.86-0.79 (m, 7H), 0.62 (s, 3H). |

-continued
| Compound No. | Yield % | Compound structure | ¹H NMR |
|---|---|---|---|
| Example 33 | 69.6 | | ¹H NMR (400 MHz, METHANOL-d₄) δ 8.62 (s, 1H), 8.21-8.01 (m, 1H), 6.89 (br s, 1H), 4.52-4.30 (m, 2H), 3.68 (br s, 1H), 3.57-3.44 (m, 1H), 2.93 (s, 3H), 2.04-1.25 (m, 25H), 1.07 (d, J = 6.5 Hz, 3H), 0.95-0.94 (m, 1H), 0.95-0.90 (m, 6H), 0.74 (s, 3H) |
| Example 34 | | | ¹H NMR (400 MHz, CHLOROFORM-d) δ 9.12 (br s, 1H), 8.63-8.46 (m, 1H), 8.56 (br s, 1H), 8.03 (br s, 1H), 7.17-6.99 (m, 1H), 4.69-4.38 (m, 2H), 3.65-3.28 (m, 5H), 3.03-2.87 (m, 1H), 2.09-1.57 (m, 13H), 1.52-1.13 (m, 13H), 1.08-0.96 (m, 4H), 0.93-0.76 (m, 11H), 0.69 (s, 3H). |
Route 8
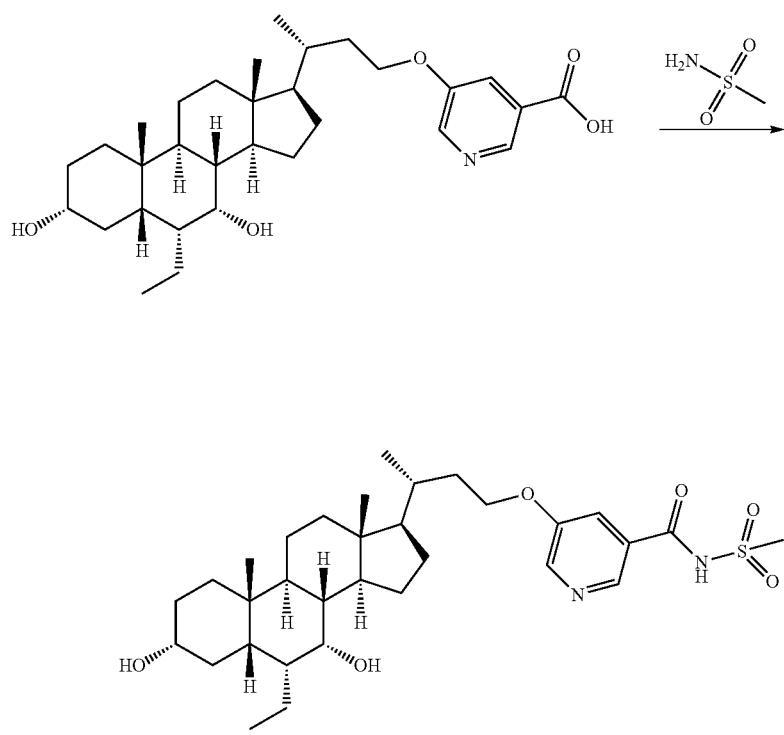

Example 35

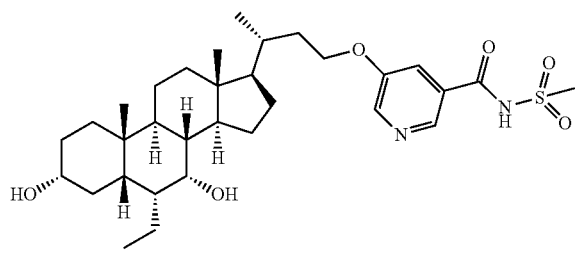

Example 35 was synthesized by using Example 11 as a raw material, and the procedure was referred to the synthesis of Example 27. The yield was 17.4%. $^1$H NMR (400 MHz, METHANOL-$d_4$) δ 8.95-8.70 (m, 2H), 8.48 (s, 1H), 4.41-4.27 (m, 2H), 3.67 (br s, 1H), 3.41 (s, 3H), 3.33-3.32 (m, 1H), 2.02-1.16 (m, 25H), 1.08 (d, J=6.3 Hz, 3H), 0.94-0.88 (m, 6H), 0.74 (s, 3H).

Route 9

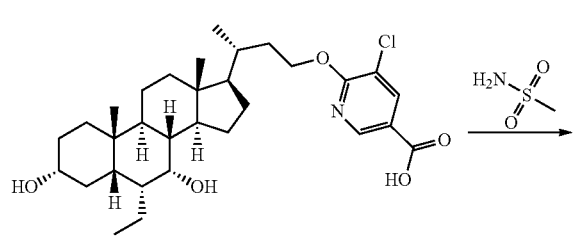

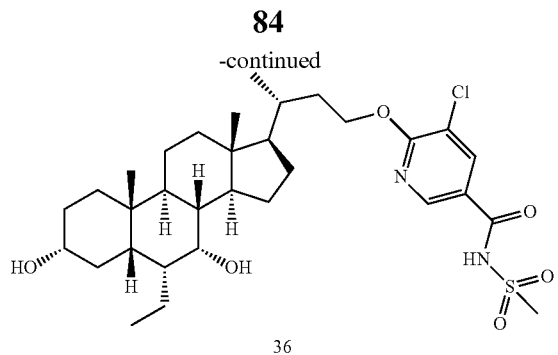

Example 36

Example 36 was synthesized by using Example 23 as a raw material, and the procedure was referred to the synthesis of Example 27. The yield was 17.5%. $^1$H NMR (400 MHz, CHLOROFORM-d) δ=8.60 (d, J=2.3 Hz, 1H), 8.18 (d, J=2.3 Hz, 1H), 4.56-4.33 (m, 2H), 3.69 (br s, 1H), 3.45 (s, 3H), 1.96-1.15 (m, 25H), 1.01 (d, J=6.5 Hz, 3H), 0.89-0.81 (m, 6H), 0.66 (s, 3H).

Route 10

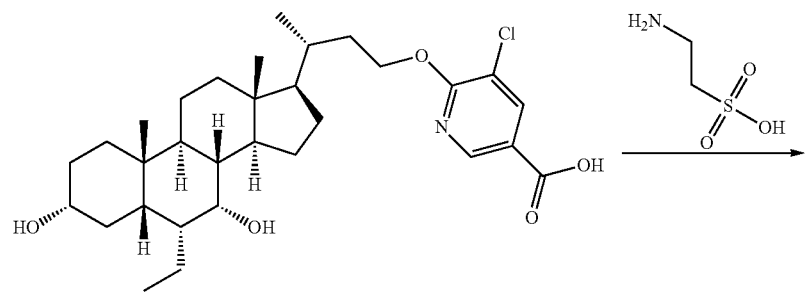

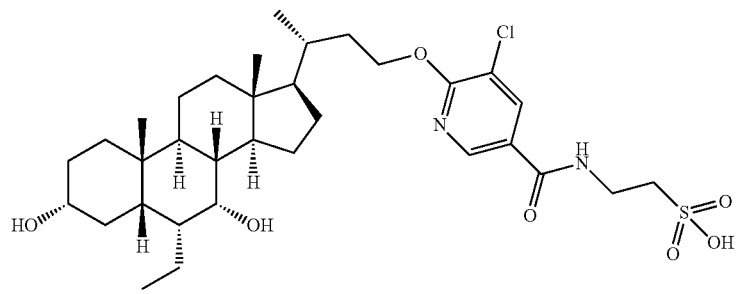

Example 37

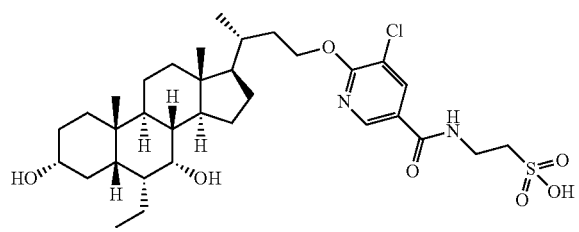

Example 38

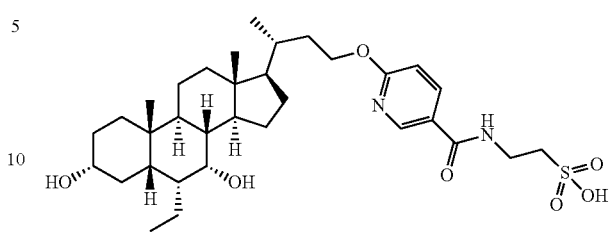

Example 37 was synthesized by using Example 23 as a raw material, and the procedure was referred to the synthesis of Example 27. The yield was 60.8%. $^1$H NMR (400 MHz, METHANOL-$d_4$) δ 8.55 (d, J=1.8 Hz, 1H), 8.17 (d, J=1.8 Hz, 1H), 4.57-4.38 (m, 2H), 3.87-3.75 (m, 2H), 3.66 (br s, 1H), 3.32-3.20 (m, 1H), 3.11 (t, J=6.9 Hz, 2H), 2.06-1.23 (m, 25H), 1.06 (br d, J=6.5 Hz, 3H), 0.96-0.86 (m, 6H), 0.71 (s, 3H).

Route 11

Example 38 was synthesized by using Example 22 as a raw material, and the procedure was referred to the synthesis of Example 27. The yield was 53%. $^1$H NMR (400 MHz, METHANOL-$d_4$) 8.63-8.62 (m, 1H), 8.09-8.06 (m, 1H), 6.84-6.82 (m, 1H), 4.39-4.28 (m, 2H), 3.82-3.74 (m, 3H), 3.40-3.30 (m, 1H), 3.12-3.08 (m, 2H), 1.99-1.20 (m, 25H), 1.06 (d, J=6.5 Hz, 3H), 0.94-0.90 (m, 6H), 0.73 (s, 3H).

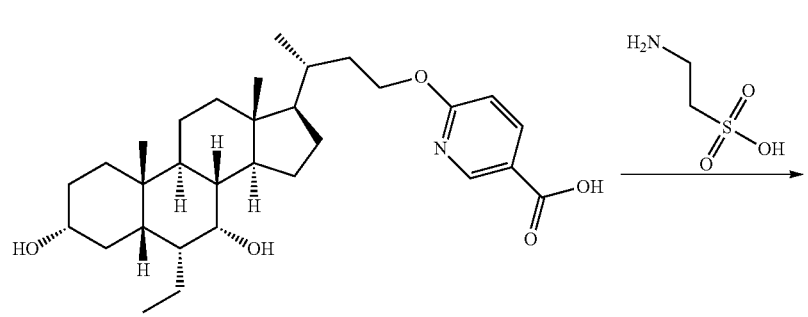

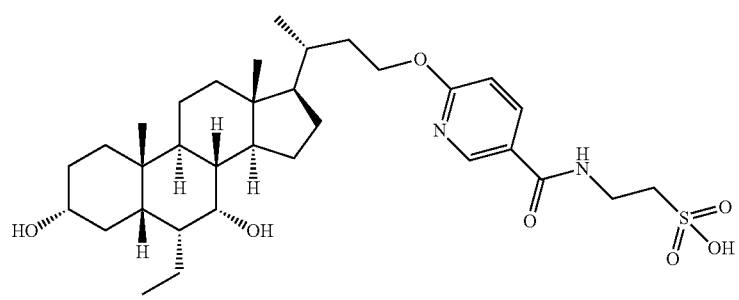

Route 12
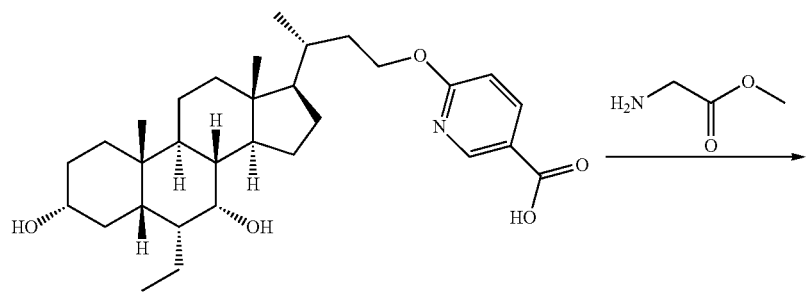
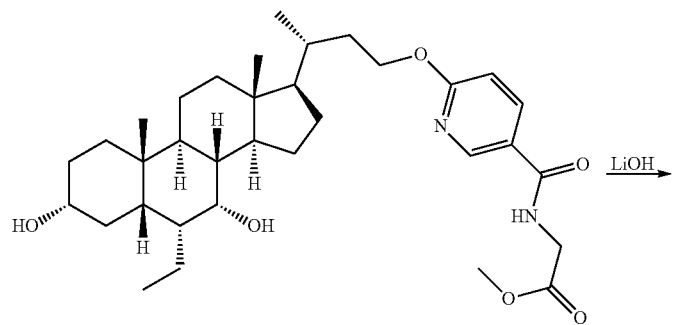
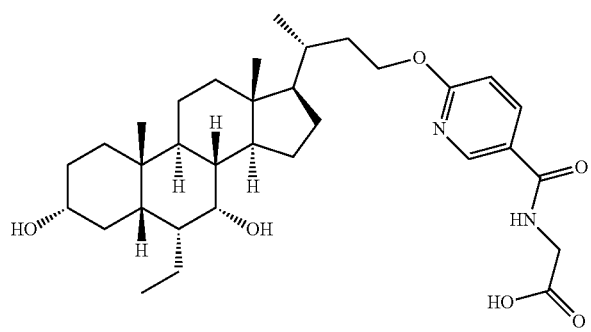

Example 39

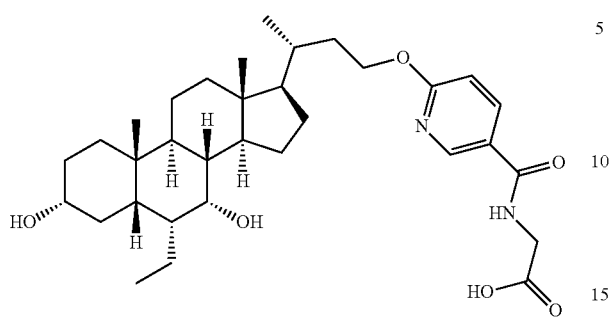

Example 12A

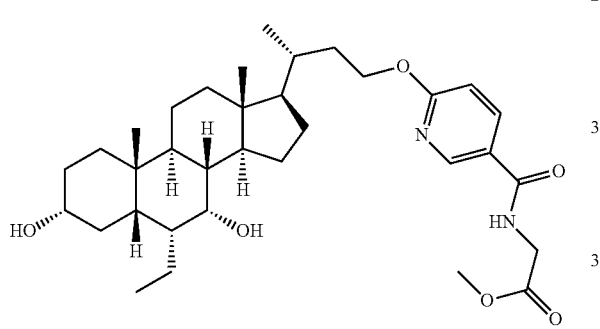

Glycine hydrochloride (14 mg, 112 μmol) was reacted with a solution of triethylamine (20.0 μL, 146 μmol) in ethyl acetate (5 mL) at 20° C. for 0.5 hour. Example 22 (50 mg, 97 μmop and 2-ethoxy-1-ethoxycarbonyl-1.2-dihydroquinoline (36 mg, 146 μmol) were added to the system. The reaction system was reacted at 65° C. for 10 hours. Water (5 mL) was added to the system, and the aqueous phase was extracted with ethyl acetate (15 mL×2). The organic phases were combined and sequentially washed with 0.5 N of aqueous sodium hydroxide solution (15 mL), water (15 mL), 0.5 N of hydrochloric acid (15 mL) and water (15 mL). The organic layer was dried over anhydrous sodium sulfate, filtered and evaporated to dryness. The crude product was isolated and purified by preparative isolation (TFA), so as to give Example 12A (25 mg, 43.9%). $^1$H NMR (400 MHz, CDCl$_3$) 8.66-8.65 (m, 1H), 8.08-8.05 (m, 1H), 6.81-6.67 (m, 1H), 6.68 (s, 1H), 4.42-4.24 (m, 2H), 4.35-4.24 (m, 2H), 3.81 (s, 3H), 3.72-3.71 (m, 1H), 3.46-3.44 (m, 1H), 1.99-1.20 (m, 25H), 1.03 (d, J=6.5 Hz, 3H), 0.92-0.88 (m, 6H), 0.68 (s, 3H).

Example 39

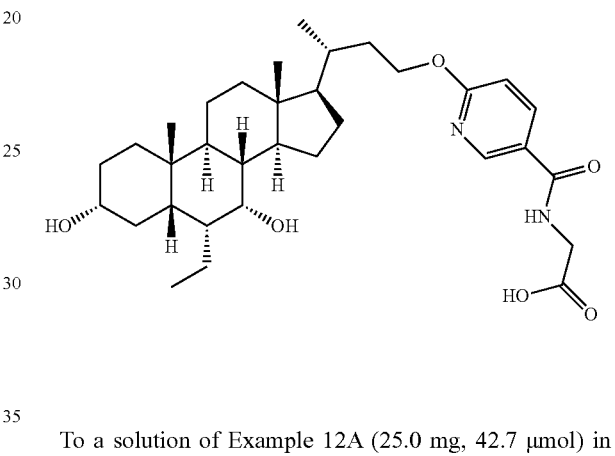

To a solution of Example 12A (25.0 mg, 42.7 μmol) in tetrahydrofuran (3 mL), methanol (1 mL) and water (2 mL), lithium hydroxide (8.9 mg, 213.7 μmol) was added. The reaction system was reacted at 30° C. for 4 hours. The system was adjusted to pH=5 with hydrochloric acid (1M), and the aqueous phase was extracted with ethyl acetate (20 mL×2). The organic layers were combined, and dried over sodium sulfate, filtered and evaporated to dryness. The residue was isolated by preparative TLC, so as to give Example 39 (24 mg, 98%). $^1$H NMR (400 MHz, METHANOL-d$_4$) 8.66-8.65 (m, 1H), 8.11-8.02 (m, 1H), 6.84-6.82 (m, 1H), 4.48-4.29 (m, 2H), 4.09-4.08 (m, 3H), 3.66-3.65 (m, 1H), 1.99-1.20 (m, 25H), 1.06 (d, J=6.5 Hz, 3H), 0.92-0.88 (m, 6H), 0.72 (s, 3H).

Route 13

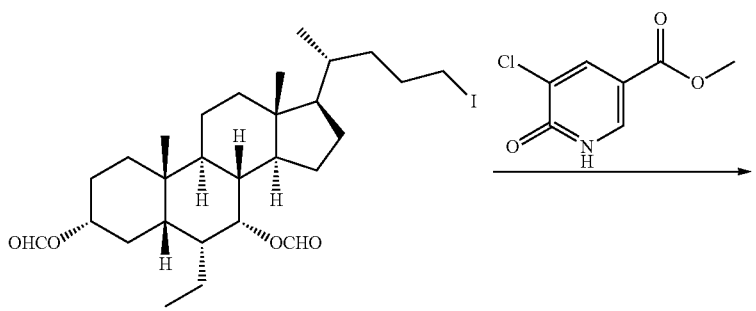

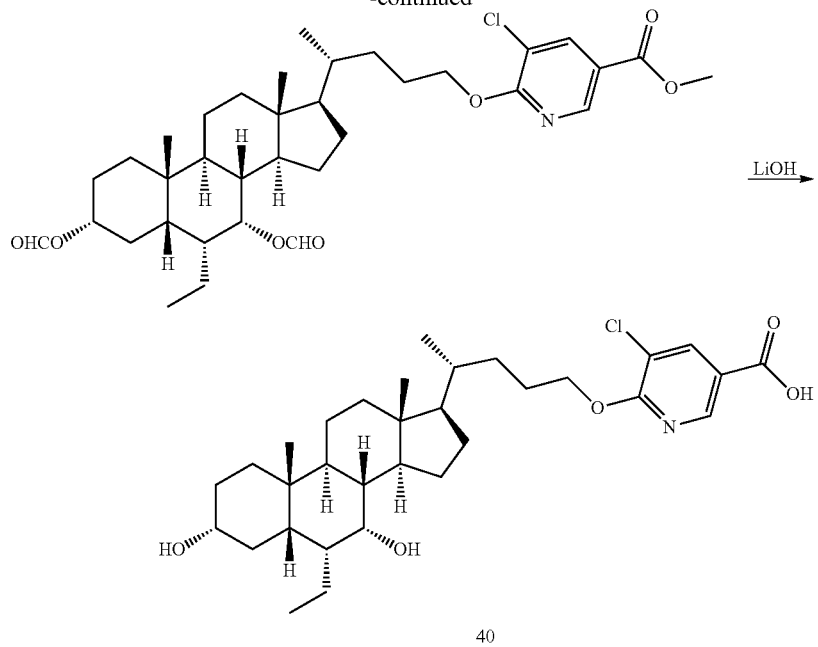

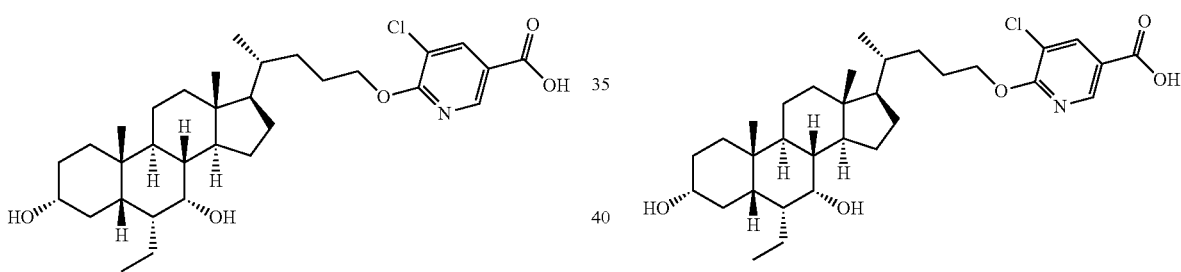

Example 40

Example 40

Example 13A

The procedure of Example 40 was referred to the synthesis of Example 22. The yield was 96.4%. ¹H NMR (400 MHz, METHANOL-d₄) δ=8.74 (d, J=2.0 Hz, 1H), 8.29 (d, J=1.8 Hz, 1H), 4.51 (t, J=6.4 Hz, 2H), 3.72 (br s, 1H), 3.43-3.39 (m, 1H), 2.11-1.23 (m, 27H), 1.07 (d, J=6.5 Hz, 3H), 1.00-0.93 (m, 6H), 0.77 (s, 3H).

Route 14

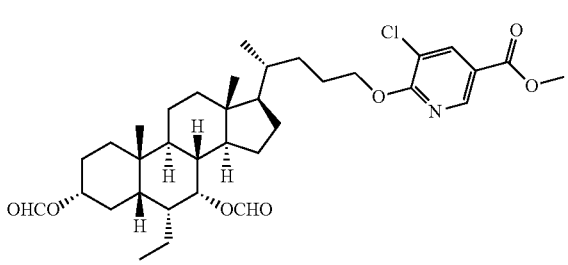

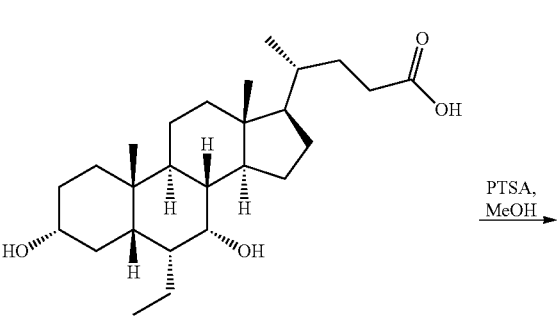

Using Example 2B as a raw material, the procedure of Example 13A was referred to the synthesis of Example 6A. The yield was 16.3%. ¹H NMR (400 MHz, CHLOROFORM-d) δ 8.69 (d, J=2.0 Hz, 1H), 8.21 (d, J=2.0 Hz, 1H), 8.16 (s, 1H), 8.05 (s, 1H), 5.20 (br s, 1H), 4.72 (br s, 1H), 4.46-4.36 (m, 2H), 3.92 (s, 3H), 2.06-1.66 (m, 15H), 1.31-1.04 (m, 10H), 0.97-0.81 (m, 9H), 0.67 (s, 3H).

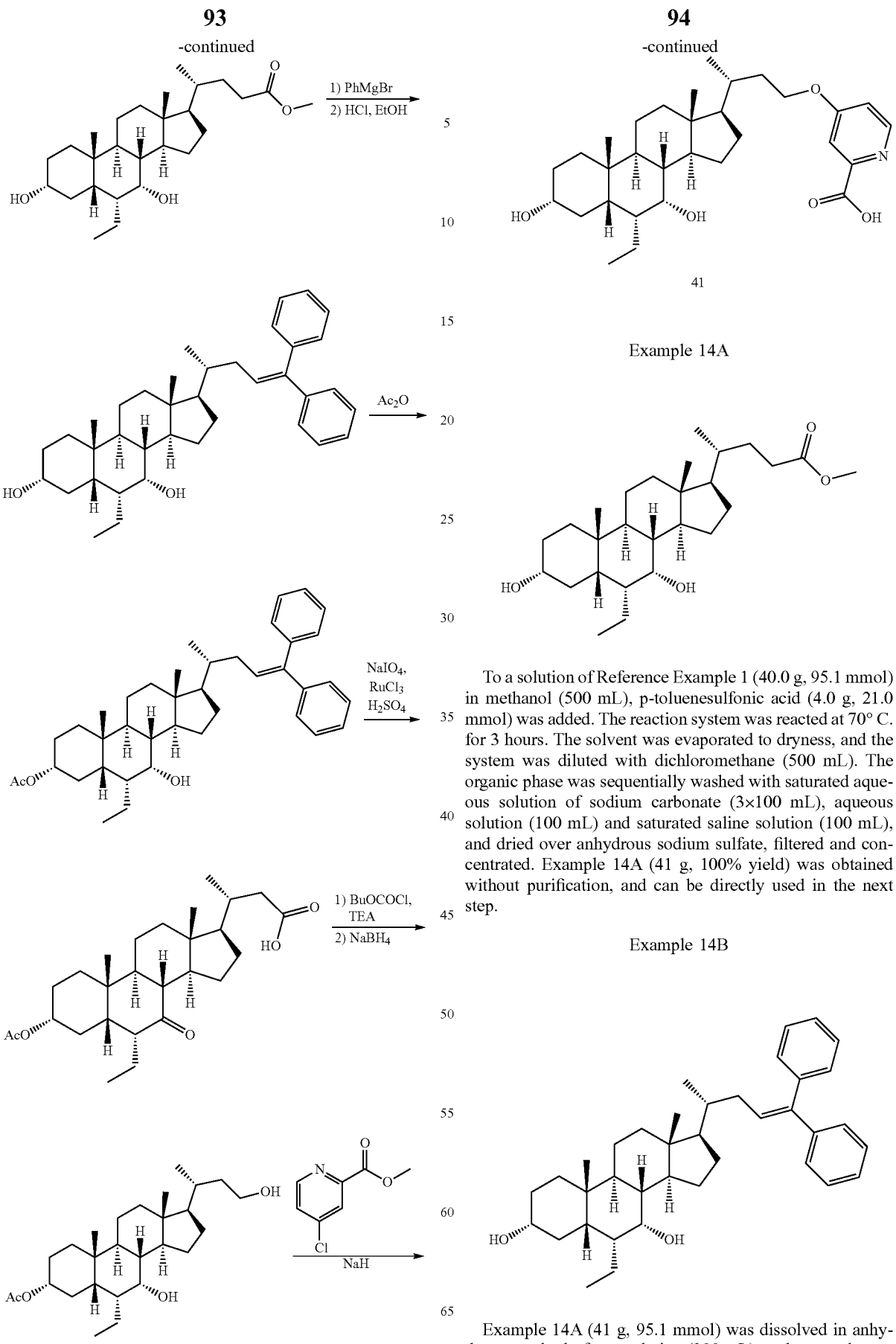

Example 14A

To a solution of Reference Example 1 (40.0 g, 95.1 mmol) in methanol (500 mL), p-toluenesulfonic acid (4.0 g, 21.0 mmol) was added. The reaction system was reacted at 70° C. for 3 hours. The solvent was evaporated to dryness, and the system was diluted with dichloromethane (500 mL). The organic phase was sequentially washed with saturated aqueous solution of sodium carbonate (3×100 mL), aqueous solution (100 mL) and saturated saline solution (100 mL), and dried over anhydrous sodium sulfate, filtered and concentrated. Example 14A (41 g, 100% yield) was obtained without purification, and can be directly used in the next step.

Example 14B

Example 14A (41 g, 95.1 mmol) was dissolved in anhydrous tetrahydrofuran solution (300 mL), and warmed up to 50° C. under nitrogen atmosphere, and a solution of methylmagnesium bromide (800 mL, 1 M) in tetrahydrofuran was slowly added dropwise. After the dropwise addition was completed, the reaction solution was cooled to room temperature, and stirred overnight. After the reaction was completed, cyclohexane (25 mL) was added and filtered. The filter residue was dissolved in a mixed solution of 3N aqueous hydrochloric acid solution (800 mL) and dichloromethane (200 mL). They were stirred for another 30 min. After the reaction was completed, the organic phase was separated from the aqueous phase. The aqueous phase was further extracted with dichloromethane (2×200 mL). The organic phases were combined and sequentially washed with water (100 mL) and saturated saline solution (100 mL), dried over anhydrous sodium sulfate, filtered and concentrated. Example 14B (51 g, 100% yield) was obtained without purification, and can be directly used in the next step.

Example 14C

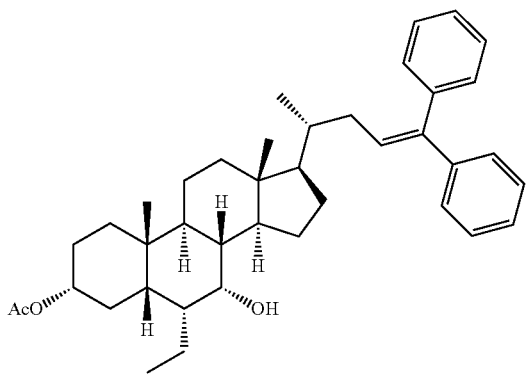

Acetic anhydride (9.9 mL, 105.1 mmol), pyridine (1.6 mL, 19.8 mmol) and 4-dimethylaminopyridine (0.8 g, 6.6 mmol) were added to a solution of Example 14B (51 g, 95.1 mmol) in anhydrous tetrahydrofuran (300 mL). The reaction solution was stirred overnight at room temperature. After the reaction was completed, it was diluted with aqueous solution (100 mL). The aqueous phase was extracted with dichloromethane (3×150 mL). The organic phases were combined, and washed with saturated saline solution (100 mL), dried over anhydrous sodium sulfate, filtered, and concentrated. Example 14C (55 g, 100% yield) was obtained without purification, and can be directly used in the next step.

$^1$H-NMR (CDCl$_3$) δ 0.66 (3H, s, CH$_3$—I8); 0.77 (3H, s, CH$_3$-26); 1.00 (3H, d, CH$_3$-21); 1.20 (3H, s, CH$_3$-19); 1.96 (3H, s, AcO), 2.18-2.31 (1H, m, CH-22); 3.70 (1H, m, CH-7); 4.55 (1H, m, CH-3); 6.11 (1H, dd, =6.2 Hz, J 2=8.3 Hz; CH-23); 7.14-7.36 (10H, m, Ph).

Example 14D

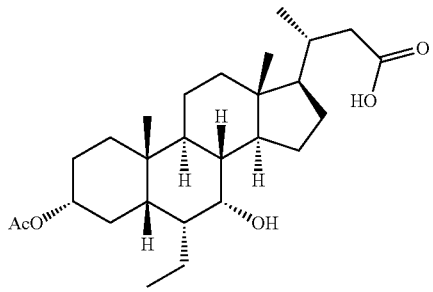

Sodium periodate (13.2 g, 61.9 mmol) was dissolved in water (13 mL) and 2N aqueous sulfuric acid solution (1.7 mL). After being stirred for 15 mins, the reaction solution was cooled to 0° C., and ruthenium trichloride (71.3 mg, 0.4 mmol) was added thereto. The reaction solution was stirred continuously until the color thereof turned bright yellow. Ethyl acetate (27 mL) and acetonitrile (20 mL) were added to the reaction solution, and they were stirred for another 5 min. Example 14C (4 g, 6.9 mmol) was added to the above reaction solution at 0° C., and it was filtered after the reaction was completed. The filtrate was poured into water and extracted with ethyl acetate (3×100 mL). The organic phases were combined and washed with saturated sodium thiosulfate solution (200 mL), dried over anhydrous sodium sulfate and filtered. The filtrate was evaporated to dryness, and then isolated by silica gel column chromatography, so as to give Example 14D (2.7 g, 89% yield).

$^1$H-NMR (CDCl$_3$) δ 0.71 (3H, s, CH$_3$-I8); 0.86-1.07 (9H, m, CH$_3$-19, CH$_3$-21, C-24); 2.03 (3H, s, AcO); 4.48-4.61 (1H, m, CH-3).

Example 14E

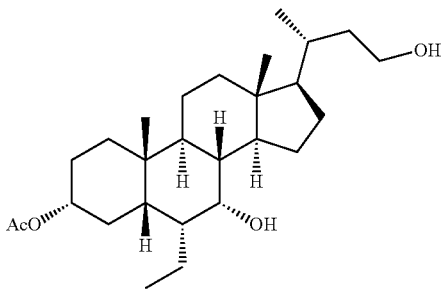

Triethylamine (6.7 mL, 3.4 mmol) was added to a solution of Example 14D (1 g, 2.2 mmol) and isobutyl chloroformate (3.5 mL, 2.7 mmol) in tetrahydrofuran (20 mL), and the reaction was completed after 1 hour. The reaction solution was filtered, and sodium borohydride (847 mg, 22.4 mmol) was added in portions to the filtrate at 0° C. After the reaction was completed, water (3 mL) was added to quench the reaction, and they were stirred at room temperature for another 2 hours, followed by acidified with 3N dilute aqueous hydrochloric acid, and extracted with ethyl acetate (3×15 mL). The organic phases were combined and washed with saturated saline solution (15 mL), dried over anhydrous sodium sulfate, and filtered. After the filtrate was evaporated to dryness, Example 14E (800 mg, 85% yield) was obtained by separation via silica gel column chromatography. $^1$H-NMR (CDCl$_3$) δ 0.67 (3H, s, CH$_3$-18); 0.86-0.97 (9H, m, CH$_3$-19, CH$_3$-21, CH$_3$-24); 2.03 (3H, s, AcO); 3.72 (3H, m, (2H, m, CH-7, CH-23); 4.48-4.61 (1H, m, CH-3).

Example 41

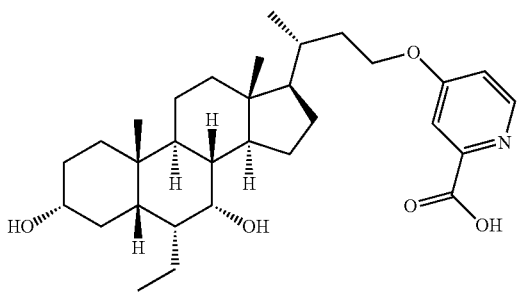

Sodium hydrogen (18.4 mg, 460.1 μmol, 60%) was added to a solution of Example 14E (100 mg, 230.1 μmop in N,N-dimethylformamide (1 mL) at 0° C. After half an hour, a solution of methyl 4-chloropicolinate (78.9 mg, 460.1 μmop in N,N-dimethylformamide (2 mL) was slowly added dropwise at 0° C. After the dropwise addition was completed, the reaction system was slowly warmed up to room temperature and reacted for 12 hours. Water (10 mL) was added, and the reaction system was adjusted to pH=6 with hydrochloric acid (1M), and extracted with dichloromethane (10 mL×3). The organic layer was dried over anhydrous sodium sulfate, filtered and evaporated to dryness. 10% sodium hydroxide solution (volume ratio of methanol to water was 1:1) (50 mg, 1.3 mmol, 0.5 mL) was added to a solution of the residue in methanol (1 mL), and the reaction system was reacted at 70° C. for 2 hours. The solvent was evaporated to dryness. The system was adjusted to pH=1-2 with dilute hydrochloric acid (1 M), and extracted with dichloromethane:methanol=10:1 (10 mL×3). The organic layer was dried over anhydrous sodium sulfate, filtered, and concentrated. The residue was purified by preparative chromatography, so as to give Example 41 (5 mg, 4% yield). $^1$H NMR (400 MHz, METHANOL-d$_4$) δ 8.67 (br d, J=6.5 Hz, 1H), 7.99 (d, J=2.5 Hz, 1H), 7.69 (br d, J=6.5 Hz, 1H), 4.50 (br d, J=6.5 Hz, 2H), 3.78-3.59 (m, 1H), 3.32-3.30 (m, 1H), 2.18-1.17 (m, 25H), 1.10 (d, J=6.5 Hz, 3H), 0.95-0.89 (m, 6H), 0.76 (s, 3H).

Route 15

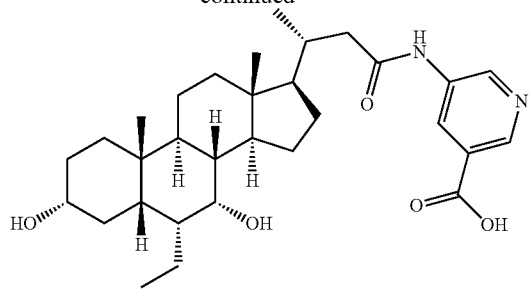

42

Example 42

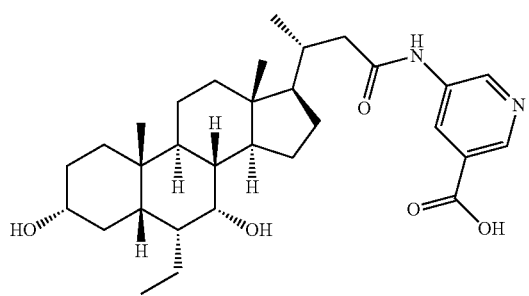

To a solution of Example 16D (100.0 mg, 245.9 μmop and 5-aminopyridine-3-carboxylic acid (50.0 mg, 295 μmol) in DMF (5 mL), 1,3-dicyclohexylcarbodiimide (101.5 mg, 492) and 4-dimethylaminopyridine (1.5 mg, 12.3 μmol) were added. The reaction system was reacted at 30° C. for 16 hours. A solution of lithium hydroxide (10.3 mg, 246 μmol) in water (2.0 mL) was added to the system. The reaction system was reacted at 30° C. for 2 hours. The system was adjusted to pH=4 with hydrochloric acid (1M), and the aqueous phase was extracted with dichloromethane/methanol (10:1) (20 mL×3). The organic layers were combined, and dried over anhydrous sodium sulfate, filtered and evaporated to dryness. The residue was isolated and purified by preparative isolation (HCl), so as to give Example 42 (20 mg, 15.4%). $^1$H NMR (400 MHz, METHANOL-d$_4$) 9.14-9.13 (m, 1H), 8.90-8.89 (m, 1H), 8.71-8.70 (m, 1H), 3.68 (s, 1H), 3.40-3.30 (m, 1H), 2.64-2.61 (m, 1H), 2.15-2.06 (m, 2H), 1.99-1.20 (m, 25H), 1.07 (d, J=6.5 Hz, 3H), 0.95-0.91 (m, 6H), 0.78 (s, 3H).

Route 16

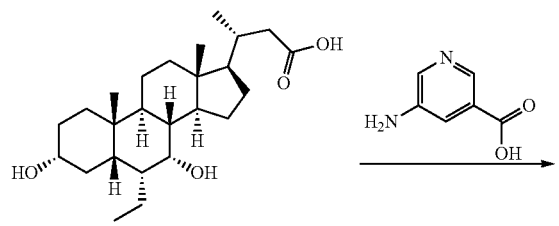

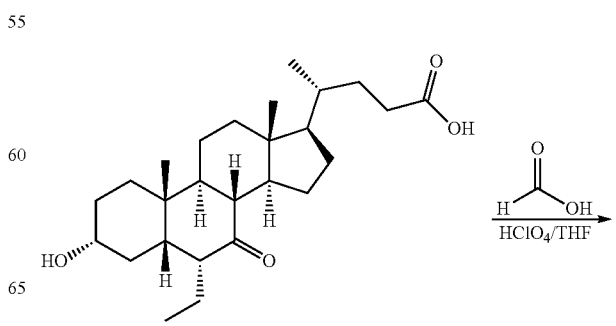

| 99 | 100 |
|---|---|
| -continued | -continued |

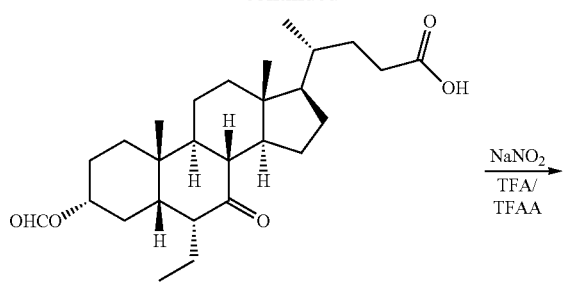

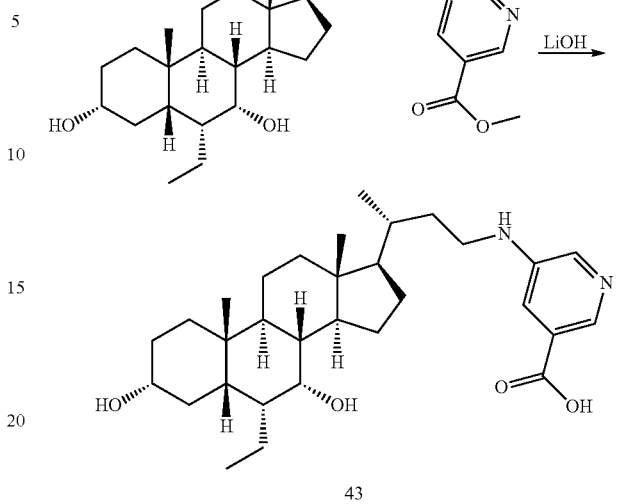

Example 43

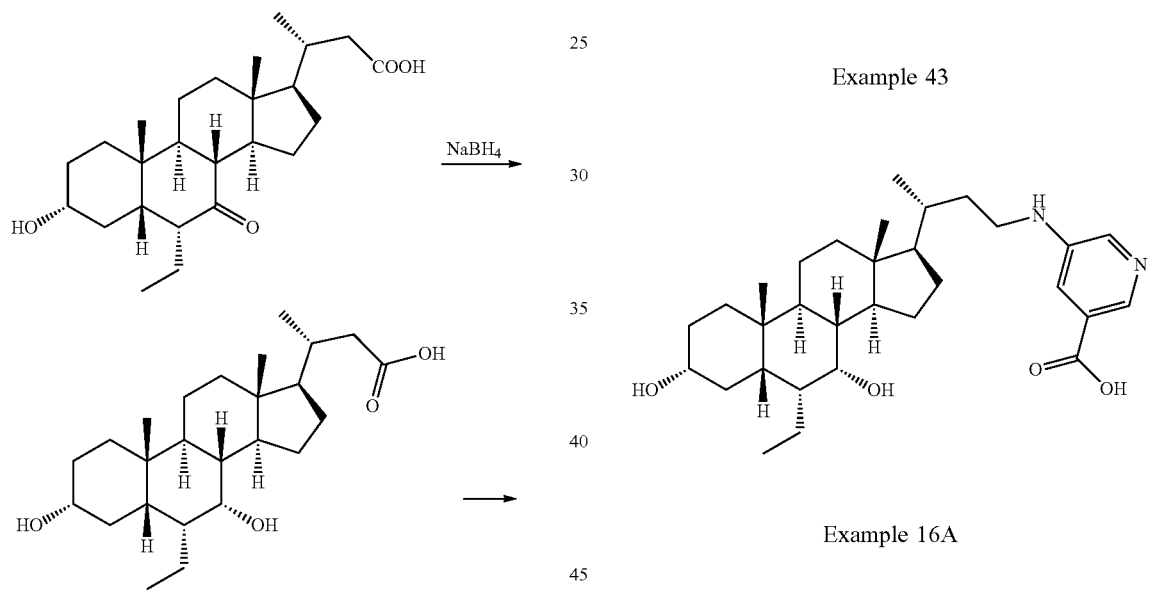

Example 16A

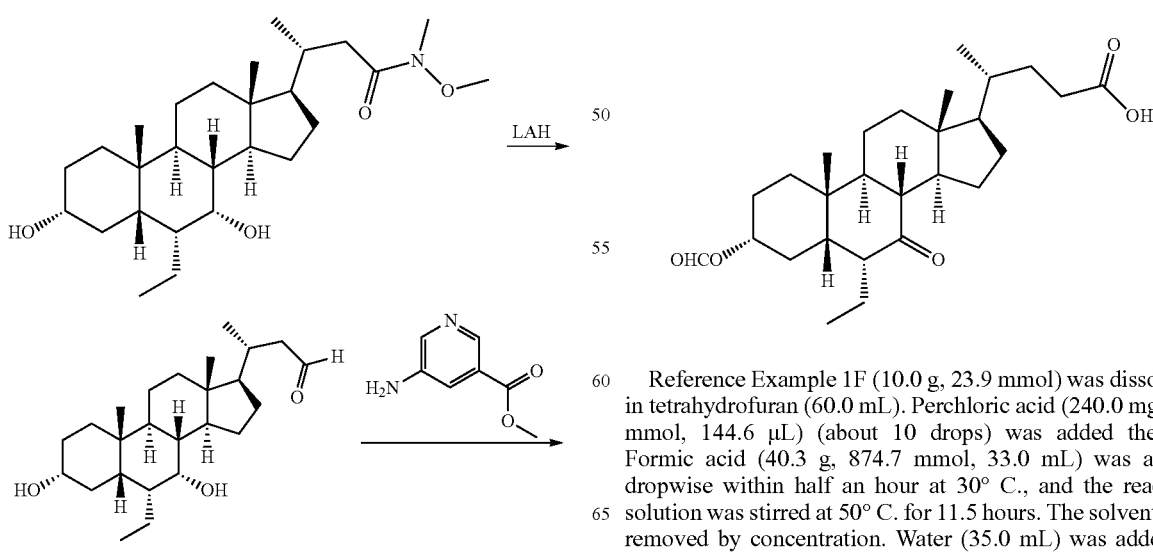

Reference Example 1F (10.0 g, 23.9 mmol) was dissolved in tetrahydrofuran (60.0 mL). Perchloric acid (240.0 mg, 2.4 mmol, 144.6 µL) (about 10 drops) was added thereto. Formic acid (40.3 g, 874.7 mmol, 33.0 mL) was added dropwise within half an hour at 30° C., and the reaction solution was stirred at 50° C. for 11.5 hours. The solvent was removed by concentration. Water (35.0 mL) was added to the reaction solution, which was extracted with ethyl acetate (30.0 mL×3). The organic layer was washed with water (10.0 mL×2), dried over anhydrous sodium sulfate, filtered and concentrated, so as to give a crude product. The crude product was isolated by column chromatography, so as to give Example 16A (7.0 g, 15.7 mmol, 65.6% yield, white solid). $^1$H NMR (400 MHz, CHLOROFORM-d) δ=8.01 (s, 1H), 4.86-4.73 (m, 1H), 2.82-2.67 (m, 1H), 2.47-2.35 (m, 2H), 2.33-2.16 (m, 2H), 2.05-1.93 (m, 2H), 1.89 (d, J=13.1 Hz, 2H), 1.82 (dd, J=5.5, 16.8 Hz, 2H), 1.75 (dd, J=6.5, 14.1 Hz, 3H), 1.71 (br. s., 1H), 1.58-1.30 (m, 7H), 1.26 (s, 3H), 1.23-1.02 (m, 4H), 0.95 (d, J=6.5 Hz, 3H), 0.83 (t, J=7.4 Hz, 3H), 0.68 (s, 3H).

Example 16B

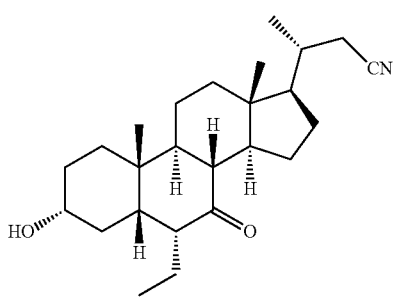

Example 16A (5.8 g, 13.0 mmol) was dissolved in trifluoroacetic acid (40.0 mL) and trifluoroacetic anhydride (20.5 g, 97.4 mmol) at 0° C. After the solid was dissolved, sodium nitrite (2.7 g, 39.0 mmol) was added in portions, which was stirred at 0° C. for another 1 hour, and warmed up to 40° C. and stirred for another 1 h. The reaction solution was cooled to 30° C., and neutralized with 0.5 mol of aqueous sodium hydroxide solution (pH=7-8) at 0° C. The reaction solution was extracted with ethyl acetate (40 mL×3), and the organic layer was washed with water (10 mL), dried over anhydrous sodium sulfate, filtered and concentrated. The crude product was isolated by chromatographic column (silica gel), so as to give Example 16B (3.5 g, 8.5 mmol, 93.0% yield, pale yellow oil). $^1$H NMR (400 MHz, CHLOROFORM-d) δ=3.59-3.47 (m, 1H), 2.69 (q, J=6.2 Hz, 1H), 2.42-2.31 (m, 2H), 2.29-2.15 (m, 2H), 2.01-1.88 (m, 2H), 1.86-1.68 (m, 7H), 1.61-1.45 (m, 6H), 1.26 (t, J=7.2 Hz, 5H), 1.19-1.12 (m, 5H), 1.02-0.91 (m, 1H), 0.80 (t, J=7.4 Hz, 3H), 0.71-0.64 (m, 3H).

Example 16C

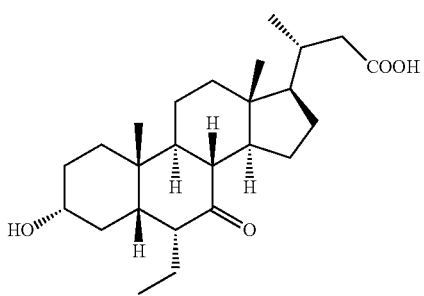

Example 16B (3.5 g, 8.5 mmol) was dissolved in methanol (100.0 mL). Aqueous potassium hydroxide solution (70.0 g, 1.3 mol, dissolved in 100.0 mL of water) was added thereto, and the reaction solution was stirred at 100° C. for 12 hours. A part of the solvent was removed by concentration, and extracted with dichloromethane (30 mL×3). The aqueous phase was acidified with 1 mol of hydrochloric acid (pH=3-4), and extracted with ethyl acetate (30 mL×3). The organic layer was washed with water (20 mL), dried over anhydrous sodium sulfate, filtered and concentrated, so as to give a crude product. Example 16C (3.2 g, 7.9 mmol, 93.5% yield, yellow oil) was obtained without purification. $^1$H NMR (400 MHz, CHLOROFORM-d) δ=3.65-3.50 (m, 1H), 2.71 (d, J=5.8 Hz, 1H), 2.48 (dd, J=2.6, 14.9 Hz, 1H), 2.43-2.31 (m, 2H), 2.22-2.15 (m, 1H), 2.07-1.98 (m, 2H), 1.95-1.86 (m, 3H), 1.82-1.70 (m, 6H), 1.53-1.46 (m, 3H), 1.19-1.10 (m, 6H), 1.02 (d, J=6.3 Hz, 3H), 0.86 (d, J=10.3 Hz, 5H), 0.69 (s, 3H).

Example 16D

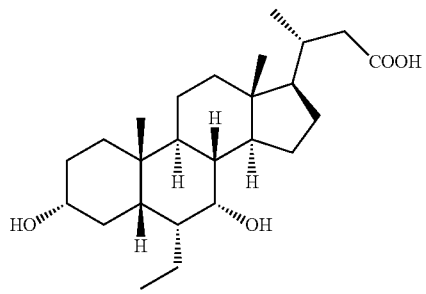

To a solution of aqueous sodium hydroxide (949.2 mg, 23.7 mmol, dissolved in 10.00 mL of water), Example 16C (3.2 g, 7.9 mmol) was added. The reaction solution was warmed up to 80° C., and sodium borohydride (1.8 g, 47.5 mmol) was added in portions. The reaction solution was stirred at 100° C. for 12 hours. Methanol (6 mL) was added dropwise, and concentrated to remove a part of the solvent. The reaction solution was acidified with 1 mol of hydrochloric acid (pH=5-6), extracted with ethyl acetate (40 mL×3). The organic layer was washed with water (20 mL), dried over anhydrous sodium sulfate, filtered and concentrated. Example 16D (3.1 g, 7.6 mmol, 96.4% yield, white solid) was obtained without isolating the crude product. $^1$H NMR (400 MHz, CHLOROFORM-d) δ=3.70 (br. s., 1H), 3.46-3.36 (m, 1H), 2.52-2.39 (m, 1H), 2.02-1.88 (m, 3H), 1.85-1.77 (m, 4H), 1.71-1.59 (m, 3H), 1.53-1.44 (m, 4H), 1.41-1.37 (m, 1H), 1.36-1.27 (m, 4H), 1.24-1.13 (m, 4H), 1.04 (d, J=6.5 Hz, 3H), 0.92-0.88 (m, 6H), 0.73-0.69 (m, 3H).

Example 16E

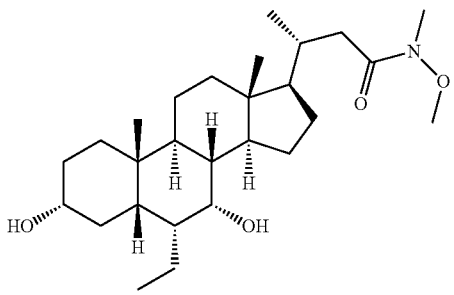

To a solution of Example 16D (100 mg, 245.8 μmol) in acetonitrile (2 mL), triethylamine (49.8 mg, 491.9 mmol, 68.2 μL) and N,O-dimethylhydroxylamine hydrochloride (24.0 mg, 245.9 μmop) were added under nitrogen atmosphere. After being stirred at 25° C. for 30 min, O-benzotriazol-N,N,N',N'-tetramethyluronium tetrafluoroborate (98.7 mg, 307.4 μmop) was then added and stirred for another 11.5 hours. The reaction solution was poured into cold water (30 mL), and extracted with ethyl acetate (40 mL×3). The organic layer was washed with water (20 mL), dried over anhydrous sodium sulfate, filtered and concentrated. Example 16E (90 mg, 91.4% yield, white solid) was obtained without isolating the crude product. $^1$H NMR (400 MHz, CHLOROFORM-d) δ=3.76 (s, 3H), 3.70 (br. s., 1H), 3.46-3.36 (m, 1H), 2.79 (s, 3H), 2.43-2.39 (m, 1H), 2.24-2.18 (m, 1H), 2.00-1.97 (m, 41H), 1.03-0.88 (m, 10H), 0.73 (s, 3H).

Example 16F

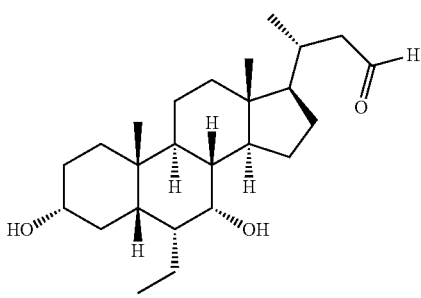

To a solution of lithium aluminum hydride (6.3 mg, 168.9 mop in tetrahydrofuran (2 mL), Example 16E (50 mg, 111.2 μmol) was added at −78° C., and stirred at −78° C. for 2 hours. After the reaction was completed, water (0.006 mL) was added and the reaction solution was filtered. The filter cake was oven-dried to give Example 16F (50 mg, 100%, white solid).

$^1$H NMR (400 MHz, CHLOROFORM-d) δ=9.76 (s., 1H), 3.70 (br. s., 1H), 3.46-3.36 (m, 1H), 2.43-2.39 (m, 1H), 2.24-2.18 (m, 1H), 2.00-1.97 (m, 41H), 1.03-0.88 (m, 10H), 0.73 (s, 3H).

Example 16G

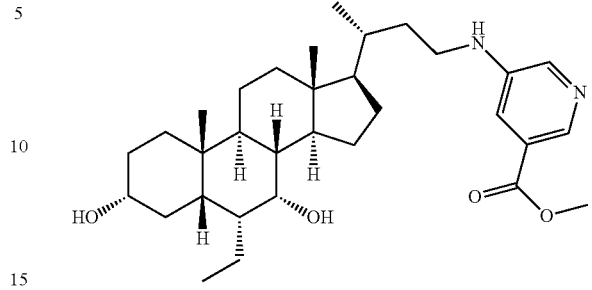

To a solution of Example 16F (150.0 mg, 0.3 mmol) and methyl 5-aminopyridine-3-carboxylate (64.0 mg, 0.4 mmol) in ethyl acetate (5 mL), trifluoroacetic acid (57 μL, 0.8 mmol) and sodium triacetoxyborohydride (146.0 mg, 0.7 mmol) were added. The reaction system was reacted at 20° C. for 16 hours. Ethyl acetate (30 mL) was added to the reaction system. The system was washed with saturated sodium bicarbonate solution (20 mL×2) and saturated saline solution (20 mL×1). The organic layer was dried over anhydrous sodium sulfate, filtered and evaporated to dryness, so as to give the crude product. The crude product was isolated by preparative isolation (TFA) to give Example 16G (60.0 mg, 29.7%). $^1$H NMR (400 MHz, CHLOROFORM-d) 8.44-8.43 (m, 1H), 8.43-8.42 (m, 1H), 7.92-7.91 (m, 1H), 4.01 (s, 3H), 3.72-3.71 (m, 1H), 3.49-3.48 (m, 1H), 3.28-3.13 (m, 2H), 1.99-1.20 (m, 25H), 1.01 (d, J=6.5 Hz, 3H), 0.95-0.87 (m, 6H), 0.67 (s, 3H).

Example 43

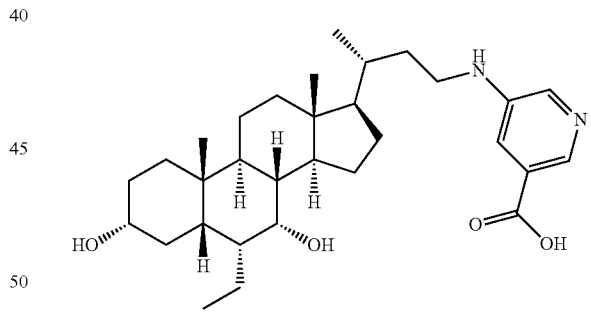

To a solution of Example 16G (60.0 mg, 113.9 μmol) in tetrahydrofuran (2 mL), methanol (1 mL) and water (2 mL), lithium hydroxide (60.0 mg, 1.43 mmol) was added. The reaction system was reacted at 40° C. for 1 hour. The system was adjusted to pH=4 with hydrochloric acid (1M), and the aqueous phase was extracted with dichloromethane/methanol (10:1) (20 mL×3). The organic layers were combined, dried over anhydrous sodium sulfate, filtered and evaporated to dryness. The residue was isolated and purified by preparative isolation (HCl) to give Example 43 (40 mg, 68%). $^1$H NMR (400 MHz, METHANOL-d$_4$) 8.30-8.29 (m, 1H), 8.03-8.02 (m, 1H), 7.59-7.58 (m, 1H), 3.70-3.65 (m, 1H), 3.40-3.30 (m, 1H), 3.12-3.07 (m, 2H), 1.99-1.20 (m, 25H), 1.05 (d, J=6.5 Hz, 3H), 0.95-0.87 (m, 6H), 0.72 (s, 3H).

Route 17

Example 44

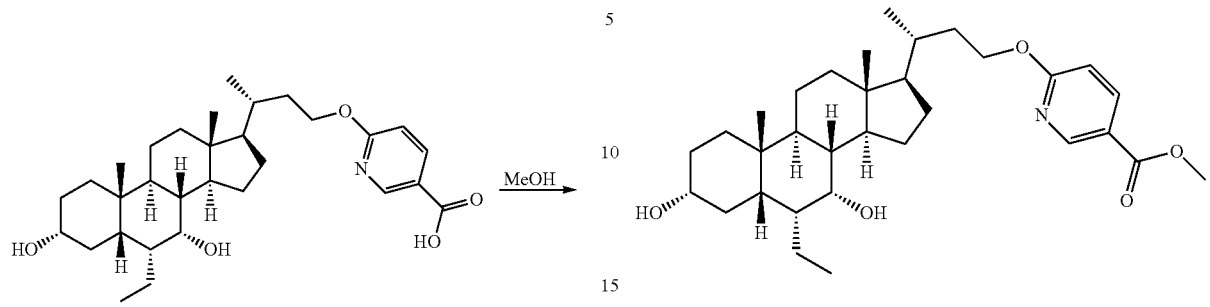

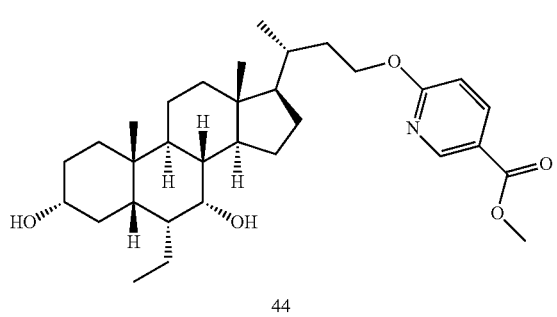

44

Concentrated sulfuric acid (368.0 mg, 3.8 mmol) was added to a solution of Example 22 (50.0 mg, 97.3 μmol) in methanol (5 mL). The reaction system was reacted at 70° C. for 12 hours. Water (5 mL) was added to the system. The system was adjusted to pH=7 with sodium hydroxide (1M), and extracted with dichloromethane (10 mL×3). The organic layer was dried over anhydrous sodium sulfate, filtered and concentrated. The residue was purified by preparative chromatography, so as to give the title compound 44 (15 mg, 29.2% yield). $^1$H NMR (400 MHz, METHANOL-$d_4$) δ 8.76 (d, J=2.0 Hz, 1H), 8.18 (dd, J=2.5, 8.8 Hz, 1H), 6.82 (d, J=8.8 Hz, 1H), 4.49-4.28 (m, 2H), 3.89 (s, 3H), 3.65 (br s, 1H), 3.28 (br s, 1H), 2.03-1.15 (m, 25H), 1.04 (d, J=6.5 Hz, 3H), 0.93-0.86 (m, 6H), 0.71 (s, 3H).

Route 18

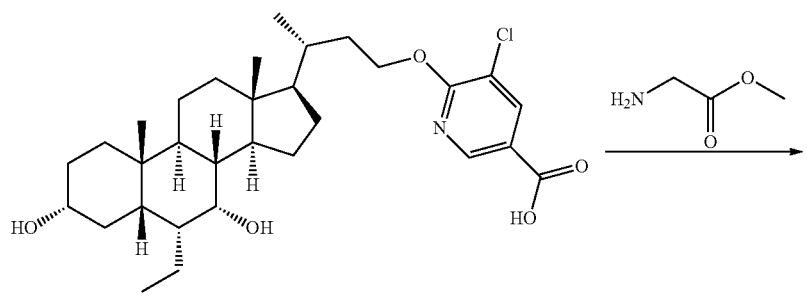

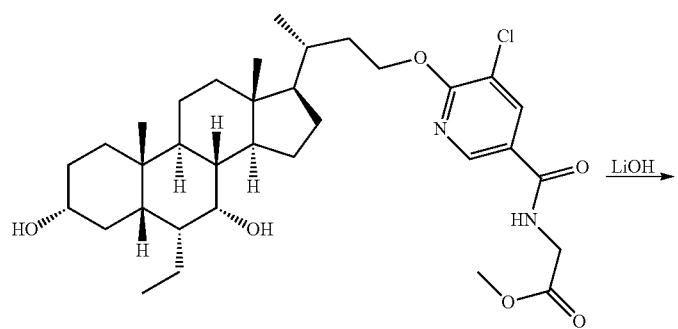

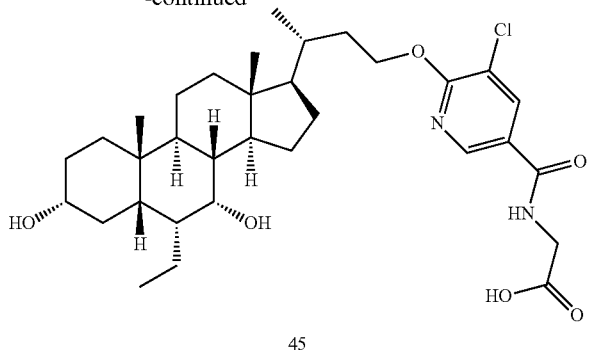

45

Example 45

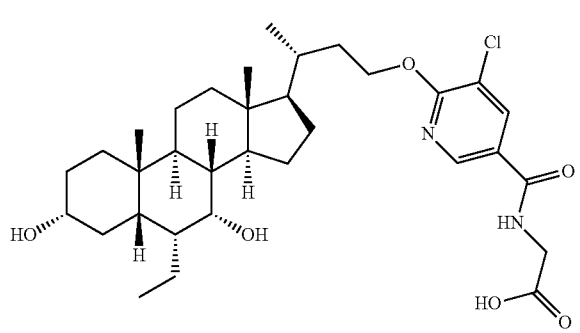

Example 18A

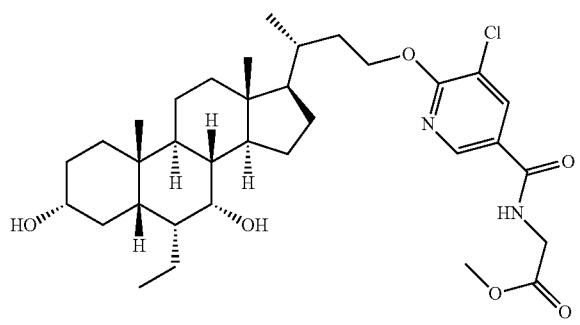

Example 18A was synthesized by using Example 23 as a raw material, and the procedure was referred to the synthesis of Example 12A. The yield was 79.7%. $^1$H NMR (400 MHz, CHLOROFORM-d) δ 8.48 (d, J=2.3 Hz, 1H), 8.08 (d, J=2.3 Hz, 1H), 7.26 (s, 1H), 6.55 (t, J=4.8 Hz, 1H), 4.57-4.38 (m, 2H), 4.24 (d, J=5.0 Hz, 2H), 3.81 (s, 3H), 3.71 (s, 1H), 3.46-3.36 (m, 1H), 2.05-1.12 (m, 33H), 1.06-0.84 (m, 14H), 0.68 (s, 3H).

Example 45

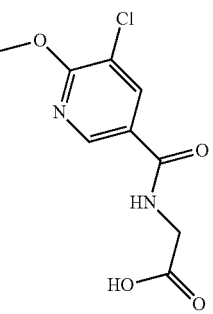

The procedure of Example 45 was referred to the synthesis of Example 39. The yield was 56.8%. $^1$H NMR (400 MHz, METHANOL-d$_4$) δ 8.80-8.72 (m, 1H), 8.48 (d, J=2.0 Hz, 1H), 8.10 (d, J=2.0 Hz, 1H), 4.50-4.33 (m, 2H), 3.99 (d, J=4.5 Hz, 2H), 3.56 (s, 1H), 1.98-1.03 (m, 31H), 1.01-0.87 (m, 5H), 0.84-0.74 (m, 10H), 0.62 (s, 3H).

Example 1: In Vitro Evaluation

FXR Biochemical Experiment

Experimental Purpose:

The activation effect of the compound on FXR binding reaction was detected by AlphaScreen.

Experimental Materials:

1. Protein: Glutathione-S-transferase-labeled FXR human protein (Invitrogen)
2. Co-activator: Biotin-labeled steroid receptor coactivator (Anaspec)
3. Detection reagent: AlphaScreen Detection Kit (PerkinElmer)

Experimental Method:

1. Compound Dilution: The compound to be tested was prepared as a 40 μM DMSO solution, and then diluted 3-fold to 10 concentration points. The reference compound was prepared as a 400 μM DMSO solution, and then diluted 1.5-fold to 10 concentration points. The diluted DMSO solution was added to the wells of a 384-well plate in a volume of 150 nL per well.
2. The glutathione-S-transferase-labeled FXR human protein and the biotin-labeled steroid receptor coactivator were formulated as a mixed solution with concentrations of 0.4 nM and 30 nM, respectively, added to the wells of the 384-well plate in a volume of 15 μL per well, and incubated for 1 hour at room temperature.

4. The mixed solution of acceptor beads in the AlphaScreen Detection Kit was diluted 125-fold, and added to the wells of the 384-well plate in a volume of 7.54 μL per well. The operation during the experimental process was protected from light. The incubation was performed for 1 hour at room temperature.

5. The mixed solution of donor beads in the AlphaScreen Detection Kit was diluted 125-fold, and added to the wells of the 384 well-plate in a volume of 7.5 μL per well. The operation during the experimental process was protected from light. The incubation was performed for 1 hour at room temperature.

6. EC50 test: Envision was used with excitation at 680 nm to read the absorbance signals at 520-620 nm.

7. Analytical data: The data were analyzed via using Prism 5.0, and the EC50 values of the activation effects of the compounds were calculated. The ratio of the highest signal value of the compound to that of the reference compound was then used to give the percentage of activation efficacy of the compound.

FXR Cell Experiment

Experimental Purpose:

The effect of the compound on the cellular functional activity was detected by β-lactamase reporter gene technique.

Experimental Materials:

1. Cell line: FXR HEK 293T DA

2. Cell culture medium: DMEM medium supplemented with 10% serum and Penicillin/Streptomycin (1×)

3. Detection reagent: GeneBLAzer® Reporter Gene Detection Kit (Invitrogen)

Experimental Method:

1. Compound Dilution: The compound to be tested was prepared as a 100 μM DMSO solution, and then the compound was diluted 3-fold to 10 concentration points. The reference compound was prepared as a 100 μM DMSO solution, and then diluted 1.3-fold to 10 concentration points. The diluted DMSO solution was added to the wells of a 384-well plate in a volume of 200 nL per well.

2. Cell inoculation: FXR HEK 293T DA cells were resuscitated, resuspended in a culture medium, diluted to a density of $5 \times 10^5$ cells/mL, and added to the wells of the 384-well plate in a volume of 40 μL per well.

3. The 384-well microplate was incubated at 37° C., 5% $CO_2$ for 16 hours.

4. 6 μL of 1 mM LiveBLAzer™-FRET B/G (CCF4-AM) substrate was mixed with 60 μL of B solution and 934 μL of C solution, and added to the wells of the 384-well plate in a volume of 8 μL per well.

5. The 384-well microplate was incubated in dark for 2 hours at room temperature.

6. EC50 test: Envision was used with excitation at 409 nm to read the absorbance signals at 460 and 530 nm.

7. Analytical data: The data was analyzed via using Prism 5.0, and the EC50 values of the activation effects of the compounds were calculated. The ratio of the highest signal value of the test compound to that of the reference compound (chenodeoxycholic acid, CDCA) was then used to give the percentage of activation efficacy of the compound.

TABLE 1

Test results of $EC_{50}$ for the biochemical experiment and cell experiment:

| Test Samples (Title compound) | FXR enzyme activity $EC_{50}$ (μM) | Efficacy | FXR cell activity $EC_{50}$ (μM) | Efficacy |
|---|---|---|---|---|
| Chenodeoxycholic acid, CDCA | 12.14 | 100% | 10.22 | 100% |
| Example 1 | 0.9 | 320% | 17.9 | 134% |
| Example 2 | 1.46 | 114% | | |
| Example 3 | 2.62 | 106% | | |
| Example 4 | 0.72 | 334% | 1.87 | 131% |
| Example 5 | 0.09 | 134% | 0.57 | 190% |
| Example 6 | 0.36 | 375% | 5.16 | 132% |
| Example 7 | 0.03 | 360% | 0.06 | 140% |
| Example 8 | 0.11 | 264% | | |
| Example 9 | 0.16 | 407% | 0.14 | 130% |
| Example 10 | 0.06 | 188% | 0.2 | 138% |
| Example 11 | 0.03 | 241% | 0.1 | 132% |
| Example 12 | 0.07 | 240% | | |
| Example 13 | 0.39 | 270% | | |
| Example 14 | 0.73 | 195% | | |
| Example 16 | 0.31 | 247% | | |
| Example 17 | 0.60 | 313% | 2.50 | 131% |
| Example 18 | 0.07 | 187% | | |
| Example 19 | 0.15 | 251% | 0.37 | 143% |
| Example 20 | 0.06 | 287% | | |
| Example 22 | 0.006 | 249% | | |
| Example 23 | 0.0025 | 248% | 0.003 | 150% |
| Example 24 | 0.0025 | 138% | | |
| Example 25 | 0.011 | 233% | | |
| Example 26 | 0.13 | 280% | | |
| Example 27 | 0.006 | 212% | | |
| Example 28 | 0.007 | 219% | | |
| Example 29 | 0.012 | 190% | | |
| Example 30 | 0.056 | 150% | | |
| Example 31 | 0.027 | 204% | | |
| Example 32 | 0.650 | 140% | | |
| Example 33 | 0.141 | 194% | | |
| Example 34 | 0.093 | 191% | | |
| Example 38 | 0.02 | 210% | | |
| Example 39 | 0.02 | 205% | | |
| Example 40 | 0.045 | 197% | | |
| Example 41 | 0.08 | 127% | | |
| Example 42 | 1.43 | 121% | | |
| Example 43 | 0.37 | 193% | | |
| Example 44 | 0.330 | 140% | | |

Conclusion: The agonistic effect of the compound of the present invention on FXR receptor is significant, and the agonistic effect on FXR receptor at the cellular level is also significant.

Experimental Example 2: In Vivo Study

Pharmacokinetics in Mice Administrated with Single Compound:

12 male mice ($C_{57}BL/6J$) were randomly divided into two groups, i.e., 6 mice per group. The first group was the intravenous administration group, involving administration at a dose of 2 mg/kg, 2 mL/kg by injecting via tail vein (the vehicle was 10% HPbCD aqueous solution, and if the drug solubility was not satisfactory, the cosolvent was added); the second group was the oral administration group, involving intragastrical administration at a dose of 10 mg/kg, 10 mL/kg (the vehicle was 0.5% HPMC aqueous solution). Plasma (using $K_2$-EDTA as anticoagulant) samples were taken at 0.083, 0.25, 0.5, 1, 2, 4, 6, 8 and 24 hours in the intravenous administration group after administration; and plasma samples were taken at 0.25, 0.5, 1, 2, 4, 6, 8 and 24 hours in the oral administration group after administration. For 6 animals in each group, blood samples were collected for 3 animals at one time point. The first batch of 3 animals was alternately sampled with the second batch of 3 animals.

Plasma sample analysis was performed by using LC-MS/MS. The resultant plasma concentrations were plotted with repect to time, and PK parameters were calculated by using Phoenix WinNonlin 6.3.

TABLE 2

| Compound | | INT-747 | Example 11 | Example 22 | Example 23 |
|---|---|---|---|---|---|
| Dosage (mg/kg) | | 10 | 10 | 10 | 10 |
| PK parameters in plasma | Cmax (nM) | 1013 | 1433 | 936 | 1777 |
| | Tmax (h) | 0.3 | 2 | 0.5 | 0.5 |
| | AUC (nM · h) | 993 | 5173 | 2337 | 1109 |
| | F% | 13% | — | 34% | 20% |

Conclusion: As shown in Table 2, after oral administration at the same dosage, the peak concentration and the drug exposure of compound 11 were higher than those of the control compound INT-747. After oral administration at the same dosage, the peak concentration of compound 22 was close to that of the control compound INT-747, and the drug exposure of compound 22 was higher than that of the control compound INT-747. After oral administration at the same dosage, the peak concentration of compound 23 was higher than that of the control compound INT-747, and the drug exposure of compound 23 was also higher than that of the control compound INT-747.

Liver-Blood Ratio Experiment of Mice Via Cassette Dosing 6 male mice (C57BL/6J) were grouped as an oral administration group. 5 kinds of the developed drugs were contained in the formulation, and intragastrical administration was performed at a dose of 2 mg/kg/compound (the vehicle was 0.5% HPMC aqueous solution). The five compounds were firstly and respectively dissolved in the vehicle, and sonicated or whirled to form a 1 mg/mL solution (clear solution or suspension), respectively; and then the solutions of the five compound were mixed in equal volumes (1:1:1:1:1, v:v:v:v:v) into a glass bottle. After intragastrical oral administration, plasma and liver tissue samples were collected from 3 animals at 0.5 h after administration; corresponding samples were collected from the other 3 animals at 3 h after administration. After collection, the liver tissue was homogenized by using ice-cold homogenization buffer (methanol:15 mM PBS buffer (pH 7.4)=1:2, v:v) based on the ratio of liver weight:homogenization buffer volume=1:3. Plasma and liver tissue samples were analyzed by using a five-in-one LC-MS/MS analysis method developed in advance. The concentrations of plasma and liver tissue homogenate were obtained, and the concentration ratios of liver tissue to plasma were calculated by using Excel.

TABLE 3

| | Compound | INT-747 | Example 22 | Example 26 |
|---|---|---|---|---|
| | Dosage (mg/kg) | 2 | 2 | 2 |
| PK parameters | Concentration in liver (nM) 0.5 h/3 h | 711/625 | 1959/701 | 3904/358 |
| | Concentration in plasma (nM) 0.5 h/3 h | 151/63 | 83/45 | 387/18 |
| | Concentration ratio of liver to plasma 0.5 h/3 h | 5/10 | 24/16 | 10/20 |

Note:
ND indicates "not detected".

Conclusion: As shown in Table 3, after oral administration of the compound in the present invention at the same dosage, the drug concentrations of Example 22 in the liver at 0.5 h and 3 h were higher than those of the control compound, and the liver/blood concentration ratios were also higher than those of the control compound at 0.5 h and 3 h. The drug concentration of Example 26 in the liver at 0.5 h was higher than that of the control compound, and the liver/blood concentration ratios of Example 26 were higher than those of the control compound at 0.5 h and 3 h.

What is claimed is:
1. A compound represented by formula (III),

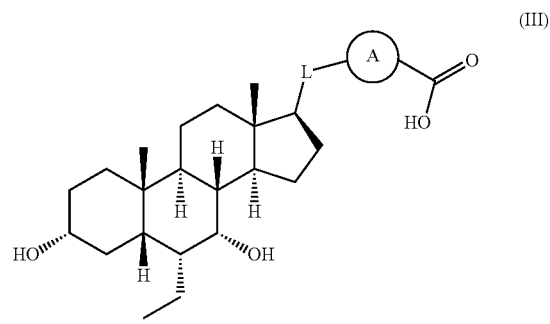

wherein,
ring A is selected from 5- to 12-membered aryl, 5- to 12-membered heteroaryl, 5 to 6-membered non-aromatic heterocyclyl, or 5- to 6-membered cycloalkyl; and said ring A is optionally substituted with 1, 2 or 3 of R;

L is selected from $C_{1-6}$ alkyl, $C_{1-6}$ heteroalkyl, or $C_{2-6}$ alkenyl, and said L is optionally substituted with 1, 2 or 3 of R;

R is selected from F, Cl, Br, I, OH, CN, $NO_2$, $NH_2$, $C_{1-3}$ all ylamino; N,N-di($C_{1-3}$ alkyl)amino, $C_{1-3}$ alkyl, $C_{1-3}$ alkyloxy, or $C_{1-3}$ alkylthio, and said R is optionally substituted with 1, 2 or 3 R';

R' is selected from F, Cl, Br, I, OH, $NH_2$, $NO_2$, CN, COOH, Me, Et, $CH_2F$, $CHF_2$, $CF_3$, $CH_3O$, $CH_3S$, $NH(CH_3)$, or $N(CH_3)_2$;

said "hetero" represents heteroatom or heteroatomic group, selected from —C(=O)NH—, N, —NH—, —C(=NH)—, —S(=O)$_2$NH—, —S(=O)NH—, —O—, —S—, =O, =S, —C(=O)C—, —C(=O)—, —C(=S)—, —S(=O)—, —S(=O)$_2$—, or —NHC(=O)NH—;

in any of the above cases, the number of the heteroatom or heteroatomic groups is independently selected from 1, 2 or 3;

or a pharmaceutically acceptable salt thereof.

2. The compound or the pharmaceutically acceptable salt thereof according to claim 1, wherein R is selected from F, Cl, Br, I, Me, $CF_3$, $CHF_2$, $CH_2F$, Et, OMe, $NH(CH_3)$, or $N(CH_3)_2$.

3. The compound or the pharmaceutically acceptable salt thereof according to claim wherein ring A is selected from phenyl, pyridyl, pyridin-2(1H)-onyl, pyrimidyl, pyrazolyl, imidazolyl, oxazolyl, thiazolyl, thienyl, pyrrolidinyl, piperidinyl, morpholinyl, piperazinyl, isoxazolyl, isothiazolyl, bicyclo[1.1.1]pentyl, benzoxazolyl, benzo[d]isoxazolyl, indazolyl, indolyl, quinolinyl, isoquinolinyl, quinazolinyl, 1H-pyrrolo[2,3-B]pyridyl, indolizinyl benzothiazoyl or benzothienyl, and said ring A is optionally substituted with 1, 2 or 3 of R.

4. The compound or the pharmaceutically acceptable salt thereof according to claim 3, wherein ring A is selected from

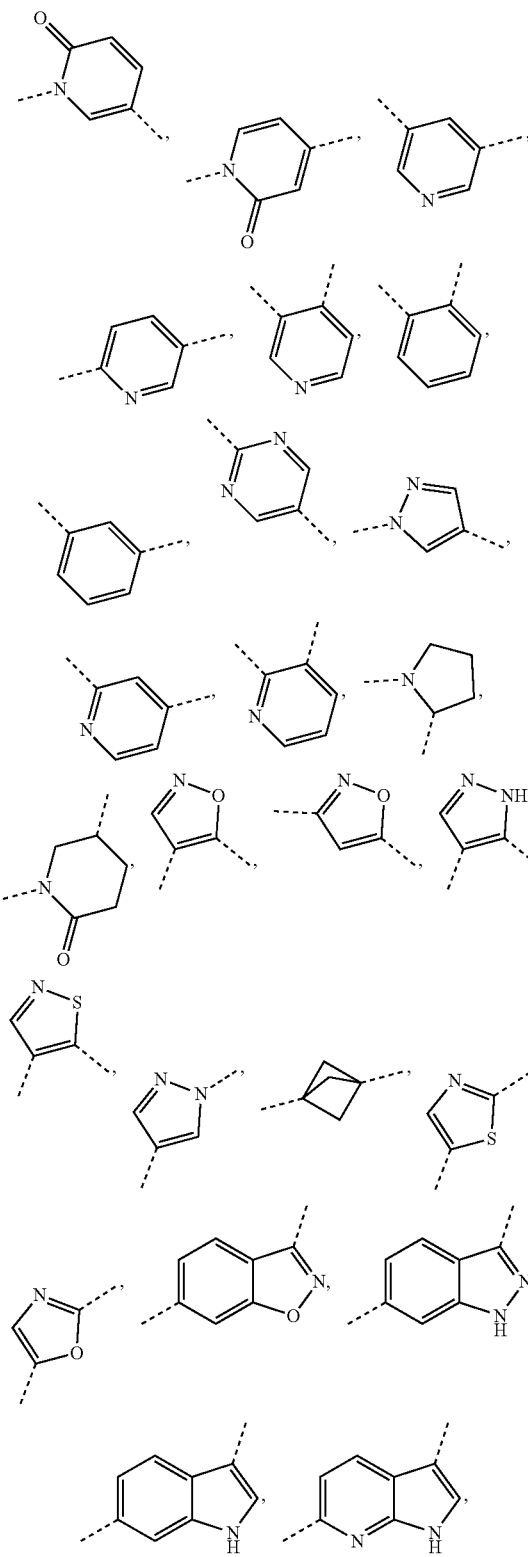
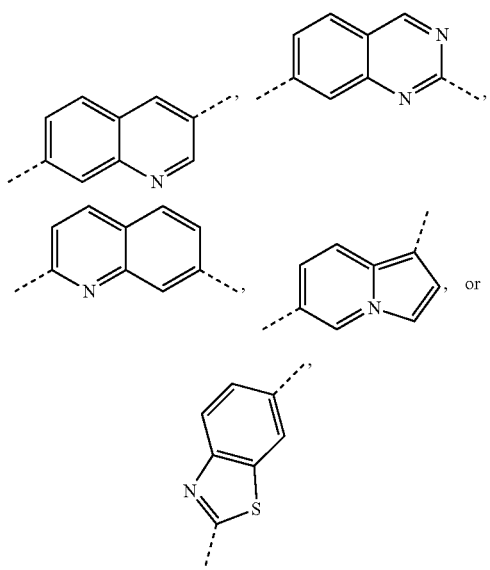

and said ring A is optionally substituted with 1, 2 or 3 R.

5. The compound or the pharmaceutically acceptable salt thereof according to claim 4, wherein ring A is selected from

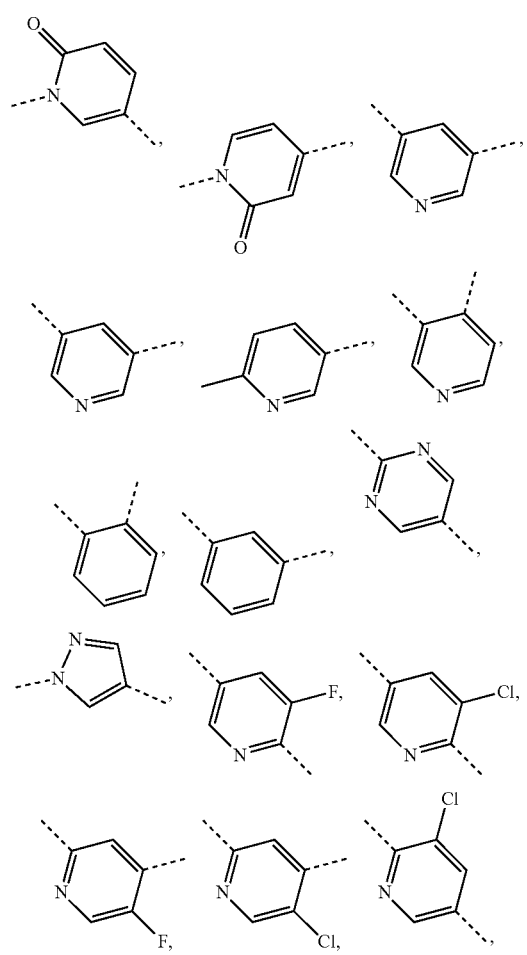

-continued

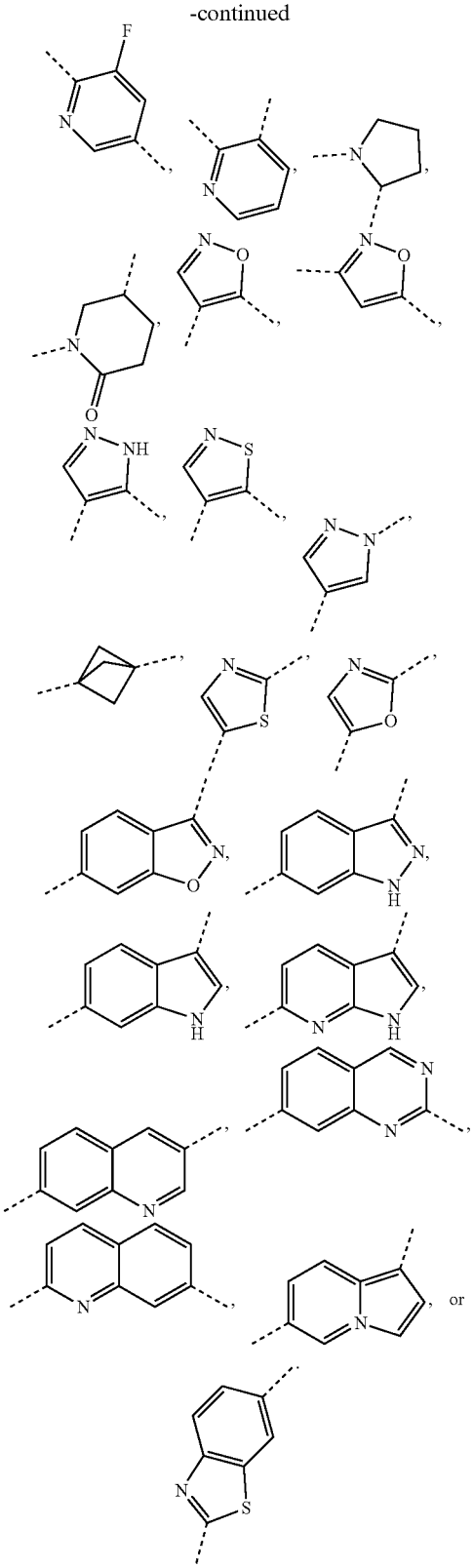

6. The compound or the pharmaceutically acceptable salt thereof according to claim 1, wherein ring A is selected from 6- to 10-membered aryl, 5- to 12-membered heteroaryl containing 1 to 2 heteroatoms, 5- to 6-membered non-aromatic heterocyclyl containing 1 to 2 heteroatoms, or 5- to 6-membered cycloalkyl, and said heteroatom is selected from —NH—, N, —O— or —S—, and said ring A is optionally substituted with 1, 2 or 3 of R.

7. The compound or the pharmaceutically acceptable salt thereof according to claim 6, wherein ring A is selected from 6- to 10-membered aryl, 6- to 10-membered heteroaryl containing 1 to 2 heteroatoms, 5- to 6-membered non-aromatic heterocyclyl containing 1 to 2 heteroatoms, or 5- to 6-membered cycloalkyl, and said heteroatom is selected from —NH—N, O or S, and said ring A is optionally substituted with 1, 2 or 3 of R.

8. The compound or the pharmaceutically acceptable salt thereof according to claim 1, wherein ring A is selected from

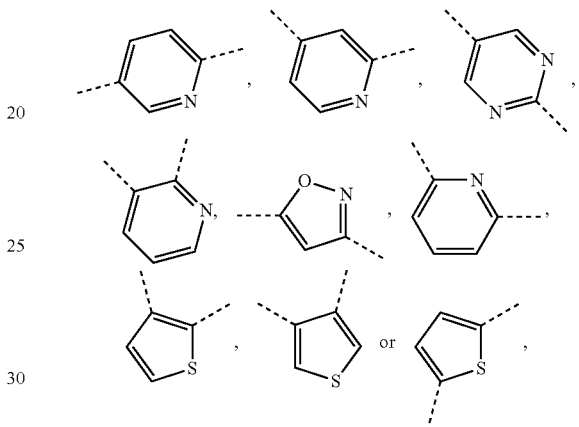

and said ring A is optionally substituted with 1, 2 or 3 R.

9. The compound or the pharmaceutically acceptable salt thereof according to claim 8, wherein ring A is selected from

10. The compound or the pharmaceutically acceptable salt thereof according to claim 1, wherein L is selected from $C_{1-4}$ alkyl, $C_{1-4}$ alkoxy, $C_{1-4}$ alkylthio, $C_{1-4}$ alkylamino, $C_{1-4}$ alkyl-C(=O)NH—, or $C_{2-4}$ alkenyl, and said L is optionally substituted with 1, 2 or 3 R.

11. The compound or the pharmaceutically acceptable salt thereof according to claim 10, wherein L is selected from

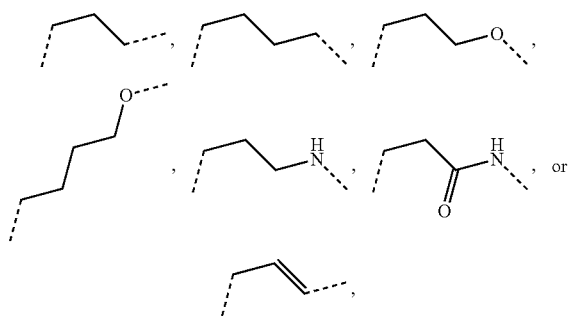

and said L is optionally substituted with 1, 2 or 3 R.

12. The compound or the pharmaceutically acceptable salt thereof according to claim 11, wherein ring A is selected from

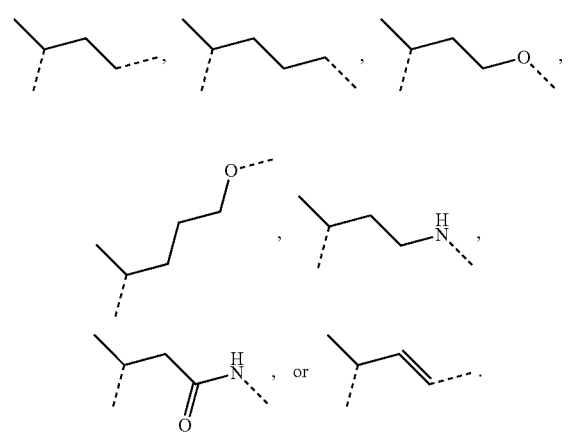

13. The compound or the pharmaceutically acceptable salt thereof according to claim 12, wherein L is selected from

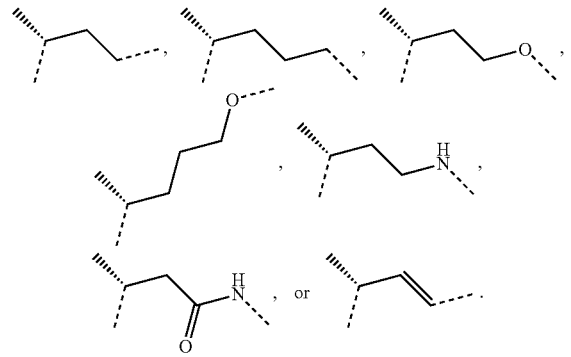

14. The compound or the pharmaceutically acceptable salt according to claim 1, wherein ring A is selected from

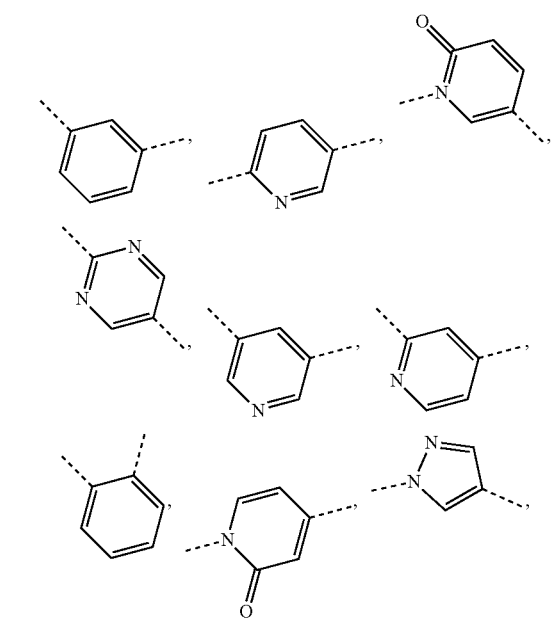

and L is selected from

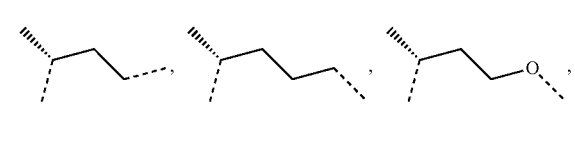

15. The compound or the pharmaceutically acceptable salt thereof thereof according to claim 1, wherein ring A is selected from

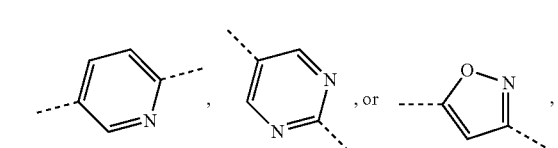

and L is selected from

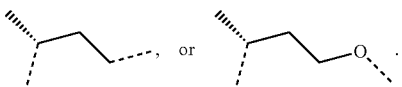

16. A pharmaceutical composition comprising a therapeutically effective amount of the compound or the pharmaceutically acceptable salt thereof according to claim 1, and a pharmaceutically acceptable carrier.

17. A method of treating Farnesoid X Receptor related diseases, comprising administering a therapeutically effective amount of the compound or the pharmaceutically acceptable salt thereof according to claim 1.

18. The method according to claim 17, wherein the diseases are selected from non-alcoholic fatty liver disease (NAFLD), cholestatic hepatopathy, cholestatic liver diseases, hepatitis C infection, alcoholic liver disease, hepatic fibrosis, primary sclerosing cholangitis (PSC), gallstone, biliary atresia, lower urinary tract symptom and benign prostatic hyperplasia (BPH), ureteral calculi, obesity, type 2 diabetes, arteriosclerosis, hepatic function injury resulting from hypercholesterolemia or hyperlipidemia.

19. The method according to claim 18, wherein the Farnesoid X Receptor related diseases are selected from the group consisting of chronic liver disease, fibrotic diseases, hypercholesterol diseases, hypertriglyceride diseases or cardiovascular diseases.

20. The method according to claim 19, wherein the diseases are selected from the group consisting of non-alcoholic steatohepatitis (NASH), primary biliary cirrhosis (PBC) or atherosclerosis.

* * * * *

UNITED STATES PATENT AND TRADEMARK OFFICE
CERTIFICATE OF CORRECTION

PATENT NO. : 11,667,667 B2
APPLICATION NO. : 17/069691
DATED : June 6, 2023
INVENTOR(S) : He et al.

It is certified that error appears in the above-identified patent and that said Letters Patent is hereby corrected as shown below:

In the Specification

At Column 2, Line 51, please delete "Rh" and insert --$R_b$-- therefor.

At Column 2, Line 62, please delete "$R_a$, and $R_d$" and insert --$R_a$, $R_b$, $R_c$, and $R_d$-- therefor.

At Column 8, Line 34, please delete "3 $R_e$" and insert --3 $R_c$-- therefor.

At Column 42, Line 17, please delete "$C_6H_{2n+1}$" and insert --$C_nH_{2n+1}$-- therefor.

At Column 109, Line 6, please delete "volume of 7.54 $\mu$L" and insert --volume of 7.5 $\mu$L-- therefor.

At Column 110, Line 51, please delete "($C_{57}BL/6J$)" and insert --(C57BL/6J)-- therefor.

In the Claims

At Column 112, Line 32 (Claim 1, Line 18), please delete "5_ to 6-membered non-aromatic heterocyclyl" and insert --5- to 6-membered non-aromatic heterocyclyl-- therefor.

At Column 112, Line 33 (Claim 1, Line 19), please delete "5- to 6-membered cycloalkyl;" and insert --5- to 6-membered cycloalkyl,-- therefor.

At Column 112, Line 40 (Claim 1, Lines 25-26), please delete "$C_{1-3}$ all ylamino" and insert --$C_{1-3}$ alkylamino-- therefor.

At Column 112, Line 49 (Claim 1, Lines 35), please delete "-C(=O)C-," and insert -- -C(=O)O-,-- therefor.

At Column 112, Line 61 (Claim 3, Line 2), please delete "according to claim wherein" and insert --according to claim 1, wherein-- therefor.

Signed and Sealed this
Twenty-fourth Day of October, 2023

Katherine Kelly Vidal
*Director of the United States Patent and Trademark Office*

At Column 114, Lines 30-45 (Claim 5, Lines 4-19), please delete

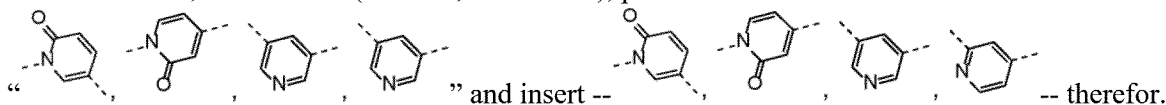

At Column 116, Line 10 (Claim 7, Line 7), please delete "from -NH-N, O or S" and insert --from -NH-, N, O or S-- therefor.

At Column 117, Line 26 (Claim 12, Line 2), please delete "wherein ring A is selected from" and insert --wherein L is selected from-- therefor.

At Column 118, Line 56 (Claim 15, Line 2), please delete "pharmaceutically acceptable salt thereof thereof" and insert --pharmaceutically acceptable salt thereof-- therefor.